(12) United States Patent
Otero Casal et al.

(10) Patent No.: US 10,316,302 B2
(45) Date of Patent: Jun. 11, 2019

(54) PEPTIDE WITH QUORUM-SENSING INHIBITORY ACTIVITY, POLYNUCLEOTIDE THAT ENCODES SAID PEPTIDE, AND THE USES THEREOF

(71) Applicants: UNIVERSIDADE DE SANTIAGO DE COMPOSTELA, Santiago de Compostela, A Coruña (ES); FUNDACIÓN PEDRO BARRIÉ DE LA MAZA, CONDE DE FENOSA, A Coruña (ES)

(72) Inventors: Ana María Otero Casal, A Coruña (ES); Manuel Romero Bernárdez, A Coruña (ES); Celia Mayer Mayer, A Coruña (ES)

(73) Assignees: UNIVERSIDADE DE SANTIAGO DE COMPOSTELA, Santiago de Compostela, A Coruña (ES); FUNDACIÓN PEDRO BARRIÉ DE LA MAZA, CONDE DE FENOSA, A Coruña (ES)

( * ) Notice: Subject to any disclaimer, the term of this patent is extended or adjusted under 35 U.S.C. 154(b) by 263 days.

(21) Appl. No.: 14/904,278

(22) PCT Filed: Jul. 10, 2014

(86) PCT No.: PCT/ES2014/070569
§ 371 (c)(1),
(2) Date: Jan. 11, 2016

(87) PCT Pub. No.: WO2015/004305
PCT Pub. Date: Jan. 15, 2015

(65) Prior Publication Data
US 2016/0244735 A1  Aug. 25, 2016

(30) Foreign Application Priority Data
Jul. 11, 2013  (ES) .................... 201331060

(51) Int. Cl.
| | | |
|---|---|---|
| *C12N 9/18* | (2006.01) | |
| *A01N 63/02* | (2006.01) | |
| *C07K 14/19* | (2006.01) | |
| *A23L 33/18* | (2016.01) | |
| *A61K 38/00* | (2006.01) | |
| *C07K 14/195* | (2006.01) | |

(52) U.S. Cl.
CPC .............. *C12N 9/18* (2013.01); *A01N 63/02* (2013.01); *A23L 33/18* (2016.08); *C07K 14/195* (2013.01); *A23V 2002/00* (2013.01); *A61K 38/00* (2013.01)

(58) Field of Classification Search
None
See application file for complete search history.

(56) References Cited

U.S. PATENT DOCUMENTS

| 7,098,014 B2 | 8/2006 | Zhang et al. |
| 8,586,343 B2 | 11/2013 | Otero Casal et al. |
| 2011/0195051 A1* | 8/2011 | Otero Casal ........... A61K 35/74 424/93.4 |

FOREIGN PATENT DOCUMENTS

| EP | 2356991 A1 | 8/2011 |
| WO | 03068951 A1 | 8/2003 |
| WO | 2010012852 A1 | 2/2010 |

OTHER PUBLICATIONS

Skinnerup et al., "On the Charge Partitioning Between c and z fragments Formed After Electron-Capture Induced Dissociation of Charge-Tagged Lys-Lys and Ala-Lys Dipeptide Dications", J. Am. Soc. Mass Spectrom., 2009, 20, 1881-1889.*
Romero, Manuel, et al.; "Patents on Quorum Quenching: Interfering with Bacterial Communication as a Strategy to Fight Infections," Recent Patents on Biotechnology, 2012, pp. 2-12, vol. 6.
Fast, Walter, et al.; "The enzymes of bacterial census and censorship," Cell Press, Trends in Biochemical Sciences, 2012, pp. 7-14, vol. 37.
Anonymous: Uniprot: A2TYS6, Mar. 2007.
Mayer, C., et al.; "Aii20J, a wide-spectrum thermostable N-acylhomoserine lactonase from the marine bacterium *Tenacibaculum* sp. 20J, can quench AHL-mediated acid resistance in *Escherichia coli*," Appl Microbiol Biotechnol, 2015, pp. 9523-9539, vol. 99.
International Search Report, dated Sep. 30, 2014.
Romero, M., "Interceptacion de senales de comunicacion bacteriana tipo N-acilhomoserin lactonas (AHLs) en bacterias aisladas del medio marino." Doctoral Thesis, May 2010, URL: http://dspace.usc.es/bitstream/10347/2852/1/9788498874501_content.pdf, especially chapter 3.
Romero, M., et al.; "Acylhomoserine lactone production and degradation by the fish pathogen Tenacibaculum maritimum, a member of the Cytophaga-Flavobacterium-Bacteriodes (CFB) group," FEMS Microbiology Letters, 2010, pp. 131-139, vol. 304.

(Continued)

*Primary Examiner* — Suzanne M Noakes
(74) *Attorney, Agent, or Firm* — Tristan A. Fuierer; Olive Law Group, PLLC

(57) ABSTRACT

The invention relates to the cloning, sequencing and characterization of the gene responsible for Quorum Quenching (QQ) activity against Quorum Sensing (QS) signals of the *Tenacibaculum* sp. strain 20J (CECT7426). Said gene encodes a peptide having at least lactonase activity with a percentage of identity less than 38% with the lactonases described up until now for other species, as well as the sequences of the homologous genes present in other species of the genus *Tenacibaculum*. Said peptide shows a broad spectrum of activity degrading optionally substituted N-acyl-homoserine lactones (AHLs) of 4-14 carbon atoms in the side chain thereof, is active at pH comprised between 3 and 9, proteinase K- and chymotrypsin-resistant and does not interact with β-lactam antibiotics.

21 Claims, 14 Drawing Sheets

Specification includes a Sequence Listing.

(56) References Cited

OTHER PUBLICATIONS

Romero, M., et al; "Quorum quenching in cultivable bacteria from dense marine coastal microbial communities," FEMS Microbiology Ecology, 2011, pp. 205-217, vol. 75.

Altschul S.F. et al., "Basic Local Alignment Search Tool," 1990. J Mol Biol; 215(3):403-10.

Bassler, B.L. et al., "Bacterially Speaking," 2006. Cell 125: 237-246.

Bebrone, C. "Metallo-Beta-lactamases (classification, activity, genetic organization, structure, zinc coordination) and their superfamily," 2007. Biochemical Pharmacology 74:1686-1701.

Boles B.R. et al., "agr-Mediated Dispersal of *Staphylococcus aureus* Biofilms," 2008. PLoS Pathog.;4:e1000052.

Bruhn, J. B. et al., "Quorum sensing signal molecules (acylated homoserine lactones) in Gram-negative fish pathogenic bacteria," 2005. Dis. Aquat. Org. 65: 43-52.

Buch, C. et al., "Production of Acylated Homoserine Lactones by Different Serotypes of Vibrio anguillarum Both in Culture and During Infection of Rainbow Trout," 2003. Syst. Appl. Microbiol. 26: 338-349.

Cam, D. T. V. et al., "Novel approach of using homoserine lactone-degrading and poly-beta-hydroxybutyrate-accumulating bacteria to protect artemia from the pathogenic effects of Vibrio harveyi," 2009. Aquaculture 291:23-30.

Cao, Y. et al., "Orally Administered Thermostable N-Acyl Homoserine Lactonase from *Bacillus* sp. Strain A196 Attenuates Aeromonas hydrophila Infection in Zebrafish," 2012. Applied and Environmental Microbiology 78:1899-1908.

Carlier, A. et al., "The Ti Plasmid of Agrobacterium tumefaciens Harbors an attM-Paralogous Gene, aiiB, Also Encoding N-Acyl Homoserine Lactonase Activity," 2003. Appl. Environ. Microbiol. 69: 4989-4993.

Croxatto, A. et al., "VanT, Homologue of Bibrio harveyi LuxR, Regulates Serine, Metalloprotease, Pigment, and Biofilm Production in Vibrio anguillarum," 2002. J. Bacteriol. 184: 1617-1629.

Dong, Y. H. et al., "AiiA, an enzyme that inactivates the acylhomoserine lactone quorum-sensing signal and attenuates the virulence of Erwinia carotovora," 2000. Proc. Natl. Acad. Sci. USA 97: 3526-3531.

Dong Y. H. et al., "Quenching quorum-sensing-dependent bacterial infection by an N-acyl homoserine lactonase," 2001. Nature 411:813-817.

Freeman, J. A., et al., "A genetic analysis of the function of LuxO, a two-component response regulator involved in quorum sensing in Vibrio harveyi," 1999. Mol. Microbiol. 31: 665-677.

Fuqua, C. et al., "Listening in on BacteriaL Acyl-Homoserine Lactone Signalling," 2002. Nature Rev. 3: 685-695.

Hughes DT, et al., "The QseC Adrenergic Signaling Cascade in Enterohemorrahagic *E.coli* (EHEC)," 2009. PLoS Pathog. ;5(8):e1000553.

Morohoshi, T. et al., "Identification of Quorum-Sensing Signal Molecules and the LuxRI Homologs in Fish Pathogen *Edwardsiella tarda*," 2004. J. Biosci. Bioeng. 98: 274-281.

Milton, D., et al., "The LuxM Homologue VanM from Vibrio anguillarum Directs the Synthesis of N-(3-Hydroxyhexanoyl) homoserine Lactone and B-Hexanoylhomoserine Lactone," 2001. J.Bacteriol. 183:3537-3547.

Park, S. Y., et al., "AhlD, an N-acylhomoserine lactonase in *Arthrobacter* sp., and predicted homologues in other bacteria," 2003. Microbiology 149: 1541-1550.

Piñeiro-Vidal, M., et al., "*Tenacibaculum discolor* sp. nov. and *Tenacibaculum gallaicum* sp. nov., isolated from sole (Solea senegalensis) and turbot (Psetta maxima) culture systems," 2008. Int. J. Syst. Evol. Microbiol. 58: 21-25.

Rasmussen, T. B., et al., "Screening for Quorum-Sensing Inhibitors (QSI) by Use of a Novel Genetic System, the QSI Selector," 2005. J. Bacteriol. 187: 1799-1814.

Zhang, H. B. et al., "Genetic control of quorum-sensing signal turnover in Agrobacterium tumefaciens," 2002. Proc. Natl. Acad. Sci. USA 99: 4638-4643.

Romero, M., et al., "Determination of Whether Quorum Quenching Is a Common Activity in Marine Bacteria by Analysis of Cultivable Bacteria and Metagenomic Sequences," 2012. Appl. Environ. Microbiol. 78:6345-6348.

Sharma, V.K., et al. "Evaluation of the impact of quorum sensing transcriptional regulator SdiA on long-term persistence and fecal shedding of *Escherichia coli* O157:H7 in weaned calves," 2013. Microb. Pathog. 57: 21-26.

Whitehead, N. A., et al., "Quorum-sensing in Gram-negative bacteria," 2001. FEMS Microbiol. Rev. 25: 365-404.

Williams, P., et al., "Look who's talking: communication and quorum sensing in the bacterial world," 2007. Phil. Trans. R. Soc. B. 362: 1119-1134.

Riaz, K., et al; "Metagenomics Revealed a Quorum Quenching Lactonase QlcA From Yet Unculturable Soil Bacteria," Comm. Appl. Biol. Sci, 2008, pp. 3-6, vol. 73.

Riaz, K., et al; "A metagenomic analysis of soil bacteria extends the diversity of quorum-quenching lactonases," Environmental Microbiology, 2008, pp. 560-570, vol. 10.

* cited by examiner

SEQUENCE LISTING

```
<160> NUMBER OF SEQ ID NOS: 26

<210> SEQ ID NO 1
<211> LENGTH: 861
<212> TYPE: DNA
<213> ORGANISM: Tenacibaculum sp. strain 20J

<400> SEQUENCE: 1
atgaaaaaaa tatttttatt agctcttacg actattatta catttagttg taaaaatgcc      60 gaaagaagc aaacaacaga agaaaaaaca gttgaaaagc ctcaagtaaa acttcatgtt      120
ttagatggag gttcaatttt agttaacaaa cttgaagttt tttctcaaga tacaacatac      180
acaggacagt ctaaacagtt ttcagatgct tactatgtaa tatctcaccc taaaggaaat      240
ttaatgtggg atgctggttt acctgaagca ctaattactg acgaaccttt tacagagcct      300
agtggtactt ttactttaca acgtaaagac tcattaaaaa accaactaaa atctattggt      360
ttaactgttg atgattttaa atactttgta ttatctcatc ctcatttcga tcatactggt      420
cacgcaaact acttaaaaaa cgcaacatgg ttagttcagg agaacgagta taattttata      480
actaatgact ctgcaaaagt taaagatcct gacacttata attctattaa ggaattaaag      540
aatgtagaaa aaattaatgg tgaccatgac gttttttggag acggcacagt agttattaaa      600
```

```
tacatgccag gtcatacaat aggtcaccaa gctttatata ttgaagctgg tttagaaaaa    660
cctatcttat taacaggtga tttatatcac tttgaagaga atagagaaac taaaggtgtt    720
ccttctttta actacgatgt tgaacaaact ctagaaagca tgaaaaagtt tgaagctttc    780
gctaaagaaa agaatgctga ggtgattatt caacactcac caaagatttt caaaaaatta    840
caaaatctat taaaaaagta a                                               861
```

<210> SEQ ID NO 2
<211> LENGTH: 286
<212> TYPE: PRT
<213> ORGANISM: Tenacibaculum sp. strain 20J

<400> SEQUENCE: 2

```
Met Lys Lys Ile Phe Leu Leu Ala Leu Thr Thr Ile Ile Thr Phe Ser
1               5                   10                  15

Cys Lys Asn Ala Glu Lys Lys Gln Thr Thr Glu Glu Lys Thr Val Glu
            20                  25                  30

Lys Pro Gln Val Lys Leu His Val Leu Asp Gly Gly Ser Ile Leu Val
        35                  40                  45

Asn Lys Leu Glu Val Phe Ser Gln Asp Thr Thr Tyr Thr Gly Gln Ser
    50                  55                  60

Lys Gln Phe Ser Asp Ala Tyr Tyr Val Ile Ser His Pro Lys Gly Asn
65                  70                  75                  80

Leu Met Trp Asp Ala Gly Leu Pro Glu Ala Leu Ile Thr Asp Glu Pro
                85                  90                  95

Phe Thr Glu Pro Ser Gly Thr Phe Thr Leu Gln Arg Lys Asp Ser Leu
            100                 105                 110

Lys Asn Gln Leu Lys Ser Ile Gly Leu Thr Val Asp Asp Phe Lys Tyr
        115                 120                 125

Phe Val Leu Ser His Pro His Phe Asp His Thr Gly His Ala Asn Tyr
    130                 135                 140

Leu Lys Asn Ala Thr Trp Leu Val Gln Glu Asn Glu Tyr Asn Phe Ile
145                 150                 155                 160

Thr Asn Asp Ser Ala Lys Val Lys Asp Pro Thr Tyr Asn Ser Ile
                165                 170                 175

Lys Glu Leu Lys Asn Val Glu Lys Ile Asn Gly Asp His Asp Val Phe
            180                 185                 190

Gly Asp Gly Thr Val Val Ile Lys Tyr Met Pro Gly His Thr Ile Gly
        195                 200                 205

His Gln Ala Leu Tyr Ile Glu Ala Gly Leu Glu Lys Pro Ile Leu Leu
    210                 215                 220

Thr Gly Asp Leu Tyr His Phe Glu Glu Asn Arg Glu Thr Lys Gly Val
225                 230                 235                 240

Pro Ser Phe Asn Tyr Asp Val Glu Gln Thr Leu Glu Ser Met Lys Lys
                245                 250                 255

Phe Glu Ala Phe Ala Lys Glu Lys Asn Ala Glu Val Ile Ile Gln His
            260                 265                 270

Ser Pro Lys Asp Phe Lys Lys Leu Gln Asn Leu Leu Lys Lys
        275                 280                 285
```

<210> SEQ ID NO 3
<211> LENGTH: 1130
<212> TYPE: DNA
<213> ORGANISM: Artificial Sequence
<220> FEATURE:

<223> OTHER INFORMATION: Synthetic Construct

<400> SEQUENCE: 3

```
cgcgaaatta atacgactca ctataggga attgtgagcg ataacaatt cccctctaga      60
aataattttg tttaacttta agaaggagat ataccatggt aaaaaaata tttttattag    120
ctcttacgac tattattaca tttagttgta aaaatgccga aaagaagcaa acaacagaag   180
aaaaaacagt tgaaaagcct caagtaaaac ttcatgtttt agatggaggt tcaattttag   240
ttaacaaact tgaagttttt tctcaagata caacatacac aggacagtct aaacagtttt   300
cagatgctta ctatgtaata tctcacccta aaggaaattt aatgtgggat gctggtttac   360
ctgaagcact aattactgac gaaccttta cagagcctag tggtactttt actttacaac   420
gtaaagactc attaaaaaac caactaaaat ctattggttt aactgttgat gattttaaat   480
actttgtatt atctcatcct catttcgatc atactggtca cgcaaactac ttaaaaaacg   540
caacatggtt agtcaggag aacgagtata atttttataac taatgactct gcaaaagtta   600
aagatcctga cacttataat tctattaagg aattaaagaa tgtagaaaaa attaatggtg   660
accatgacgt ttttggagac ggcacagtag ttattaaata catgccaggt catacaatag   720
gtcaccaagc tttatatatt gaagctggtt tagaaaaacc tatcttatta acaggtgatt   780
tatatcactt tgaagagaat agagaaacta aaggtgttcc ttctttttaac tacgatgttg   840
aacaaactct agaagcatg aaaaagtttg aagctttcgc taaagaaaag aatgctgagg   900
tgattattca acactcacca aaagatttca aaaattaca aaatctatta aaaaagttga   960
attcgagctc cgtcgacaag cttgcggccg cactcgagca ccaccaccac caccactgag  1020
atccggctgc taacaaagcc cgaaaggaag ctgagttggc tgctgccacc gctgagcaat  1080
aactagcata accccttggg gcctctaaac gggtcttgag gggttttttg             1130
```

<210> SEQ ID NO 4
<211> LENGTH: 861
<212> TYPE: DNA
<213> ORGANISM: Tenacibaculum discolor

<400> SEQUENCE: 4

```
atgaaaaaaa tattttat agctcttacg actattattg catttagttg taaaaatgcc      60
gaaaagaagc aaacaacaga gaaaaaaaca gttgaaaagc tcaagtaaa acttcatgtt    120
ttagatggag gttcaatttt agttaacaaa cttgaagttt tttctcaaga tacaacatac   180
acaggacagt ctaaacaatt ttcagatgct tactatgtaa tatctcaccc taaaggaaat   240
ttaatgtggg atgctggttt acctgaagca ctaattactg acaaaccttt tacagagcct   300
agtggtactt ttactttaca acgtaaagac tcattaaaaa accaattaaa atctattggt   360
ttaactgttg atgattttaa atactttgta ttatctcatc ctcatttcga tcatactggt   420
cacgcaaatt acttaaaaaa cgcaacatgg ttagttcagg agaacgaata taattttata   480
actaatgact ctgcaaaagt taaagatcct gacacttata attctattaa ggaattaaag   540
aatgtagaaa aaattaatgg tgaccatgac gttttggag acggcacagt agttatcaaa   600
tacatgccag gtcatacaat aggtcaccaa gctttatata ttgaagctgg tttagaaaaa   660
cctatcttat taacaggtga tttatatcac tttgaagaaa atagagaaac taaaggtgtt   720
ccttctttta actacgatgt tgaacaaact ctagaaagca tgaaaaagtt tgaagctttc   780
gctaaagaaa gaatgctga ggtgattatt caacattcac caaagatttc aaaaaatta    840
caaaatctat taaaaagta a                                               861
```

<210> SEQ ID NO 5
<211> LENGTH: 861
<212> TYPE: DNA
<213> ORGANISM: Tenacibaculum gallaicum

<400> SEQUENCE: 5

| | | | | | |
|---|---|---|---|---|---|
| atgaaaaaaa | tattttatt | agctcttata | agcattatta | caattagttg | taaaaacgct | 60 |
| gaaaagaaac | aaacaacaga | agaaaaaaca | attgagaagc | ctcaggtaaa | acttcatgtt | 120 |
| ttagatggtg | gatcaatttt | agttaacaaa | cttgaagttt | tttctcaaga | cacaacatat | 180 |
| acaggacagt | ctaaaaaact | ttcagatggt | ttttatgtaa | tctctcaccc | taaaggaaac | 240 |
| ttaatgtggg | atgctgggtt | accagaagct | ttaattgtaa | acgagccttt | tactgaacct | 300 |
| actggtacat | ttacattaca | acgtaaagac | tctttaaaga | tcaattaaa | atctttaggt | 360 |
| ttaactatag | atgattttaa | atacatttcc | ctatctcacc | cacattttga | tcatactggt | 420 |
| catgctaact | actttaagaa | ttcaacgtgg | ttaattcagg | agaatgagta | taattttata | 480 |
| actagtgatt | ctgcaaaagt | taaggaccct | gacacctata | attctattaa | ggaattaaaa | 540 |
| aatgtagaaa | aaataaatgg | tgaccatgat | gttttggag | atggtacggt | agttataaaa | 600 |
| tatatgcctg | gtcatactat | aggtcatcaa | gctttatatg | ttgaagctgg | tttagaaaaa | 660 |
| ccaatcttat | taacaggtga | tttatatcac | tttgaagaaa | acagagaaac | taaaggtatt | 720 |
| ccttctttta | attacgatgt | tgagcaaact | ctagaaagta | tgaagaagtt | tgaagctttc | 780 |
| gctaaagaaa | agaatgctga | ggtgattata | caacactcac | caaagatttt | caaaaaatta | 840 |
| caaaatctat | taaaaaagta | a | | | | 861 |

<210> SEQ ID NO 6
<211> LENGTH: 843
<212> TYPE: DNA
<213> ORGANISM: Tenacibaculum solae

<400> SEQUENCE: 6

| | | | | | |
|---|---|---|---|---|---|
| atgaaaaaaa | tattttatt | agctcttact | atccttatta | ttggttgtaa | aaaaaccgaa | 60 |
| aagaaagaag | tacctaacga | agttaaaaag | cccgaagtaa | aattatttca | attagttggt | 120 |
| ggatcaattt | tagtaaataa | attagaggtt | ttttcgcaag | atacaacgta | caccggtcaa | 180 |
| acaaaacagt | ttaccgatgc | ctattatgta | atatcgcacc | caaagggaa | cttaatgtgg | 240 |
| gatgctggtt | tacctgaaaa | cttggtatta | cctgaagcgg | ttactcctgg | cgacggaacc | 300 |
| tttactgtac | aaagacccga | ttctttagca | aatcaattaa | aatcgattgg | ttttaaaatt | 360 |
| gaagatttca | gtattttgc | aatgtctcac | tcgcattttg | atcatactgg | gcatgcaaac | 420 |
| tatatgaaag | acgctacttg | gttgatacaa | gaaacgaat | acaattcggt | tgcaggagat | 480 |
| tctttagcta | aaaaaaatcc | tgcgatagca | gccttaaaaa | atgtacaaaa | attaaacggt | 540 |
| gattatgatg | ttttggtga | cggtactgtt | gttataaaat | acatgccagg | tcatactatt | 600 |
| ggtcatcaag | tattatatat | tgaagcttct | ggagttgaaa | accaatttt | attaacagga | 660 |
| gatttatatc | attttgaaga | aaacagagcc | aacaaaggcg | ttccttcatt | caactataat | 720 |
| gttgaacaaa | ctttagcaag | catgcaaaaa | tttgaagctt | ttgctaaaga | aaaaaatgct | 780 |
| gaggtgatca | ttcaacattc | accaatagct | ttcaaaaaat | tacaaaatct | attaaaaaag | 840 |
| taa | | | | | | 843 |

<210> SEQ ID NO 7

<211> LENGTH: 861
<212> TYPE: DNA
<213> ORGANISM: Tenacibaculum aestuarii

<400> SEQUENCE: 7

| | | |
|---|---|---|
| atgaaaaaaa tattttatt agctcttacg actattattg catttagttg taaaaatgcc | 60 |
| gaaaagaagc aaacaacaga agaaaaaaca gttgaaaagc ctcaagtaaa acttcatgtt | 120 |
| ttagatggag gttcaatttt agttaacaaa cttgaagttt tttctcaaga tacaacatac | 180 |
| acaggacagt ctaaacaatt ttcagatgct tactatgtaa tatctcaccc taaaggaaat | 240 |
| ttaatgtggg atgctggttt acctgaagca ctaattactg acaaaccttt tacagagcct | 300 |
| agtggtactt ttactttaca acgtaaagac tcattaaaaa accaattaaa atctattggt | 360 |
| ttaactgttg atgattttaa atactttgta ttatctcatc ctcatttcga tcatactggt | 420 |
| cacgcaaatt acttaaaaaa cgcaacatgg ttagttcagg agaacgaata taattttata | 480 |
| actaatgact ctgcaaaagt taaagatcct gacacttata attctattaa ggaattaaag | 540 |
| aatgtagaaa aaattaatgg tgaccatgac gttttttggag acggcacagt agttatcaaa | 600 |
| tacatgccag gtcatacaat aggtcaccaa gctttatata ttgaagctgg tttagaaaaa | 660 |
| cctatcttat taacaggtga tttatatcac tttgaagaaa atagagaaac taaaggtgtt | 720 |
| ccttcttttta actacgatgt tgaacaaact ctagaaagca tgaaaaagtt tgaagctttc | 780 |
| gctaaagaaa agaatgctga ggtgattatt caacactcac caaagatttt caaaaaatta | 840 |
| caaaatctat taaaaaagta a | 861 |

<210> SEQ ID NO 8
<211> LENGTH: 861
<212> TYPE: DNA
<213> ORGANISM: Tenacibaculum lutimaris

<400> SEQUENCE: 8

| | | |
|---|---|---|
| atgaaaaaaa tattttatt agctcttacg actattattg catttagttg taaaaatgcc | 60 |
| gaaaagaagc aaacaacaga agaaaaaaca gttgaaaagc ctcaagtaaa acttcatgtt | 120 |
| ttagatggag gttcaatttt agttaacaaa cttgaagttt tttctcaaga tacaacatac | 180 |
| acaggacagt ctaaacaatt ttcagatgct tactatgtaa tatctcaccc taaaggaaat | 240 |
| ttaatgtggg atgctggttt acctgaagca ctaattactg acaaaccttt tacagagcct | 300 |
| agtggtactt ttactttaca acgtaaagac tcattaaaaa accaattaaa atctattggt | 360 |
| ttaactgttg atgattttaa atactttgta ttatctcatc ctcatttcga tcatactggt | 420 |
| cacgcaaatt acttaaaaaa cgcaacatgg ttagttcagg agaacgaata taattttata | 480 |
| actaatgact ctgcaaaagt taaagatcct gacacttata attctattaa ggaattaaag | 540 |
| aatgtagaaa aaattaatgg tgaccatgac gttttttggag acggcacagt agttatcaaa | 600 |
| tacatgccag gtcatacaat aggtcaccaa gctttatata ttgaagctgg tttagaaaaa | 660 |
| cctatcttat taacaggtga tttatatcac tttgaagaaa atagagaaac taaaggtgtt | 720 |
| ccttcttttta actacgatgt tgaacaaact ctagaaagca tgaaaaagtt tgaagctttc | 780 |
| gctaaagaaa agaatgctga ggtgattatt caacactcac caaagatttt caaaaaatta | 840 |
| caaaatctat taaaaaagta a | 861 |

<210> SEQ ID NO 9
<211> LENGTH: 34
<212> TYPE: DNA
<213> ORGANISM: Artificial Sequence

```
<220> FEATURE:
<223> OTHER INFORMATION: Synthetic Construct

<400> SEQUENCE: 9
gattaaccat ggtaaaaaaa atatttttat tagc                                34

<210> SEQ ID NO 10
<211> LENGTH: 35
<212> TYPE: DNA
<213> ORGANISM: Artificial Sequence
<220> FEATURE:
<223> OTHER INFORMATION: Synthetic Construct

<400> SEQUENCE: 10
gctatgaatt caacttttttt aatagatttt gtaat                              35

<210> SEQ ID NO 11
<211> LENGTH: 27
<212> TYPE: DNA
<213> ORGANISM: Artificial Sequence
<220> FEATURE:
<223> OTHER INFORMATION: Synthetic Construct

<400> SEQUENCE: 11
tctcatcctc atttcgatca tactggt                                        27

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
ttggtgacct attgtatgac ctgg                                           24

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct

<400> SEQUENCE: 13
taatacgact cactataggg gaa                                            23

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
gctagttatt gctcagcgg                                                 19

<210> SEQ ID NO 15
<211> LENGTH: 753
<212> TYPE: DNA
<213> ORGANISM: Bacillus sp. 240B1

<400> SEQUENCE: 15
atgacagtaa agaagcttta tttcgtccca gcaggtcgtt gtatgttgga tcattcgtct    60
gttaatagta cattaacacc aggagaatta ttagacttac cggtttggtg ttatcttttg   120
```

-continued

```
gagactgaag aaggacctat tttagtagat acaggtatgc cagaaagtgc agttaataat      180
gaaggtcttt ttaacggtac atttgtcgaa gggcaggttt taccgaaaat gactgaagaa      240
gatagaatcg tgaatatttt aaaacgggtt ggttatgagc cggaagacct tctttatatt      300
attagttctc acttgcattt tgatcatgca ggaggaaatg gcgcttttat aaatacacca      360
atcattgtac agcgtgctga atatgaggcg gcgcagcata gcgaagaata tttgaaagaa      420
tgtatattgc cgaatttaaa ctacaaaatc attgaaggtg attatgaagt cgtaccagga      480
gttcaattat tgcatacacc aggccatact ccagggcatc aatcgctatt aattgagaca      540
gaaaaatccg gtcctgtatt attaacgatt gatgcatcgt atacgaaaga gaattttgaa      600
aatgaagtgc catttgcggg atttgattca gaattagctt tatcttcaat taaacgttta      660
aaagaagtgg tgatgaaaga aagccgatt gttttctttg gacatgatat agagcaggaa       720
aggggatgta aagtgttccc tgaatatata tag                                    753
```

<210> SEQ ID NO 16
<211> LENGTH: 250
<212> TYPE: PRT
<213> ORGANISM: Bacillus sp. 240B1

<400> SEQUENCE: 16

```
Met Thr Val Lys Lys Leu Tyr Phe Ile Pro Ala Gly Arg Cys Met Leu
1               5                   10                  15

Asp His Ser Ser Val Asn Ser Ala Leu Thr Pro Gly Lys Leu Leu Asn
            20                  25                  30

Leu Pro Val Trp Cys Tyr Leu Leu Glu Thr Glu Gly Pro Ile Leu
        35                  40                  45

Val Asp Thr Gly Met Pro Glu Ser Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Thr Glu Tyr
        115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Glu Gln Ser Gly Ser Val Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Pro Glu Leu Ala Leu Ser Ser Ile Lys Arg Leu Lys Glu Val Val
    210                 215                 220

Lys Lys Glu Lys Pro Ile Ile Phe Phe Gly His Asp Ile Glu Gln Glu
225                 230                 235                 240

Lys Ser Cys Arg Val Phe Pro Glu Tyr Ile
                245                 250
```

```
<210> SEQ ID NO 17
<211> LENGTH: 250
<212> TYPE: PRT
<213> ORGANISM: Bacillus thuringiensis

<400> SEQUENCE: 17

Met Thr Val Lys Lys Leu Tyr Phe Ile Pro Ala Gly Arg Cys Met Leu
1               5                   10                  15

Asp His Ser Ser Val Asn Ser Thr Leu Ala Pro Gly Asn Leu Leu Asn
                20                  25                  30

Leu Pro Val Trp Cys Tyr Leu Leu Glu Thr Glu Gly Pro Ile Leu
            35                  40                  45

Val Asp Thr Gly Met Pro Glu Ser Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
                100                 105                 110

Asn Gly Ala Phe Thr Asn Thr Pro Ile Ile Val Gln Arg Thr Glu Tyr
            115                 120                 125

Glu Ala Ala Leu His Arg Glu Glu Tyr Met Lys Glu Cys Ile Leu Pro
    130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Leu Ile Glu Thr Glu Lys Ser Gly Pro Val Leu Leu Thr Ile Asp Ala
            180                 185                 190

Ser Tyr Thr Lys Glu Asn Phe Glu Asp Glu Val Pro Phe Ala Gly Phe
    195                 200                 205

Asp Ser Glu Leu Ala Leu Ser Ser Ile Lys Arg Leu Lys Glu Val Val
    210                 215                 220

Met Lys Glu Lys Pro Ile Ile Phe Phe Gly His Asp Ile Glu Gln Glu
225                 230                 235                 240

Lys Gly Cys Lys Val Phe Pro Glu Tyr Ile
                245                 250

<210> SEQ ID NO 18
<211> LENGTH: 250
<212> TYPE: PRT
<213> ORGANISM: Bacillus sp. AI96

<400> SEQUENCE: 18

Met Thr Val Lys Lys Leu Tyr Phe Leu Pro Ala Gly Arg Cys Met Leu
1               5                   10                  15

Asp His Ser Ser Val Asn Ser Thr Leu Thr Pro Gly Lys Leu Leu Asn
                20                  25                  30

Leu Pro Val Trp Cys Tyr Leu Leu Glu Thr Thr Glu Gly Pro Ile Leu
            35                  40                  45

Ile Asp Thr Gly Met Pro Glu Ser Ala Val Asp Asn Glu Asp Leu Phe
    50                  55                  60

Lys Gly Thr Phe Val Glu Gly Gln Ile Leu Pro Lys Met Lys Pro Asp
65                  70                  75                  80

Asp Arg Ile Val Asn Ile Leu Lys Arg Val Gly Tyr Ala Pro Glu Asp
```

```
                    85                  90                  95
Leu Leu Cys Val Ile Ser Ser His Leu His Phe Asp His Ala Gly Gly
            100                 105                 110

Asn Gly Ser Phe Ser His Ala Pro Ile Ile Val Gln Arg Thr Glu His
            115                 120                 125

Asp Ala Ala Leu His Arg Ala Glu Tyr Leu Lys Glu Cys Ile Leu Pro
130                 135                 140

Asp Leu Asn Tyr Gln Met Ile Glu Gly Asp Tyr Glu Val Met Pro Gly
145                 150                 155                 160

Val Gln Leu Leu Tyr Thr Pro Gly His Ser Pro Gly His Gln Ser Ile
            165                 170                 175

Leu Val Lys Thr Glu Lys Ser Gly Ser Val Leu Leu Thr Ile Asp Ala
            180                 185                 190

Ser Tyr Thr Gln Glu Asn Phe Glu Gln Gly Val Pro Phe Ala Gly Phe
            195                 200                 205

Asp Ser Glu Met Ala Ser Gln Ser Ile Asn Arg Leu Lys Glu Ile Val
210                 215                 220

Leu Asp Glu Lys Pro Ile Val Phe Gly His Asp Met Glu Gln Glu
225                 230                 235                 240

Lys Arg Cys Lys Thr Phe Pro Glu Phe Leu
            245                 250
```

<210> SEQ ID NO 19
<211> LENGTH: 286
<212> TYPE: PRT
<213> ORGANISM: Tenacibaculum discolor

<400> SEQUENCE: 19

```
Met Lys Lys Ile Phe Leu Leu Ala Leu Thr Thr Ile Ile Ala Phe Ser
1               5                   10                  15

Cys Lys Asn Ala Glu Lys Lys Gln Thr Thr Glu Glu Lys Thr Val Glu
            20                  25                  30

Lys Pro Gln Val Lys Leu His Val Leu Asp Gly Gly Ser Ile Leu Val
        35                  40                  45

Asn Lys Leu Glu Val Phe Ser Gln Asp Thr Thr Tyr Thr Gly Gln Ser
    50                  55                  60

Lys Gln Phe Ser Asp Ala Tyr Tyr Val Ile Ser His Pro Lys Gly Asn
65                  70                  75                  80

Leu Met Trp Asp Ala Gly Leu Pro Glu Ala Leu Ile Thr Asp Lys Pro
            85                  90                  95

Phe Thr Glu Pro Ser Gly Thr Phe Thr Leu Gln Arg Lys Asp Ser Leu
            100                 105                 110

Lys Asn Gln Leu Lys Ser Ile Gly Leu Thr Val Asp Asp Phe Lys Tyr
            115                 120                 125

Phe Val Leu Ser His Pro His Phe Asp His Thr Gly His Ala Asn Tyr
130                 135                 140

Leu Lys Asn Ala Thr Trp Leu Val Gln Glu Asn Glu Tyr Asn Phe Ile
145                 150                 155                 160

Thr Asn Asp Ser Ala Lys Val Lys Asp Pro Asp Thr Tyr Asn Ser Ile
            165                 170                 175

Lys Glu Leu Lys Asn Val Glu Lys Ile Asn Gly Asp His Asp Val Phe
            180                 185                 190

Gly Asp Gly Thr Val Val Ile Lys Tyr Met Pro Gly His Thr Ile Gly
            195                 200                 205
```

```
His Gln Ala Leu Tyr Ile Glu Ala Gly Leu Glu Lys Pro Ile Leu Leu
    210                 215                 220

Thr Gly Asp Leu Tyr His Phe Glu Glu Asn Arg Glu Thr Lys Gly Val
225                 230                 235                 240

Pro Ser Phe Asn Tyr Asp Val Glu Gln Thr Leu Glu Ser Met Lys Lys
                245                 250                 255

Phe Glu Ala Phe Ala Lys Glu Lys Asn Ala Glu Val Ile Ile Gln His
            260                 265                 270

Ser Pro Lys Asp Phe Lys Lys Leu Gln Asn Leu Leu Lys Lys
        275                 280                 285
```

<210> SEQ ID NO 20
<211> LENGTH: 286
<212> TYPE: PRT
<213> ORGANISM: Tenacibaculum lutimaris

<400> SEQUENCE: 20

```
Met Lys Lys Ile Phe Leu Leu Ala Leu Thr Thr Ile Ile Ala Phe Ser
1               5                   10                  15

Cys Lys Asn Ala Glu Lys Lys Gln Thr Thr Glu Glu Lys Thr Val Glu
            20                  25                  30

Lys Pro Gln Val Lys Leu His Val Leu Asp Gly Gly Ser Ile Leu Val
        35                  40                  45

Asn Lys Leu Glu Val Phe Ser Gln Asp Thr Thr Tyr Thr Gly Gln Ser
50                  55                  60

Lys Gln Phe Ser Asp Ala Tyr Tyr Val Ile Ser His Pro Lys Gly Asn
65                  70                  75                  80

Leu Met Trp Asp Ala Gly Leu Pro Glu Ala Leu Ile Thr Asp Lys Pro
                85                  90                  95

Phe Thr Glu Pro Ser Gly Thr Phe Thr Leu Gln Arg Lys Asp Ser Leu
            100                 105                 110

Lys Asn Gln Leu Lys Ser Ile Gly Leu Thr Val Asp Asp Phe Lys Tyr
        115                 120                 125

Phe Val Leu Ser His Pro His Phe Asp His Thr Gly His Ala Asn Tyr
130                 135                 140

Leu Lys Asn Ala Thr Trp Leu Val Gln Glu Asn Glu Tyr Asn Phe Ile
145                 150                 155                 160

Thr Asn Asp Ser Ala Lys Val Lys Asp Pro Asp Thr Tyr Asn Ser Ile
                165                 170                 175

Lys Glu Leu Lys Asn Val Glu Lys Ile Asn Gly Asp His Asp Val Phe
            180                 185                 190

Gly Asp Gly Thr Val Val Ile Lys Tyr Met Pro Gly His Thr Ile Gly
        195                 200                 205

His Gln Ala Leu Tyr Ile Glu Ala Gly Leu Glu Lys Pro Ile Leu Leu
    210                 215                 220

Thr Gly Asp Leu Tyr His Phe Glu Glu Asn Arg Glu Thr Lys Gly Val
225                 230                 235                 240

Pro Ser Phe Asn Tyr Asp Val Glu Gln Thr Leu Glu Ser Met Lys Lys
                245                 250                 255

Phe Glu Ala Phe Ala Lys Glu Lys Asn Ala Glu Val Ile Ile Gln His
            260                 265                 270

Ser Pro Lys Asp Phe Lys Lys Leu Gln Asn Leu Leu Lys Lys
        275                 280                 285
```

<210> SEQ ID NO 21

```
<211> LENGTH: 286
<212> TYPE: PRT
<213> ORGANISM: Tenacibaculum aestuarii

<400> SEQUENCE: 21

Met Lys Lys Ile Phe Leu Leu Ala Leu Thr Thr Ile Ile Ala Phe Ser
1               5                   10                  15

Cys Lys Asn Ala Glu Lys Lys Gln Thr Thr Glu Glu Lys Thr Val Glu
            20                  25                  30

Lys Pro Gln Val Lys Leu His Val Leu Asp Gly Gly Ser Ile Leu Val
        35                  40                  45

Asn Lys Leu Glu Val Phe Ser Gln Asp Thr Thr Tyr Thr Gly Gln Ser
    50                  55                  60

Lys Gln Phe Ser Asp Ala Tyr Tyr Val Ile Ser His Pro Lys Gly Asn
65                  70                  75                  80

Leu Met Trp Asp Ala Gly Leu Pro Glu Ala Leu Ile Thr Asp Lys Pro
                85                  90                  95

Phe Thr Glu Pro Ser Gly Thr Phe Thr Leu Gln Arg Lys Asp Ser Leu
            100                 105                 110

Lys Asn Gln Leu Lys Ser Ile Gly Leu Thr Val Asp Asp Phe Lys Tyr
        115                 120                 125

Phe Val Leu Ser His Pro His Phe Asp His Thr Gly His Ala Asn Tyr
    130                 135                 140

Leu Lys Asn Ala Thr Trp Leu Val Gln Glu Asn Glu Tyr Asn Phe Ile
145                 150                 155                 160

Thr Asn Asp Ser Ala Lys Val Lys Asp Pro Thr Tyr Asn Ser Ile
                165                 170                 175

Lys Glu Leu Lys Asn Val Glu Lys Ile Asn Gly Asp His Asp Val Phe
            180                 185                 190

Gly Asp Gly Thr Val Val Ile Lys Tyr Met Pro Gly His Thr Ile Gly
        195                 200                 205

His Gln Ala Leu Tyr Ile Glu Ala Gly Leu Glu Lys Pro Ile Leu Leu
    210                 215                 220

Thr Gly Asp Leu Tyr His Phe Glu Glu Asn Arg Glu Thr Lys Gly Val
225                 230                 235                 240

Pro Ser Phe Asn Tyr Asp Val Glu Gln Thr Leu Glu Ser Met Lys Lys
                245                 250                 255

Phe Glu Ala Phe Ala Lys Glu Lys Asn Ala Glu Val Ile Ile Gln His
            260                 265                 270

Ser Pro Lys Asp Phe Lys Lys Leu Gln Asn Leu Leu Lys Lys
        275                 280                 285

<210> SEQ ID NO 22
<211> LENGTH: 286
<212> TYPE: PRT
<213> ORGANISM: Tenacibaculum gallaicum

<400> SEQUENCE: 22

Met Lys Lys Ile Phe Leu Leu Ala Leu Ile Ser Ile Thr Ile Ser
1               5                   10                  15

Cys Lys Asn Ala Glu Lys Lys Gln Thr Thr Glu Glu Lys Thr Ile Glu
            20                  25                  30

Lys Pro Gln Val Lys Leu His Val Leu Asp Gly Gly Ser Ile Leu Val
        35                  40                  45

Asn Lys Leu Glu Val Phe Ser Gln Asp Thr Thr Tyr Thr Gly Gln Ser
    50                  55                  60
```

```
Lys Lys Leu Ser Asp Gly Phe Tyr Val Ile Ser His Pro Lys Gly Asn
 65                  70                  75                  80

Leu Met Trp Asp Ala Gly Leu Pro Glu Ala Leu Ile Val Asn Glu Pro
                 85                  90                  95

Phe Thr Glu Pro Thr Gly Thr Phe Thr Leu Gln Arg Lys Asp Ser Leu
            100                 105                 110

Lys Asn Gln Leu Lys Ser Leu Gly Leu Thr Ile Asp Asp Phe Lys Tyr
            115                 120                 125

Ile Ser Leu Ser His Pro His Phe Asp His Thr Gly His Ala Asn Tyr
        130                 135                 140

Phe Lys Asn Ser Thr Trp Leu Ile Gln Glu Asn Glu Tyr Asn Phe Ile
145                 150                 155                 160

Thr Ser Asp Ser Ala Lys Val Lys Asp Pro Asp Thr Tyr Asn Ser Ile
                165                 170                 175

Lys Glu Leu Lys Asn Val Glu Lys Ile Asn Gly Asp His Asp Val Phe
            180                 185                 190

Gly Asp Gly Thr Val Val Ile Lys Tyr Met Pro Gly His Thr Ile Gly
            195                 200                 205

His Gln Ala Leu Tyr Val Glu Ala Gly Leu Glu Lys Pro Ile Leu Leu
        210                 215                 220

Thr Gly Asp Leu Tyr His Phe Glu Glu Asn Arg Glu Thr Lys Gly Ile
225                 230                 235                 240

Pro Ser Phe Asn Tyr Asp Val Glu Gln Thr Leu Glu Ser Met Lys Lys
                245                 250                 255

Phe Glu Ala Phe Ala Lys Glu Lys Asn Ala Glu Val Ile Ile Gln His
            260                 265                 270

Ser Pro Lys Asp Phe Lys Lys Leu Gln Asn Leu Leu Lys Lys
            275                 280                 285

<210> SEQ ID NO 23
<211> LENGTH: 280
<212> TYPE: PRT
<213> ORGANISM: Tenacibaculum soleae

<400> SEQUENCE: 23

Met Lys Lys Ile Phe Leu Leu Ala Leu Thr Ile Leu Ile Ile Gly Cys
 1               5                  10                  15

Lys Lys Thr Glu Lys Lys Glu Val Pro Asn Glu Val Lys Lys Pro Glu
                 20                  25                  30

Val Lys Leu Phe Gln Leu Val Gly Gly Ser Ile Leu Val Asn Lys Leu
             35                  40                  45

Glu Val Phe Ser Gln Asp Thr Thr Tyr Thr Gly Gln Thr Lys Gln Phe
         50                  55                  60

Thr Asp Ala Tyr Tyr Val Ile Ser His Pro Lys Gly Asn Leu Met Trp
 65                  70                  75                  80

Asp Ala Gly Leu Pro Glu Asn Leu Val Leu Pro Glu Ala Val Thr Pro
                 85                  90                  95

Gly Asp Gly Thr Phe Thr Val Gln Arg Pro Asp Ser Leu Ala Asn Gln
            100                 105                 110

Leu Lys Ser Ile Gly Phe Lys Ile Glu Asp Phe Lys Tyr Phe Ala Met
            115                 120                 125

Ser His Ser His Phe Asp His Thr Gly His Ala Asn Tyr Met Lys Asp
        130                 135                 140

Ala Thr Trp Leu Ile Gln Glu Asn Glu Tyr Asn Ser Val Ala Gly Asp
```

```
                145                 150                 155                 160
Ser Leu Ala Lys Lys Asn Pro Ala Ile Ala Ala Leu Lys Asn Val Gln
                    165                 170                 175

Lys Leu Asn Gly Asp Tyr Asp Val Phe Gly Asp Gly Thr Val Val Ile
                180                 185                 190

Lys Tyr Met Pro Gly His Thr Ile Gly His Gln Val Leu Tyr Ile Glu
                195                 200                 205

Ala Ser Gly Val Glu Lys Pro Ile Leu Leu Thr Gly Asp Leu Tyr His
            210                 215                 220

Phe Glu Glu Asn Arg Ala Asn Lys Gly Val Pro Ser Phe Asn Tyr Asn
225                 230                 235                 240

Val Glu Gln Thr Leu Ala Ser Met Gln Lys Phe Glu Ala Phe Ala Lys
                    245                 250                 255

Glu Lys Asn Ala Glu Val Ile Ile Gln His Ser Pro Ile Ala Phe Lys
                260                 265                 270

Lys Leu Gln Asn Leu Leu Lys Lys
                275                 280

<210> SEQ ID NO 24
<211> LENGTH: 744
<212> TYPE: DNA
<213> ORGANISM: Artificial Sequence
<220> FEATURE:
<223> OTHER INFORMATION: Synthetic Construct

<400> SEQUENCE: 24
aaaacagtaa aaaagcctca agtaaaacca gcaggtagat ggaggttcaa tcatacgtaa      60
caaaatagaa cattaacacc aagagaaaaa atacacagaa cagtctaaag ttatcagatg     120
cagactaaga aagacctaac ccaaaagaaa aaggaatgcc agatgcaggt aaaaatgaag     180
cactaattaa cggaacattt gacaaagcca agtggtaccg aaaatgaaca agaagacac      240 aataaaaaac aaactaaaac cgattggtta aaagccggaa gaccttaaat acattataag     300
atctcacccg catttcgatc ataccaggaca aaaaaacgac ttaaaaaaca caacaagcat   360
agtacagcga gcagaatatg aaacgacgca gcaaaacgaa aaaaacctga aaaaaagtat   420
attaacgaat taaaacgaaa aaaaaattaa aggtgaccat gaagtcgaaa cagcacagca   480
attattaaat acaccaggcc atacaacagg gcaccaagcg ctataaattg aaacagaaaa   540
agaaaaacct atattattaa caagtgatgc atagcacacg aaagagaata gagaaaataa   600
agtgccatct gcgaaatacg atgcagaaca aactctagaa acaagaaaaa gtttaaaaca   660
agcgctaaag aaaaaaaagc cgaggggatt attcaaaaat cacaaaaaga aggaaaaaaa   720
atacaaaatc taccaaaaaa ataa                                              744

<210> SEQ ID NO 25
<211> LENGTH: 194
<212> TYPE: PRT
<213> ORGANISM: Artificial Sequence
<220> FEATURE:
<223> OTHER INFORMATION: Synthetic Construct

<400> SEQUENCE: 25

Met Thr Val Lys Lys Leu Tyr Phe Leu Pro Ala Gly Arg Cys Leu His
1               5                  10                  15

Ser Ser Val Asn Ser Thr Leu Pro Gly Leu Leu Leu Pro Val Trp Cys
                20                  25                  30

Tyr Leu Leu Glu Thr Glu Gly Pro Ile Asp Thr Gly Pro Glu Ser Ala
```

```
                35                  40                  45
Glu Leu Phe Gly Thr Phe Val Glu Gly Gln Leu Pro Lys Asp Arg Ile
 50                  55                  60

Val Asn Ile Leu Lys Arg Gly Tyr Pro Asp Leu Leu Tyr Ser Ser His
 65                  70                  75                  80

Leu His Phe Asp His Ala Gly Gly Asn Gly Phe Asn Ala Pro Ile Ile
                 85                  90                  95

Val Gln Arg Glu Tyr Ala Ala His Glu Tyr Lys Cys Ile Leu Pro Leu
            100                 105                 110

Asn Tyr Ile Gly Asp Tyr Val Pro Gly Val Gln Leu Leu Tyr Thr Pro
        115                 120                 125

Gly His Thr Pro Gly His Gln Ser Leu Leu Glu Thr Glu Lys Ser Gly
    130                 135                 140

Pro Leu Leu Thr Ile Asp Ala Ser Tyr Thr Glu Asn Phe Glu Gly Val
145                 150                 155                 160

Pro Phe Ala Gly Asp Ser Glu Ala Leu Ser Ile Lys Arg Leu Lys Glu
                165                 170                 175

Val Glu Lys Pro Ile Phe Phe Gly His Asp Glu Glu Lys Cys Lys Phe
            180                 185                 190

Pro Glu
```

<210> SEQ ID NO 26
<211> LENGTH: 261
<212> TYPE: PRT
<213> ORGANISM: Artificial Sequence
<220> FEATURE:
<223> OTHER INFORMATION: Synthetic Construct

<400> SEQUENCE: 26

```
Met Lys Lys Ile Phe Leu Leu Ala Leu Thr Ile Ile Ser Cys Lys
 1               5                  10                  15

Asn Ala Glu Lys Lys Thr Thr Glu Lys Thr Glu Lys Pro Val Lys Leu
             20                  25                  30

His Val Leu Asp Gly Gly Ser Ile Leu Val Asn Lys Leu Glu Val Phe
         35                  40                  45

Ser Gln Asp Thr Thr Tyr Thr Gly Gln Ser Lys Gln Phe Ser Asp Ala
 50                  55                  60

Tyr Val Ile Ser His Pro Lys Gly Asn Leu Met Trp Asp Ala Gly Leu
 65                  70                  75                  80

Pro Glu Ala Leu Glu Pro Phe Thr Glu Pro Gly Thr Phe Thr Leu Gln
                 85                  90                  95

Arg Lys Asp Ser Leu Lys Asn Gln Leu Lys Ser Ile Gly Leu Thr Asp
            100                 105                 110

Phe Lys Tyr Phe Ser His Pro His Phe Asp His Thr Gly His Ala Asn
        115                 120                 125

Tyr Lys Ala Thr Trp Leu Gln Glu Asn Glu Tyr Asn Phe Thr Asp Ser
    130                 135                 140

Ala Lys Val Lys Pro Asp Thr Tyr Asn Ser Ile Lys Glu Leu Lys Asn
145                 150                 155                 160

Val Lys Ile Asn Gly Asp His Asp Val Phe Gly Asp Gly Thr Val Val
                165                 170                 175

Ile Lys Tyr Met Pro Gly His Thr Ile Gly His Gln Ala Leu Tyr Glu
            180                 185                 190

Ala Gly Leu Glu Lys Pro Ile Leu Leu Thr Gly Asp Leu Tyr His Phe
        195                 200                 205
```

-continued

```
Glu Glu Asn Arg Glu Thr Lys Gly Pro Ser Phe Asn Tyr Val Glu Gln
        210             215             220

Thr Leu Glu Ser Met Lys Lys Phe Glu Ala Phe Ala Lys Glu Lys Asn
225             230             235             240

Ala Glu Val Ile Ile Gln His Ser Pro Lys Asp Phe Lys Lys Leu Gln
            245             250             255

Asn Leu Leu Lys Lys
        260
```

PEPTIDE WITH QUORUM-SENSING INHIBITORY ACTIVITY, POLYNUCLEOTIDE THAT ENCODES SAID PEPTIDE, AND THE USES THEREOF

CROSS-REFERENCE TO RELATED APPLICATIONS

This application is filed under the provisions of 35 U.S.C. § 371 and claims the priority of International Patent Application No. PCT/ES2014/070569 filed on 10 Jul. 2014 entitled "PEPTIDE WITH QUORUM-SENSING INHIBITORY ACTIVITY, POLYNUCLEOTIDE THAT ENCODES SAID PEPTIDE, AND THE USES THEREOF" in the name of Ana Maria OTERO CASAL, which claims priority to Spanish Patent Application No. P201331060 filed on 11 Jul. 2013, both of which are hereby incorporated by reference herein in their entirety.

FIELD OF THE INVENTION

The invention generally relates to a peptide with Quorum Sensing (QS) signal inhibitory activity and to uses thereof. The invention also relates to the polynucleotide encoding said peptide, vectors, cells and transgenic non-human organisms comprising said polynucleotide.

BACKGROUND OF THE INVENTION

Use of Quorum Quenching (QQ) Methodologies for the Treatment of Bacterial Infections A number of pathogenic bacteria coordinate their infectious activity by means of intercellular communication processes referred to as Quorum Sensing (QS) (Otero Casal et al., 2004). These processes consist of the release into the medium of small signal molecules that allow the bacteria to quantify the presence of other bacteria by means of specific sensors, acting in a coordinated manner once the threshold concentration of the signal indicating the existence of quorum is reached. QS controls the production of virulence factors, such as exoenzymes or pigments, of a number of human, animal and plant pathogens (Whitehead et al., 2001; Fuqua and Greenberg, 2002; Bassler and Losick, 2006; Williams et al., 2007), including important nosocomial pathogens such as *Pseudomonas aeruginosa*.

Since the virulence of a number of bacterial pathogens depends on QS processes, the inactivation or interception of communication mediated by quorum signals, a strategy generically referred to as quorum sensing inhibition or Quorum Quenching (QQ), is an alternative to the use of antibiotics for the treatment and prevention of bacterial infections. QQ processes have enormous potential in the pharmaceutical and biotechnological fields since it is a virulence biocontrol mechanism that prevents bacteria from launching their attack, making them more sensitive to the host's defenses and making it easier for them to be eliminated with greater efficiency. A key point of QQ strategies is that they do not affect bacteria viability, but rather only interfere in the expression of virulence factors, preventing selective pressure on them, and therefore not generating resistances.

QQ mechanisms are considered to be the new antipathogenic agents, making them an important object of study, since one of the possible uses thereof is the control of both plant and animal pathogens, including human pathogens, acting through QS processes. The QQ process has a lower probability of resistance selection and higher specificity, affecting only the recipient bacteria. Furthermore, the use of QQ strategies accompanied by antibiotics could give rise to the control of multiresistant pathogens, such as *P. aeruginosa*. In aquaculture, the use thereof as antibiotic substitutes is an alternative with great potential due to the legal restrictions on the use of antibiotics in this field, as well as in other animal health fields. In turn, QS and QQ processes take on real importance in the marine environment due to their ecological implications therein, and particularly in the field of aquaculture, because QS processes mediated by N-acyl-homoserine lactones (AHLs) or type 2 autoinducers (AI-2) are very widely spread in marine pathogens, as in the case of *Vibrio harveyi, V. anguillarum, V. salmonicida, V. vulnificus, Aeromonas salmonicida, A. hydrophila, Yersinia ruckeri, Edwarsiella tarda* and *Tenacibaculum maritimum* (Freeman and Bassler, 1999; Swift et al., 1999; Croxatto et al., 2002; Buch et al., 2003; Morohoshi et al., 2004; Bruhn et al., 2005; Romero et al., 2010).

A process controlled by QS phenomena to be highlighted is biofilm formation, which has a huge economic and clinical impact. It is known that many of these biofilms are closely related to human infectious processes. The mechanisms whereby biofilm produces disease symptoms are still not completely established, although it has been suggested that biofilm bacteria can produce endotoxins, groups of bacteria can be released into the bloodstream, they become resistant to the phagocytic action of immune system cells, and, in addition, are a niche for the occurrence of bacteria resistant to antibiotic treatments. This last aspect can be particularly relevant given that resistant bacteria generated in a biofilm could spread from patient to patient through the hands of healthcare staff. Biofilm-forming pathogens are very resistant to antibiotics and can adhere to foods or to substances in contact with such foods, causing both hygiene problems and possible food-borne diseases and, finally, large economic losses. Furthermore, they are often located on the surface of the medical implants or in devices inserted in the organism. They can also be formed in areas of the body that are exposed to the air; particularly, in wounds and in the pleura. In this sense, *Pseudomonas aeruginosa* is one of the most infective and problematic bacteria since it forms biofilms that are hard to treat with conventional antibiotics. In patients with cystic fibrosis, it colonizes the lungs causing hard-to-treat and, often, finally fatal infections. It is also particularly interesting in patients with chronic wounds or burns. In addition, *Staphylococcus aureus* and *Staphylococcus epidermidis* are currently classified as the main causes of nosocomial infections. This situation is favored by the fact that these species live both in mucous membranes and in the skin of human beings which allows them to enter the patient's bloodstream through surgical wounds by means of direct or indirect contact with healthcare staff, with a contaminated object or even with another patient. These species form biofilms that colonize catheters, drains and implants, favoring the contamination and antibiotic resistance. Furthermore, one of the most complex and most clinically relevant biological biofilms is dental plaque, the formation of which is caused by, among other pathogens in the oral cavity, *Streptococcus mutans*, which also forms biofilms. Additionally, biofilms contribute to biological surface contamination, mechanical blockage in conduits, drinkable water distribution systems, air conditioning systems, fire protection systems, etc. Finally, it must be added that they favor biofouling formation as they are the basis for the growth of other higher organisms on submerged surfaces, being a serious economic problem in the aquaculture and marine transport sectors.

Therefore, there is a need to develop new antibacterial agents that increase the arsenal of remedies for controlling bacterial infections.

Marine bacterium *Tenacibaculum* sp. strain 20J (CECT 7426) has high QQ capacity.

*Tenacibaculum* sp. 20J (CECT 7426): A Strain with High QQ Capacity

Marine bacterium *Tenacibaculum* sp. strain 20J (CECT 7426) is characterized by high AHL signal degradation capacity, much greater than other bacteria with QQ activity that have been isolated from soil (Romero et al., 2012). This is the isolate obtained from a sample of marine fish farming tank sediment, in TSA-I medium (Romero, 2010). The partial sequence of the 16S ribosomal RNA gene of the strain has a percentage of identity of 99% with the pathogenic marine bacterium type strain *Tenacibaculum discolor* DSM 18842/NCIMB 14278T, belonging to the phylum *Cytophaga-Flavobacterium-Bacteroides* (CFB), which causes the bacterial infection known as tenacibaculosis/ flexibacteriosis, or gliding bacterial disease (Piñeiro-Vidal et al., 2008). A distinctive feature of *Tenacibaculum* sp. strain 20J (CECT 7426) is that it is capable of growing in media lacking marine salts (TSA-1), so if they are strictly applied, the taxonomic characters established for the genus *Tenacibaculum* would exclude strain 20J from the *T. discolor* species (Piñeiro Vidal et al., 2008). Therefore, the terminology *Tenacibaculum* sp. strain 20J or simply "strain 20J" will be used throughout this text to describe this species. Living cells and cell extracts of strain 20J degrade the entire size range of known AHLs, with or without oxo-substitutions, so the activity thereof is highly unspecific (Romero, 2010). It is a fast-growing strain that can be cultured both in marine environments and in terrestrial environments.

Preliminary studies performed with strain 20J indicate that the main location of its QQ activity is linked with cells, although it is also observed in filtered supernatants (ES 2342807 B2). Furthermore, its activity is constitutive, as it does not require prior exposure to signals for expression. As it presents QS intercepting activity both in living cells and in purified cell extracts (designated as CCEs in ES2342807 B2), it allows the use of both types of presentations for biotechnological use. In addition to having demonstrated its wide spectrum of QQ activity, the comparison of its activity with the data available in the literature confirms its potential because this strain degrades AHLs at a rate that is up to 24 times greater than the marine bacterial consortia selected for their QQ activity (Cam et al., 2009). Comparison of the activity of purified cell extracts of strain 20J with the same extracts of *Bacillus thuringiensis* strain CECT 197 clearly showed greater activity of the purified cell extracts of strain 20J, especially in the case of degrading N-hexanoyl-L-homoserine lactone (C6-HSL): whereas minimum active concentration (MAC) for completely degrading a 10 µM solution of C6-HSL in 24 hours is 10 µg of protein extract per ml for strain 20J, a concentration 3 orders of magnitude greater of *Bacillus thuringiensis* ATCC10792 cell extract, 10,820 µg of protein/ml, is needed to carry out the same degradation (unpublished data). As a result of all its features, strain 20J is a promising candidate for the control of pathogens related to human health, aquaculture, animals and plants or in the inhibition of biofilm formation (Romero, 2010), and therefore these uses have been protected by means of a patent (ES 2342807 B2).

Nevertheless, it has not been possible to identify up until now the gene responsible for its QQ activity or for its degradation activity of QS signals, particularly AHL signals. The identification and characterization of said gene would allow readily providing important amounts of the product responsible for said activity, which would facilitate and generalize the use thereof in any type of uses in which control of QS signal-producing bacterial populations is needed.

The efforts made up until now were unsuccessful in the attempt to clone the gene or genes responsible for QQ activity on QS signals, particularly AHLs, by means of techniques based on polymerase chain reaction (PCR) with degenerate primers, designed for the conserved sequences of lactonases and acylases described in the literature or by means of the construction of a genomic library in the plasmid that was used to transform the AHL-producing strain, *P. aeruginosa* PAOI, carrier of the QSIS pMH655 plasmid (Rasmussen et al., 2005), which was designed for detection of QQ, because the strain cannot survive in the presence of saccharose and AHL. Specifically, none of said methodologies resulted in detection of the genes responsible for QQ activity of strain 20J (unpublished data), which is indicative of the existence of important differences between the enzyme with QQ activity of strain 20J and the enzymes with QQ activity described up until now.

SUMMARY OF THE INVENTION

This invention describes the cloning, sequencing and characterization of the gene responsible for the QQ activity of *Tenacibaculum* sp. strain 20J (CECT 7426) encoding a peptide with QS signal inhibitory activity, particularly with lactonase activity, sometimes referred to as "Aii20J" in this description, having a percentage of identity less than 38% with respect to the sequences of other lactonases described up until now for other species, as well as against sequences of homologous genes present in other species of the genus *Tenacibaculum* the QQ activity of which has already been previously described (ES2342807 B2).

Therefore, in one aspect the invention relates to a polynucleotide comprising the nucleotide sequence shown in SEQ ID NO: 1, or a variant thereof having a degree of identity of at least 76% with respect to said SEQ ID NO: 1 and encoding a peptide with Quorum Sensing (QS) inhibitory activity.

In another aspect, the invention relates to a vector comprising said polynucleotide.

In another aspect, the invention relates to a cell comprising said polynucleotide, or said vector, or the peptide encoded by said polynucleotide, provided that said cell is not a bacterium of the genus *Tenacibaculum*.

In another aspect, the invention relates to a transgenic non-human organism comprising, inserted in the genome thereof, said polynucleotide or said vector, provided that said organism is not a bacterium of the genus *Tenacibaculum*.

In another aspect, the invention relates to a peptide encoded by the nucleotide sequence of said polynucleotide.

In another aspect, the invention relates to a composition comprising said polynucleotide, vector, cell, transgenic non-human organism or peptide. In a particular embodiment, said composition further comprises a vehicle selected from a vehicle suitable for food, a pharmaceutically acceptable vehicle and an agriculturally acceptable vehicle.

In another aspect, the invention relates to a food product comprising said composition and a vehicle suitable for food.

In another aspect, the invention relates to the use of said polynucleotide, vector, cell, transgenic non-human organism or peptide in the preparation of a food product.

In another aspect, the invention relates to a pharmaceutical composition comprising said composition and a pharmaceutically acceptable vehicle.

In another aspect, the invention relates to the use of said polynucleotide, vector, cell, transgenic non-human organism or peptide in the preparation of a medicament for the prevention and/or treatment of a bacterial infection.

In another aspect, the invention relates to an agricultural composition comprising said composition and an agriculturally acceptable vehicle.

In another aspect, the invention relates to a method for controlling a bacterial disease in a plant which comprises contacting said plant with said peptide, wherein said bacterial disease is caused by a QS signal-producing bacterium, under conditions that allow controlling said bacterial disease.

In another aspect, the invention relates to a method for controlling a bacterial disease in a plant, which comprises transforming said plant with said polynucleotide or vector, wherein said bacterial disease is caused by a QS signal-producing bacterium.

In another aspect, the invention relates to a method for controlling a bacterial disease in a plant, comprising the use of a bacterium transformed with said polynucleotide or vector, wherein said bacterial disease is caused by a QS signal-producing bacterium, under conditions that allow controlling said bacterial disease.

In another aspect, the invention relates to the use of said polynucleotide, vector, cell, transgenic non-human organism or peptide, for causing a quorum quenching (QQ) process in response to a QS process, wherein said QS process is caused by a QS signal-producing bacterium.

In another aspect, the invention relates to a method for causing a QQ process in response to a QS process, wherein said QS process is caused by a QS signal-producing bacterium, which comprises contacting said bacterium with said polynucleotide, vector, cell, transgenic non-human organism or peptide, under conditions that allow causing said QQ process.

In another aspect, the invention relates to the use of said polynucleotide, vector, cell, transgenic non-human organism or peptide for inhibiting a QS process, wherein said QS process is caused by a QS signal-producing bacterium.

In another aspect, the invention relates to a method for inhibiting a QS process, wherein said QS process is caused by a QS signal-producing bacterium, which comprises contacting said bacterium with said polynucleotide, vector, cell, transgenic non-human organism or peptide, under conditions that allow inhibiting said QS process.

In another aspect, the invention relates to an in vitro method for degrading a QS signal, which comprises contacting said polynucleotide, vector, cell, transgenic non-human organism or peptide with said QS signal, under conditions that allow degrading said QS signal.

In another aspect, the invention relates to an in vitro method for modulating the signaling activity of an N-acyl-homoserine lactone (AHL), which comprises contacting said polynucleotide, vector, cell, transgenic non-human organism or peptide with said AHL, under conditions that allow modulating the signaling activity of said AHL.

In another aspect, the invention relates to the use of said polynucleotide, vector, cell, transgenic non-human organism or peptide for inhibiting bacterial biofilm formation ex vivo or in vitro.

In another aspect, the invention relates to an in vitro or ex vivo method for inhibiting bacterial biofilm formation, wherein said bacterial biofilm is produced by a QS signal-producing bacterium, which comprises contacting said polynucleotide, vector, cell, transgenic non-human organism or peptide with said QS signal-producing bacterium, under conditions that allow inhibiting said bacterial biofilm formation.

In particular embodiments of the invention, said QS signals produced by the bacterium comprise an AHL, wherein said AHL is (i) unsubstituted AHL, wherein said unsubstituted AHL is selected from the group consisting of C4-HSL, C6-HSL, C8-HSL, C10-HSL, C12-HSL, C14-HSL and combinations thereof; (ii) an oxo- or hydroxy-substituted AHL, wherein said oxo- or hydroxy-substituted AHL is selected from the group consisting of OC6-HSL, OC12-HSL and combinations thereof; or (iii) combinations of (i) and (ii).

BRIEF DESCRIPTION OF THE DRAWINGS

FIG. 5 shows alignment of the nucleotide sequences of aii20J (SEQ ID NO: 1) with lactonase aiiA of *Bacillus* sp. 240B1 (SEQ ID NO: 15) (Dong et al., 2000, accession number AF196486).

FIG. 6 shows alignment of the amino acid sequence of 20J lactonase (Aii20J) (SEQ ID NO: 2) and lactonases from different species of the genus *Bacillus*. The conserved motif characteristic of metallo-β-lactamases (HXHXDH) appears between amino acids 138 and 143 in the figure.

DETAILED DESCRIPTION OF THE INVENTION

1. Polynucleotide of the Invention

Figure 1:
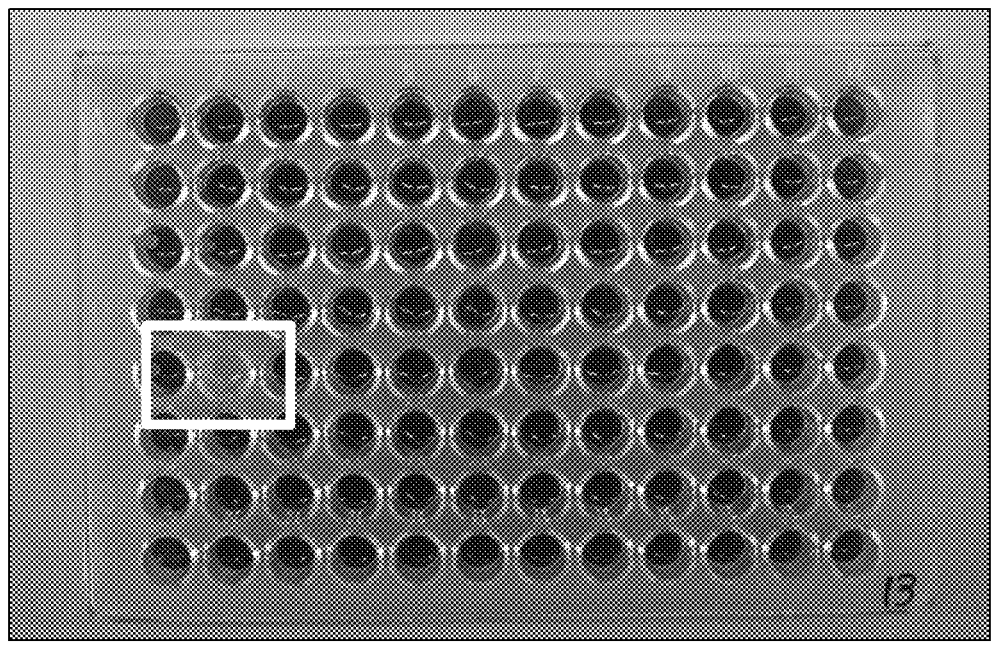
FIG. 1 shows a photograph of the positive clone 13-E2 obtained in the genomic library screening of strain 20J. It is observed that the well appears without any violacein pigment, unlike the rest of the microtiter plate wells, due to degradation of the exogenously added AHL.

In one aspect, the invention relates to a polynucleotide, hereinafter "polynucleotide of the invention," comprising the nucleotide sequence shown in SEQ ID NO: 1, or a variant thereof having a degree of identity of at least 76% with respect to said SEQ ID NO: 1 and encoding a peptide with Quorum Sensing (QS) inhibitory activity.

In the sense used in this description, the term "Quorum Sensing" or "QS," also known as "quorum detection," refers to the capacity of a microorganism to perceive and respond to the population density by means of the regulation of gene expression, therefore being capable of developing a coordinated collective behavior. Therefore, the bacteria communicate their presence to the others using small chemical signaling molecules, known as "QS signals," which release, detect and respond to the accumulation of such signals in the medium. The detection of said QS signals allows the bacterium to distinguish between a high population density and a low population density, such that as the bacterial population grows, the extracellular level of the signal molecule increases until a threshold concentration that is equivalent to a minimum census or quorum triggering a variation in the bacterial gene expression in response to changes in the number of cells is attained. Four main types of QS signals are known:

a) N-acyl-homoserine lactones (AHLs), based on a lactone ring (HSL) to which there is bound, by means of an amide bond, a fatty acid constituting the side chain; said side chain usually has a length of between 4 and 18 carbon atoms, can be saturated or unsaturated and may or may not have oxo- or hydroxy-substitutions in the third carbon atom; illustrative, non-limiting examples of said AHLs include unsubstituted AHLs, such as, for example, N-hexanoyl-L-homoserine lactone (C4-HSL), N-hexanoyl-L-homoserine lactone (C6-HSL), N-octanoyl-L-homoserine lactone (C8-HSL), N-decanoyl-L-homoserine lactone (C10-HSL), N-dodecanoyl-L-homoserine lactone (C12-HSL), N-tetradecanoyl-L-homoserine lactone (C14-HSL), etc., as well as oxo- or hydroxy-substituted AHLs, such as, for example, N-oxohexanoyl-L-homoserine lactone (006-HSL), N-oxododecanoyl-L-homoserine lactone (OC12-HSL), etc. Such AHL signals are fairly common in Gram-negative bacteria, although they have also been found in other phyla (e.g., in some cyanobacteria, in members of Cythophage-*Flavobacterium-Bacteroides* (CFB), also known as Bacteroidetes);

b) Autoinducing peptides (AIPs) correspond to low molecular weight peptides (usually having between 5 and 34 amino acid residues) which experience post-translational modifications; different families of AIPs are known. Illustrative, non-limiting examples of said AIPs include nisin, *staphylococcus* AIP-1, as well as isoprenylated tryptophan peptides. AIP signals of this type are fairly common in Gram-positive bacteria; and c) Type $\mu$ autoinducers (AI-2), the structure of which is a furanosyl borate diester, which are found in both Gram-positive and Gram-negative bacteria. Illustrative, non-limiting examples of this AI-2 include (2S,4S)-2-methyl-2,3,3,4-tetrahydroxytetrahydrofuran-borate, (2R,4S)-2-methyl-2,3,3,4-tetrahydroxy-tetrahydrofuran-borate, etc.

d) AI-3, the structure of which is unknown and is thought to be related to the communication between prokaryotes and eukaryotes, establishing crosstalk mechanisms with the eukaryotic hormones epinephrine and norepinephrine, and which has been described in enterohemorrhagic *Escherichia coli* strains and other enterobacteria.

In the sense used in this description, a peptide with "Quorum Sensing (QS) inhibitory activity" generally refers to a peptide inhibiting a QS process mediated by QS signals, wherein said QS signals are selected from AHLs, APIs, AI-2, AI-3 and combinations thereof.

In a particular embodiment, said peptide with QS inhibitory activity is a peptide inhibiting the signals mediated by AHLs hydrolyzing the lactone ring present in said AHLs, such as a peptide with lactonase activity, i.e., a peptide that hydrolyzes lactone (HSL ring) generating the corresponding hydroxy-carboxylic acid. The lactonase activity of the peptide of the invention (defined below) can be determined by means of various enzyme assays known by one skilled in the art. Generally, all enzyme assays suitable for such purpose measure the substrate consumed or the product generated in the reaction during a given time period. In a particular case, enzyme activity can be determined by measuring the initial rate of reaction, the method whereby measurements are taken in a very short period of time and at substrate saturating concentrations, so the free substrate concentration is considered to be the same as the initial substrate and the measured rate is the maximum rate achieved in the given reaction conditions. In another particular case, enzyme activity can be determined by means of the measurement of the progression of the curve during the reaction, wherein the concentration of the substrate consumed or of the product obtained is determined as a function of time. In another particular case, enzyme activity can be determined by means of the measurement of the substrate or product concentration in the transitory initial rapid phase of the enzymatic reaction in which the intermediate molecular complex reaches a constant kinetic period. In another particular embodiment, enzyme activity can be determined in the equilibrium phase of the reaction, which consists of the disturbance of the equilibrium of the enzymatic reaction by modifying the reaction conditions such as temperature, pH, pressure, etc., and the study of how the enzyme, substrate and product mixture goes back to equilibrium conditions.

Lactonase activity of a peptide can be determined by any suitable conventional method known by those skilled in the art. Said method can be based on the determination of the amount of substrate consumed or of product generated in the reaction during a given time period. To that end, the substrate suitable for the lactonase activity to be assayed will be used. In the experimental part included in this description, different assays suitable for determining the lactonase activity of a peptide are described (see, for example, Example 3, section 3.3).

In a particular embodiment, the lactonase activity of a peptide is determined by means of hydrolysis of a lactone, preferably, an AHL, such as an unsubstituted AHL, for example, C4-HSL, C6-HSL, C8-HSL, C10-HSL, C12-HSL or C14-HSL, or an oxo- or hydroxy-substituted AHL, for example, OC6-HSL or OC12-HSL. By way of non-limiting illustration, the lactonase activity of a peptide can be carried out by means of an assay which comprises contacting said peptide with the corresponding substrate, for example, C6-HSL, C10-HSL, OC6-HSL, etc., under suitable conditions and subsequently evaluating the presence of non-degraded substrate by means of a plate bioassay with the bioindicator strains *Chromobacterium violaceum* CV026 and *C. violaceum* VIR07, or by means of analysis of substrate degradation kinetics (e.g., an AHL such as C6-HSL, C10-HSL or 006-HSL) as a result of degradation by the peptide under study and assessment of the AHL concentration by means of HPLC-MS according to the methodology specified in Romero et al., 2011.

In another particular embodiment, said peptide with QS inhibitory activity is a peptide that degrades or inhibits AIP-type signals, such as a peptide with hydrolase activity, i.e., a peptide hydrolyzing the AIP peptide or inhibiting activity of the signal mediated by said AIP. Inhibitory activity of signals mediated by AIPs can be determined by conventional methods known by those skilled in the art, such as the methods described in Boles and Horswill, 2008.

In another particular embodiment, said peptide with QS inhibitory activity is a peptide that degrades or inhibits AI-2 signals, such as a peptide with hydrolase activity, i.e., a peptide hydrolyzing AI-2 or inhibiting activity of the signal mediated by said AI-2. Inhibitory activity of signals mediated by AI-2 can be determined by conventional methods known by those skilled in the art. In a particular embodiment, AI-2 degradation activity is determined using cultures of different strains of the bioluminescent marine species *Vibrio harveyi* with specific mutations in the QS systems controlling light production, to which the peptide with QS inhibitory activity is added, and the amount of light produced is evaluated. Specifically, in strain JMH597 of this species, only the AI-2 channel (AHL-, AI-2+, CAI-1-) is active, so if the peptide added to the culture presents QQ activity against AI-2, light would not be produced specifically in this strain.

In another particular embodiment, said peptide with QS inhibitory activity is a peptide that degrades or inhibits signals mediated by AI-3, such as a peptide with hydrolase activity, i.e., a peptide hydrolyzing AI-3 peptide or inhibiting activity of the signal mediated by said AI-3. Inhibitory activity of signals mediated by AI-3 can be determined by conventional methods known by those skilled in the art, such as the methods described in Hughes et al, 2009.

SEQ ID NO: 1 has been identified from *Tenacibaculum* sp. strain 20J (CECT 7426), a marine bacterium with high AHL signal degradation capacity, as mentioned in Spanish patent E52342807, by means of an assay based on the construction of a genomic library of *Tenacibaculum* sp. strain 20J in fosmid and functional screening, as described in Example 1. Said SEQ ID NO: 1 encodes a peptide with QS inhibitory activity. Assays performed by the inventors have clearly shown that the peptide the amino acid sequence of which is shown in SEQ ID NO: 2 (defined below), encoded by said SEQ ID NO: 1, inhibits QS signals mediated by AHLs because it has at least lactonase activity and it hydrolyzes AHLs (Example 3).

Therefore, in a particular embodiment, the polynucleotide of the invention comprises the nucleotide sequence shown in SEQ ID NO: 1. SEQ ID NO: 1 includes both the start codon (ATG) and the stop codon (TAA).

In another particular embodiment, the nucleotide sequence of the polynucleotide consists of the nucleotide sequence shown in SEQ ID NO: 1.

In another particular embodiment, the polynucleotide of the invention is a substantially homologous and functionally equivalent variant of the polynucleotide the nucleotide sequence of which is shown in SEQ ID NO: 1.

In the sense used in this description, a polynucleotide is "substantially homologous" to the polynucleotide of SEQ ID NO: 1 when the nucleotide sequence thereof has a degree of identity with respect to the nucleotide sequence shown in SEQ ID NO: 1 of at least 76%, advantageously of at least 85%, preferably of at least 90%, more preferably of at least 91%, 92%, 93%, 95%, 96%, 97% or 98%, and still more preferably of at least 99%. The degree of identity between two nucleotide sequences can be determined by conventional methods, for example, by means of standard sequence alignment algorithms known in the state of the art, such as BLAST, for example (Altschul S. F. et al. 1990). By way of illustration, a polynucleotide substantially homologous to the polynucleotide the nucleotide sequence of which comprises or consists of the nucleotide sequence shown in SEQ ID NO: 1 can be constructed based on the nucleotide sequence shown in said SEQ ID NO: 1 by means of introducing, for example, nucleotides or codons encoding amino acids constituting conservative or non-conservative substitutions with respect to the amino acids encoded by the nucleotide sequence shown in SEQ ID NO: 1. Other illustrative examples of possible modifications include the insertion of one or more nucleotides in the sequence, the addition of one or more nucleotides at any of the ends of the sequence, or the deletion of one or more nucleotides at any end or within the sequence.

In the sense used in this description, a polynucleotide is "functionally equivalent" to the polynucleotide the nucleotide sequence of which comprises or consists of the nucleotide sequence shown in SEQ ID NO: 1 when it encodes a peptide having QS inhibitory activity. The inhibitory activity of the peptide encoded by the polynucleotide functionally equivalent to the polynucleotide the nucleotide sequence of which comprises or consists of the nucleotide sequence shown in SEQ ID NO: 1 can be determined by conventional methods for determining said QS inhibitory activity (e.g., inhibitory activity of signals mediated by AHLs, AIPs, AI-2 and/or AI-3), such as those methods mentioned above.

In a particular embodiment, the polynucleotide of the invention is a substantially homologous and functionally equivalent variant thereof, i.e., it is a polynucleotide the nucleotide sequence of which has a degree of identity of at least 76%, advantageously of at least 85%, preferably of at least 90%, more preferably of at least 91%, 92%, 93%, 94%, 95%, 96%, 97% or 98%, and still more preferably of at least 99%, with respect to the nucleotide sequence shown in said SEQ ID NO: 1 and it encodes a peptide with QS inhibitory activity. In a specific embodiment, the polynucleotide of the invention is a polynucleotide the nucleotide sequence of which has a degree of identity of at least 76% with respect to the nucleotide sequence shown in said SEQ ID NO: 1 and it encodes a peptide with QS inhibitory activity. In another specific embodiment, the polynucleotide of the invention is a polynucleotide the nucleotide sequence of which has a degree of identity of at least 90% with respect to the nucleotide sequence shown in said SEQ ID NO: 1 and it encodes a peptide with QS inhibitory activity. In another specific embodiment, the polynucleotide of the invention is a polynucleotide the nucleotide sequence of which has a degree of identity of at least 99% with respect to the nucleotide sequence shown in said SEQ ID NO: 1 and it encodes a peptide with QS inhibitory activity.

The polynucleotide of the invention can be found as such or forming part of a gene construct, hereinafter gene construct of the invention, comprising said polynucleotide of the invention.

The gene construct of the invention can incorporate, in an operatively bound manner, a regulatory sequence regulating expression of the polynucleotide of the invention, thereby constituting an expression cassette. As it is used in this description, the expression "operatively bound" means that the peptide of the invention, encoded by the polynucleotide of the invention, is expressed in the correct reading frame under control of the control or regulatory sequences controlling or regulating expression. Control sequences are sequences that control and regulate transcription and, where appropriate, translation of the peptide of the invention, and include promoter sequences, encoding sequences for transcriptional regulators, ribosome binding sequences (RBS) and/or transcription termination sequences. In a particular embodiment, said expression control sequence is functional in prokaryotic cells and organisms, for example, bacteria, etc., whereas in another particular embodiment said expression control sequence is functional in eukaryotic cells and organisms, for example, insect cells, plant cells, mammalian cells, etc. Advantageously, the construct of the invention further comprises a marker or gene encoding for a motif or for a phenotype which allows selecting the host cell transformed with said construct. The gene construct of the invention can be obtained by means of using techniques that are well-known in the state of the art (Sambrook et al., 2001).

The gene construct of the invention can be inserted in a suitable vector. Therefore, in another aspect the invention relates to a vector, such as a recombinant vector, hereinafter vector of the invention, comprising the polynucleotide of the invention or the gene construct of the invention. The vector will be chosen depending on the host cell in which it will subsequently be introduced. In a particular embodiment, the vector of the invention is an expression vector. By way of non-limiting illustration, the vector in which the polynucleotide of the invention is introduced can be a plasmid which may or may not be integrated into the genome of a host cell when introduced in said cell. Illustrative, non-limiting examples of vectors into which the polynucleotide of the invention or the gene construct of the invention can be inserted include plasmid pET28c(+). The vector of the invention can be obtained by conventional methods known by those skilled in the art (Sambrook et al., 2001). In a particular embodiment, said vector is a vector useful for transforming competent *Escherichia coli* cells (Example 3).

The vector of the invention can be used for transforming cells susceptible to being transformed by said vector. Said cells can be prokaryotic or eukaryotic cells. The vector of the invention can be used for transforming eukaryotic cells, such as yeasts, for example, *Pichia pastoris*, etc., or microalgae, for example, *Chlamydomonas reinhardtii*, etc., or prokaryotic cells, such as bacteria, for example, *E. coli*, etc.

Therefore, in another aspect the invention relates to a host cell, hereinafter cell of the invention, comprising a polynucleotide of the invention, a gene construct of the invention, am expression cassette provided by this invention, or a vector of the invention, and it is capable of expressing the protein of the invention, or a peptide of the invention (defined below), provided that said cell of the invention is not a bacterium of the genus *Tenacibaculum*. As it is used herein, the term "cell" refers to the smallest unit maintaining the fundamental properties of life and comprises prokaryotic, eukaryotic and mesokaryotic cells, as well as cells of unicellular organisms (e.g., bacteria) and multicellular organisms (e.g., animals, plants). Therefore, by way of illustration the cell of the invention can be a eukaryotic cell, such as, for example, a cell from plant tissue, a yeast, a microalga, etc., a prokaryotic cell, such as a bacterium, for example, *E. coli*, etc. Obtaining cells from plant tissues comprising a polynucleotide of the invention, a gene construct of the invention, an expression cassette provided by this invention, a vector of the invention, or a peptide of the invention (defined below) can be very interesting from various points of view, for example, to increase resistance to pathogenic bacteria, particularly, QS signal-producing bacteria. The cells of the invention can be obtained by conventional methods known by those skilled in the art (Sambrook et al., 2001). In a particular embodiment, said cell of the invention is a host cell transformed with a vector of the invention.

In another aspect, the invention relates to a transgenic non-human organism, hereinafter "transgenic organism of the invention," comprising, inserted in the genome thereof, a polynucleotide of the invention, a gene construct of the invention, an expression cassette provided by this invention or a vector of the invention, provided that said non-human organism is not a bacterium of the genus *Tenacibaculum*. The transgenic organism of the invention can be a plant, for example, of tobacco, potato, tomato, onion, cottonseed, flaxseed, coffee, cocoa, rubber, oak, chestnut, cherry, etc., a cereal, for example, corn, wheat, rice, barley, oatmeal, etc., or an animal, for example, zebrafish, salmon, rabbit, mouse, etc. Since the polynucleotide of the invention encodes a peptide with QS inhibitory activity, the transgenic organism of the invention will be resistant, or substantially more resistant than the corresponding non-transgenic organism that does not contain the polynucleotide of the invention inserted in the genome thereof, to infections caused by QS signal producing-organisms, for example, bacteria, and/or could cause a Quorum Quenching (QQ) process in response to a QS process. The transgenic organism of the invention can be obtained by conventional methods known by those skilled in the art (Sambrook et al., 2001); said methods include the use of gene guns or the use of bacteria or viruses as vectors for transferring the polynucleotide of the invention. Dong et al. (2001) describes obtaining tobacco and potato plants transformed with the sequence corresponding to a *Bacillus* sp. lactonase with activity on AHLs, so the transgenic organism of the invention can be obtained, for example, by means of the methods described in said publication.

2. Peptide of the Invention

In another aspect, the invention relates to a peptide, hereinafter "peptide of the invention," the amino acid sequence of which corresponds to the amino acid sequence encoded by the polynucleotide of the invention.

As it is used herein, the term "peptide" refers to an amino acid chain in which the amino acids are bound to one another by peptide bonds, regardless of their length, and includes both amino acid chains having 10 amino acids or fewer (identified in some publications as "oligopeptides") and amino acid chains having more than 10 amino acids, for example, more than 100 amino acids.

In a particular embodiment, the peptide of the invention comprises the amino acid sequence shown in SEQ ID NO: 2. The amino acid sequence shown in SEQ ID NO: 2 corresponds to the sequence encoded by the polynucleotide the nucleotide sequence of which is shown in SEQ ID NO: 1. Said peptide has QS inhibitory activity. The features of said QS inhibitory activity were mentioned above in relation to the polypeptide of the invention as well as the assays for identifying whether or not a given peptide has said QS inhibitory activity. Assays performed by the inventors have clearly shown that the peptide the amino acid sequence of which is shown in SEQ ID NO: 2, inhibits QS, such as signals mediated by AHLs, so it at least has lactonase activity and hydrolyzes AHLs (Example 3).

In another particular embodiment, the amino acid sequence of the peptide of the invention consists of the nucleotide sequence shown in SEQ ID NO: 2. Sometimes said peptide is referred to as "Aii20J" in this description.

In another particular embodiment, the peptide of the invention is a substantially homologous and functionally equivalent variant of the peptide the amino acid sequence of which is shown in SEQ ID NO: 2.

In the sense used in this description, a peptide is "substantially homologous" to the peptide of SEQ ID NO: 2 when its amino acid sequence has a degree of identity with respect to the amino acid sequence shown in SEQ ID NO: 2 of at least 76%, advantageously of at least 85%, preferably of at least 90%, more preferably of at least 91%, 92%, 93%, 95%, 96%, 97% or 98%, and still more preferably of at least 99%. The degree of identity between two amino acid sequences can be determined by conventional methods, for example, by means of standard sequence alignment algorithms known in the state of the art, such as BLAST, for example (Altschul S. F. et al. 1990). By way of illustration, a peptide substantially homologous to the peptide the nucleotide sequence of which comprises or consists of the amino acid sequence shown in SEQ ID NO: 2 can be constructed based on the amino acid sequence shown in said SEQ ID NO: 2 by means of the introduction of, for example, amino acids constituting conservative or non-conservative substitutions with respect to the amino acids present in the amino acid sequence shown in SEQ ID NO: 2. Other illustrative examples of possible modifications include the addition of one or more amino acids at any of the ends (amino or carboxyl ends), the insertion of one or more amino acids in the sequence, or the deletion of one or more nucleotides at any end or within the sequence.

In the sense used in this description, a peptide is "functionally equivalent" to the peptide the amino acid sequence of which comprises or consists of the amino acid sequence shown in SEQ ID NO: 2 when it has QS inhibitory activity. The inhibitory activity of the peptide functionally equivalent to the peptide the amino acid sequence of which comprises or consists of the amino acid sequence shown in SEQ ID NO: 2 can be determined by conventional methods of determining said QS inhibitory activity (e.g., inhibitory activity of signals mediated by AHLs, AIPs, AI-2 and/or AI-3), such as those methods mentioned above.

In a particular embodiment, the peptide of the invention is a substantially homologous and functionally equivalent variant thereof, i.e., it is a peptide the amino acid sequence of which has a degree of identity of at least 76%, advantageously of at least 85%, preferably of at least 90%, more preferably of at least 91%, 92%, 93%, 94%, 95%, 96%, 97% or 98%, and still more preferably of at least 99%, with respect to the amino acid sequence shown in said SEQ ID NO: 2 and has QS inhibitory activity. In a specific embodiment, the peptide of the invention is a peptide the amino acid sequence of which has a degree of identity of at least 76% with respect to the amino acid sequence shown in said SEQ ID NO: 2 and has QS inhibitory activity. In another specific embodiment, the peptide of the invention is a peptide the amino acid sequence of which has a degree of identity of at least 93% with respect to the amino acid sequence shown in said SEQ ID NO: 2 and has QS inhibitory activity. In another specific embodiment, the peptide of the invention is a peptide the amino acid sequence of which has a degree of identity of at least 99% with respect to the amino acid sequence shown in said SEQ ID NO: 2 and has QS inhibitory activity.

One skilled in the art will understand that the amino acid sequences referred to in this description can be chemically modified, for example, by means of chemical modifications that are physiologically relevant, such as, phosphorylation, acetylation, etc.

Likewise, one skilled in the art will understand that included among said substantially homologous and functionally equivalents variants of the peptide the amino acid sequence of which is shown in SEQ ID NO: 2 are the peptide fragments that meet such conditions.

The peptide of the invention can be found as such or forming part of a fusion protein, which constitutes an additional aspect of the present invention. Said fusion protein therefore comprises a polypeptide A comprising a peptide of the invention and a polypeptide B, where said polypeptide B is a polypeptide other than said polypeptide A. Polypeptide B can be bound to any end of polypeptide A. Therefore, in a particular embodiment the amino-terminal end of polypeptide B is bound to the carboxyl-terminal end of polypeptide A, whereas in another particular embodiment the carboxyl-terminal end of polypeptide B is bound to the amino-terminal end of polypeptide A. Both polypeptides A and B can be bound directly to one another or through a linker peptide between said polypeptides A and B. The fusion protein can be obtained by conventional methods known by those skilled in the art, for example, by means of the expression of a polynucleotide comprising the nucleotide sequence encoding said fusion protein in suitable host cells. Polypeptide A comprises a peptide of the invention, the features of which have already been mentioned and are incorporated herein by reference. In a particular embodiment, the fusion protein of the invention has QS inhibitory activity, particularly inhibitory activity of QS signals mediated by AHLs, more specifically lactonase activity for hydrolyzing AHLs. Polypeptide B is a polypeptide "other than" polypeptide A, i.e., it is a polypeptide that is not polypeptide A; in this sense, in a particular embodiment polypeptide B is a peptide other than a peptide of the invention, whereas in another particular embodiment polypeptide B is a peptide of the invention but other than the specific peptide of the invention comprised in polypeptide A in a given fusion protein of the invention. Virtually any polypeptide can be used as polypeptide B in the fusion protein of the invention, provided that it meets the condition of being one other than polypeptide A. Illustrative, non-limiting examples of peptides that can be used as polypeptide B in the present invention include peptides useful for isolating and/or purifying proteins, etc. Therefore, in a particular embodiment said polypeptide B is a peptide useful for isolating and/or purifying proteins. Generally, said peptide useful for isolating and/or purifying proteins will be located in a region of the fusion protein of the invention that does not adversely affect the functionality of the peptide of the invention. Virtually any peptide that can be used for isolating and/or purifying a fusion protein (generically referred to as "tag peptides" or "tags") can be present in said fusion protein of the invention. By way of non-limiting illustration, said peptide useful for isolating and/or purifying a protein, such as a fusion protein, can be, for example, an arginine tag (Arg-tag), a histidine tag (His-tag), FLAG-tag, Strep-tag, an epitope susceptible to being recognized by an antibody, such as c-myc-tag, etc. In a particular and preferred embodiment of said fusion protein, said polypeptide B comprises a polyhistidine tag.

Assays performed by the inventors have clearly shown that the peptide of the invention, particularly the peptide the amino acid sequence of which comprises or consists of the sequence shown in SEQ ID NO: 2, is stable under given conditions. In the sense used in this description, the term "stable" refers to the capacity of the peptide of the invention to maintain its QS inhibitory activity under given conditions, for example, pH, proteinases, among others, and which furthermore lacks activity against β-lactam antibiotics and β-lactamase inhibitors. Therefore, it has been observed that in addition to having broad-spectrum lactonase activity, degrading AHLs with side chains comprised between 4 and 14 carbon atoms, both oxo- or hydroxy-substituted and unsubstituted, said peptide of the invention is resistant to pH in the range comprised between 3 and 9, is proteinase K- and chymotrypsin-resistant, and does not interact with β-lactam antibiotics (e.g., penicillin G, methicillin, amoxicillin, ampicillin, cefalotin, cefaclor, cefoxitin, ceftriaxone, cefoperazone, imipenem and meropenem) or with β-lactamase inhibitors (e.g., sulbactam and clavulanic acid), as seen in Example 3.

The stability of a peptide can be determined using various assays known by those skilled in the art. Some of said assays are based on determining the conservation (or loss) of the activity of the peptide under given conditions. By way of non-limiting illustration, the stability of a peptide can be determined by means of the assays mentioned in Example 3.

The peptide of the invention can be obtained by conventional methods known by those skilled in the art. Although said peptide of the invention can be isolated from an organism producing same, e.g., *Tenacibaculum* sp. strain 20J (CECT 7426), in a particular and preferred embodiment said peptide of the invention can be obtained by methods based on recombinant DNA technology.

Therefore, in another aspect the invention relates to a method for obtaining a peptide of the invention that comprises culturing a cell of the invention under conditions that allow the production of said peptide and, if desired, recovering said peptide from the culture medium. The conditions for optimizing the culture of said cell will depend on the cell used. One skilled in the art knows such conditions. The method for producing the peptide of the invention optionally includes the isolation and purification of said peptide of the invention.

3. Uses

Due to the QS inhibitory activity of the peptide of the invention, the polynucleotide of the invention, the vector of the invention, the cell of the invention, the transgenic organism of the invention, or the peptide of the invention have many potential uses in different sectors of the art, among which are included the food sector, pharmaceutical sector and agricultural sector.

Generally, for the administration and/or use thereof, the peptide of the invention, or the polynucleotide of the invention, or the vector of the invention, or the cell of the invention, or the transgenic organism of the invention, will be combined with a suitable vehicle.

Therefore, in another aspect the invention relates to a composition, hereinafter composition of the invention, comprising a polynucleotide of the invention, a vector of the invention, a cell of the invention, a transgenic organism of the invention, or a peptide of the invention.

For the sake of simplicity, reference will sometimes be made in this description to the polynucleotide of the invention, the vector of the invention, the cell of the invention, the transgenic organism of the invention, or the peptide of the invention with the generic expression "active component of the invention."

The features of the active component (polynucleotide, vector, cell, transgenic organism, or peptide of the invention) in the composition of the invention have already been defined above and are incorporated herein by reference. In a particular embodiment, the active component of the invention, present in the composition of the invention, is selected from the group consisting of a polynucleotide of the invention, a vector of the invention, a cell of the invention and a peptide of the invention, preferably a polynucleotide of the invention or a peptide of the invention.

As previously mentioned, the active component of the invention can be present in a vehicle suitable for the administration and/or use thereof. Generally, said vehicle will be chosen depending on the use for which the active component of the invention is intended and on the dosage form thereof. Nevertheless, in a particular embodiment the vehicle in which the active component of the composition of the invention can be present is a vehicle selected from:

a vehicle suitable for food;

a pharmaceutically acceptable vehicle; and an agriculturally acceptable vehicle.

3.1 Uses in the Food Sector

In a particular embodiment, the composition of the invention comprises an active component of the invention together with a vehicle suitable for food.

Therefore, according to this particular embodiment the composition of the invention is a food product. In the sense used in this description, the term "food product" includes any substance or product of any type that is solid or liquid, natural or transformed, which due to its features, uses, components, preparation and state of preservation, is susceptible to being commonly or suitably used for any of the following purposes: a) for normal human or animal nutrition or as components having no nutritional value; or b) as dietary products or additives, in special cases of human or animal food. Likewise, said term also includes natural materials or feeds and prepared products of any origin which, separately or duly mixed with one another, are suitable for animal food. As it is used herein, the term "food product" also includes nutraceutical compositions, i.e., compositions suitable for use in humans or animals comprising one or more natural products with therapeutic action or providing a benefit for health or which have been associated with the prevention or reduction of diseases, for example, probiotic bacteria, etc., and includes dietary supplements presented in a non-food matrix (e.g., capsules, powder, etc.) of a concentrated bioactive natural product normally present (or lacking) in foods and which, when taken at a dose exceeding that existing in those foods has a favorable effect on health that is greater than normal food could have. A food ready for consumption is a food that does not need to be diluted by means of, for example, an aqueous solution suitable for consumption. In theory, the ingredients present in a food ready for consumption are balanced and additional ingredients do not need to be added to the food to make them ready for consumption, as is considered by one skilled in the art. A concentrated food is a food in which one or more ingredients are present at a higher concentration than it is in a food ready for consumption, so for use thereof it must be diluted by means of, for example, an aqueous solution suitable for consumption. Illustrative, non-limiting examples, of foods provided by this invention include both food products intended for human consumption, and feeds and concentrated products for animal food, such as feeds and food concentrates intended for use in aquaculture or in any animal, whether said animal is a domestic or wild production animal, such as dogs, cats, bovines, ovines, suidae, equines, etc.

The use of a polynucleotide of the invention, a vector of the invention, a cell of the invention, a transgenic organism of the invention, or a peptide of the invention in the preparation of a food product, constitutes an additional aspect of this invention. In a particular embodiment, said food product is a substance or product susceptible to being used in foods, feeds, food additives, dietary supplements, nutraceutical compositions, etc., for both human and animal food.

3.2 Uses in the Pharmaceutical Sector

In another particular embodiment, the composition of the invention is a pharmaceutical composition comprising, in addition to the active component present in the composition of the invention, a pharmaceutically acceptable vehicle. Compositions of this type are suitable for administration of the active component present in the composition of the invention to a subject. Generally, said pharmaceutically acceptable vehicle will be chosen depending on the nature of the active component (e.g., polynucleotide of the invention, vector of the invention, cell of the invention or peptide of the invention), of the chosen presentation form, for example, solid (e.g., tablets, capsules, coated tablets, granules, suppositories, etc.) or liquid (e.g., solutions, suspensions, emulsions, etc.) and on the chosen administration route, for example, oral, parenteral (e.g., intramuscular, subcutaneous, intravenous, etc.), rectal, etc. In each case, the pharmaceutically acceptable excipients suitable for the chosen pharmaceutical dosage form and administration route will be chosen. Information about excipients suitable for the formulation of pharmaceutical compositions intended for administration by oral, parenteral or rectal route, and about the production of said pharmaceutical compositions can be found in the book entitled "Tratado de Farmacia Galénica," by C. Faulí i Trillo, $10^{th}$ Edition, 1993, Luzán 5, S.A. de Ediciones.

In another aspect, the invention relates to the use of a polynucleotide of the invention, a vector of the invention, a cell of the invention, a transgenic organism of the invention, or a peptide of the invention in the preparation of a medicament for the prevention and/or treatment of a bacterial infection. Expressed in a different way, according to this aspect the invention relates to an active component of the invention (i.e., a polynucleotide of the invention, a vector of the invention, a cell of the invention, a transgenic organism of the invention, or a peptide of the invention) for use in the prevention and/or treatment of a bacterial infection. In a particular embodiment, the bacterium causing said bacterial infection is a QS signal-producing bacterium. In a specific embodiment, said QS signals produced by the bacterium causing the infection comprise at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc. In another particular embodiment, the bacterium causing said bacterial infection is a QS signal-producing bacterium, wherein said QS signal does not comprise an AHL, but rather said QS signal comprises an AIP, an AI-2 and/or an AI-3, for example, a Gram-positive or Gram-negative bacterium. In a particular embodiment, said bacterium is *Escherichia coli*, an important human pathogen [see Example 4 in which the potential use of Aii20J in the control of *E. coli* expression is clearly shown]. In another particular embodiment, infections caused by QS signal-producing bacteria are due to biofilm formation. The biofilm-forming bacteria can be, but without being limited to, bacteria of the oral cavity such as the bacteria causing caries and periodontal disease, or bacteria colonizing the surfaces of medical implants or devices inserted in the organism, such as catheters, prostheses, etc. Therefore, in a particular embodiment the pharmaceutical composition of the invention is a dentifrice composition. In another particular embodiment, the pharmaceutical composition is intended for preventing biofilm formation or for eliminating biofilms already formed on medical devices or implants such as catheters, prostheses, etc.

The pharmaceutical composition provided by this invention can also contain, if desired, one or more antibacterial agents, provided that they are not incompatible with the active component of the invention present in the composition of the invention. The combination of the active component of the invention with antibiotics can be a very interesting strategy in the treatment of bacterial diseases caused by multiresistant bacteria.

The pharmaceutical composition provided by this invention can be applied or administered to a subject in need of prevention and/or treatment. As it is used herein, the term "subject" refers to a member of an animal species, preferably a mammal, and includes, but is not limited to domestic animals, primates and humans; preferably, the subject is a male or female human being, of any age or race.

In another aspect, the invention relates to a method for the prevention and/or treatment of a bacterial infection in a subject, which comprises administering to a subject in need of treatment an effective amount of a pharmaceutical composition provided by this invention or of an active component of the invention. In a particular embodiment, said bacterial infection is caused by a QS signal-producing bacterium. In a specific embodiment, said QS signals produced by the bacterium causing the infection comprise at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc. In another particular embodiment, the bacterium causing said bacterial infection is a QS signal-producing bacterium, wherein said QS signal does not comprise an AHL, but rather said QS signal comprises an AIP, an AI-2 and/or an AI-3, for example, a Gram-positive or Gram-negative bacterium. In a particular embodiment, said bacterium is *Escherichia coli*, an important human pathogen [see Example 4 in which the potential use of Aii20J in the control of *E. coli* expression is clearly shown]. In another particular embodiment, infections caused by QS signal-producing bacteria are due to biofilm formation (e.g., bacteria of the oral cavity such as the bacteria causing caries and periodontal disease, bacteria colonizing the surfaces of medical implants or devices inserted in the organism, such as catheters, prostheses, etc.).

The features of the pharmaceutical composition provided by this invention and of the active components of the invention have already been defined above and are incorporated herein by reference. Likewise, the features of the presentation form and dosage form of the pharmaceutical composition provided by this invention, as well as of the active components of the invention, were already mentioned above and are incorporated by reference.

3.3 Uses in the Agricultural Sector

In another particular embodiment, the composition of the invention is an agricultural composition comprising, in addition to the active component present in the composition of the invention, an agriculturally acceptable vehicle. Compositions of this type are suitable for the administration of the active component present in the composition of the invention to plants. Generally, said agriculturally acceptable vehicle will be chosen depending on the nature of the active component, on the chosen presentation form, for example, solid or liquid, etc. In each case, agriculturally acceptable ingredients suitable for the chosen dosage form will be chosen. Virtually any agriculturally acceptable vehicle can be used in the preparation of the agricultural composition provided by this invention; nevertheless, in a particular embodiment said agriculturally acceptable vehicle comprises a fertilizer, such as a solid or liquid fertilizer, for example. Illustrative, non-limiting examples of said solid fertilizers include NPK-type solid fertilizers, etc. Alternatively, any liquid fertilizer with a pH comprised between 3 and 9, in which the peptide of the invention maintains its QS inhibitory activity can be used; illustrative, non-limiting examples of said liquid fertilizers include fertilizers based on fulvic acids, liquid fertilizers with a different NPK composition, such as the 16:2:4 mixtures, 20:5:0 mixtures, etc., or various types of fertilizers in drops with an NPK composition of 8:9:9, 16:4:4, etc.

The agricultural composition provided by this invention can be obtained by conventional methods by means of mixing the active component with the agriculturally acceptable vehicle.

The agricultural composition provided by this invention can be used in the prevention and/or treatment of a bacterial infection in plants. In a particular embodiment, the bacterium causing said bacterial infection is a QS signal-producing bacterium. In a specific embodiment, said QS signals produced by the bacterium causing the infection comprise at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc.

The agricultural composition provided by this invention can also contain, if desired, one or more antibacterial agents, provided that they are not incompatible with the active component of the invention present in the composition of the invention.

The agricultural composition provided by this invention can be presented in any presentation form suitable for administration or application to the plant or to the soil surrounding the plants, for example, in solid or liquid form. Liquid presentation forms are suitable for being sprayed on the soil, plant or plant material in general, or for creating a bath in which the plants or plant material are immersed.

The agricultural composition provided by this invention can be applied by any conventional method. In a particular embodiment, the composition of the invention is applied by means of spraying on the soil, the plant or plant material, or by means of immersing the plant or plant material in a bath containing the composition of the invention. Alternatively, plant seeds can be subjected to a pelleting treatment with the agricultural composition provided by this invention.

In another aspect, the invention relates to a method for controlling a bacterial disease in a plant, which comprises contacting said plant with a peptide of the invention, wherein said bacterial disease is caused by a QS signal-producing bacterium, under conditions that allow controlling said bacterial disease. In a particular embodiment, the peptide of the invention is formulated in an agricultural composition provided by this invention and said composition is applied on the plant to be treated. In another particular embodiment, the peptide of the invention is contacted with the QS signal-producing bacterium under conditions that allow the contact of and interaction between the peptide of the invention and the QS signals produced by the bacterium causing the infection. One skilled in the art will understand that the peptide of the invention must be added in an amount that is sufficient for obtaining beneficial or desired results, i.e., in the amount that is suitable for palliating, improving, stabilizing, reversing, holding back or delaying progression of stages of diseases caused by bacteria in plants. Said amount can be administered in a single application or in several applications. Likewise, one skilled in the art knows, or can identify, the administration conditions of the peptide of the invention that allow controlling said bacterial disease.

In another aspect, the invention relates to a method for controlling a bacterial disease in a plant, which comprises transforming said plant with a polynucleotide of the invention, or with a vector of the invention, wherein said bacterial disease is caused by a QS signal-producing bacterium. Obtaining plants transformed with the polynucleotide or vector of the invention is carried out by conventional methods of transforming plants, based, for example, on the use of suitable vectors, as well as on the methods described in, for example, Izquierdo, 1993 or Dong et al., 2011.

In another aspect, the invention relates to a method for controlling a bacterial disease in a plant comprising the use of a bacterium transformed with a polynucleotide of the invention or with a vector of the invention, wherein said bacterial disease is caused by a QS signal-producing bacterium.

In any of the three methods mentioned above for controlling a bacterial disease in a plant, the bacterial disease is caused by a QS signal-producing bacterium. In a specific embodiment, said QS signals produced by the bacterium causing the infection comprise at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc.

Illustrative, non-limiting examples of phytopathogenic bacteria include Gram-positive bacteria such as, for example, bacteria belonging to the genera *Clavibacter, Curtobacterium, Streptomyces*, etc., as well as Gram-negative bacteria such as, for example, bacteria belonging to the genera *Agrobacterium, Brenneria, Burkholderia, Erwinia, Gluconacetobacter, Pantoea, Pectobacterium, Pseudomonas, Xanthomonas, Xylella*, etc. In a particular embodiment, said phytopathogenic bacterium is a pathogenic Gram-negative bacterium of plants with QS and a bacterium producing any AHL such as, for example, Brenneria sp., *Burkholderia glumae, Erwinia amylovora, Erwinia carotovora, Gluconacetobacter diazotrophicus* (in sugar cane), *Pantoea ananatis, Pectobacterium atrosepticum, Pseudomonas syringae*, etc.

The agricultural composition provided by this invention can be applied or administered to a plant in need of controlling a bacterial disease. The expression "controlling a bacterial disease" in a plant refers to preventing and/or treating the bacterial disease, as well as to maintain control over a bacterial population at levels that do not cause damage to the plant or harmful effects for subjects that feed from said plants. As it is used herein, the term "plant" includes any photosynthetic living being.

3.4 Quorum Quenching

In another aspect, the invention relates to the use of a polynucleotide of the invention, a vector of the invention, a cell of the invention, a transgenic organism of the invention or a peptide of the invention, for causing a quorum quenching (QQ) process in response to a QS process. In a particular embodiment, said use does not consist of a method of surgical or therapeutic treatment of the human or animal body.

Expressed in an alternative way, this inventive aspect relates to a method for causing a QQ process in response to a QS process, wherein said QS process is caused by a QS signal-producing bacterium, which comprises contacting said bacterium with a polynucleotide of the invention, a vector of the invention, a cell of the invention, a transgenic organism of the invention or a peptide of the invention, under conditions that allow causing said QQ process in response to said QS process. In a particular embodiment, said method does not consist of a method of surgical or therapeutic treatment of the human or animal body.

In the sense used in this description, the expression causing a "quorum quenching (QQ) process" in response to a QS process refers to the development of a QS process inactivation strategy. The features of the active components of the invention (polynucleotide, vector, cell, transgenic organism or peptide of the invention) have already been defined above and are incorporated herein by reference. One skilled in the art knows the conditions that allow contacting the QS signal-producing bacterium with the active component of the invention for causing said QQ process in response to said QS process; generally, said conditions include those in which the active component of the invention remains stable and maintains its activity.

In a particular embodiment, the QS signal-producing bacterium is a bacterium producing at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc.

A number of pathogenic bacteria of plants and animals, including humans, use a QS process based on different types of QS signals (e.g., AHLs, APIs, AI-2 and AI-3) to regulate the synthesis of virulence factors or to form biofilms. Therefore, interception of bacterial communication mediated by said QS signals is a promising method for the control of bacteria, particularly pathogenic QS signal-producing bacteria.

Accordingly, the polynucleotide of the invention, the vector of the invention, the cell of the invention, the transgenic organism of the invention and the peptide of the invention, can be used to intercept communication between QS signal-producing bacteria, thereby causing a QQ process, and to thereby control infections caused by said bacteria. Since QQ processes for the treatment of diseases caused by bacteria, particularly QS signal-producing bacteria, do not directly affect survival of the pathogenic bacterium, but rather expression of virulence factors, they do not seem to exert selective pressure on the bacterium, thereby preventing the onset of resistances, which is an important advantage.

3.5 QS Process Inhibition

In another aspect, the invention relates to the use of a polynucleotide of the invention, a vector of the invention, a cell of the invention, a transgenic organism of the invention or a peptide of the invention, for inhibiting a QS process, wherein said QS process is caused by a QS signal-producing bacterium. In a particular embodiment, said use does not consist of a method of surgical or therapeutic treatment of the human or animal body.

Expressed in another way, this inventive aspect relates to a method for inhibiting a QS process, wherein said QS process is caused by a QS signal-producing bacterium, which comprises contacting said bacterium with a polynucleotide of the invention, a vector of the invention, a cell of the invention, a transgenic organism of the invention or a peptide of the invention, under conditions that allow inhibiting said QS process. In a particular embodiment, said method does not consist of a method of surgical or therapeutic treatment of the human or animal body.

In the sense used in this description, the expression "inhibiting a QS process" includes inactivating the QS process as well as intercepting bacterial communication mediated by QS signals (e.g., AHLs, APIs, AI-2 and AI-3). This method is therefore a promising method for controlling bacteria, particularly pathogenic bacteria (e.g., of plants and animals, including humans) using a QS process based on different types of QS signals to regulate the synthesis of virulence factors or to form biofilms.

The features of the active components of the invention (polynucleotide, vector, cell, transgenic organism or peptide of the invention) have already been defined above and are incorporated herein by reference. One skilled in the art knows the conditions that allow contacting the QS signal-producing bacterium with the active component of the invention for inhibiting said QS process; generally, said conditions include those in which the active component of the invention remains stable and maintains its activity. In a particular embodiment, the QS signal-producing bacterium is a bacterium producing at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc.

Therefore, the polynucleotide of the invention, the vector of the invention, the cell of the invention, the transgenic organism of the invention and the peptide of the invention, can be used to inhibit a QS process caused by QS signal-producing bacteria and to thereby control infections caused by said bacteria.

3.6 QS Signal Degradation

In another aspect, the invention relates to an in vitro method for degrading a QS signal, wherein said QS signal is produced by a QS signal-producing bacterium, which comprises contacting a polynucleotide of the invention, a vector of the invention, a cell of the invention, a transgenic organism of the invention or a peptide of the invention, with said QS signal under conditions that allow degrading said QS signal.

In the sense used in this description, the expression "degrading a QS signal" includes hydrolyzing a QS signal, such as an AHL, an API, an AI-2 or an AI-3, such that said degraded QS signal can no longer perform the function of communication between bacteria for which it was intended; therefore, a bacterial population can be controlled intercepting the communication between its members by means of degrading signals responsible for said communication. Therefore, this method constitutes an alternative method for controlling bacteria, particularly pathogenic bacteria (e.g., of plants and animals, including humans) using a QS process based on different types of QS signals to regulate the synthesis of virulence factors or to form biofilms.

The features of the active components of the invention (polynucleotide, vector, cell, transgenic organism or peptide of the invention) have already been defined above and are incorporated herein by reference. One skilled in the art knows the conditions that allow contacting the QS signal with the active component of the invention for degrading said QS signal; generally, said conditions include those in which the active component of the invention remains stable and maintains its activity. In a particular embodiment, the QS signal-producing bacterium is a bacterium producing at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc.

Therefore, the polynucleotide of the invention, the vector of the invention, the cell of the invention, the transgenic organism of the invention and the peptide of the invention can be used for degrading a QS signal produced by a QS signal-producing bacterium, and to thereby control infections caused by said bacteria.

3.7 Modulating the Signaling Activity of AHLs

In another aspect, the invention relates to an in vitro method for modulating the signaling activity of an AHL, which comprises contacting a polynucleotide of the invention, a vector of the invention, a cell of the invention, a transgenic organism of the invention or a peptide of the invention, with said AHL, under conditions that allow modulating the signaling activity of said AHL.

In the sense used in this description, the expression "modulating the signaling activity of an AHL" includes completely or partially degrading or hydrolyzing an AHL, such that said completely or partially degraded or hydrolyzed AHL can no longer perform the function of communication between bacteria for which it was intended; therefore, a QS signal-producing bacterial population can be controlled, wherein said QS signals comprise one or more AHLs, intercepting communication between the members thereof by means of degradation or hydrolysis of signals (AHLs) responsible for said communication. Therefore, this method constitutes an alternative method for controlling bacteria, particularly pathogenic bacteria (e.g., of plants and animals, including humans) using a QS process based on the production of AHLs to regulate the synthesis of virulence factors or to form biofilms.

The features of the active components of the invention (polynucleotide, vector, cell, transgenic organism or peptide of the invention) have already been defined above and are incorporated herein by reference. One skilled in the art knows the conditions that allow contacting the active component of the invention with the AHL; generally, these conditions include those in which the active component of the invention remains stable and maintains its activity.

In a particular embodiment, said AHL is an unsubstituted AHL, such as, for example, C4-HSL, C6-HSL, C8-HSL, C10-HSL, C12-HSL or C14-HSL, or a mixture thereof. In another particular embodiment, said AHL is an oxo- or hydroxy-substituted AHL, such as, for example, OC6-HSL, OC12-HSL, etc., or mixtures thereof.

Therefore, the polynucleotide of the invention, the vector of the invention, the cell of the invention, the transgenic organism of the invention and the peptide of the invention, can be used for modulating the signaling activity of an AHL, produced by a QS signal-producing bacterium, wherein said QS signals comprise one or more AHLs, and to thereby control infections caused by said bacteria.

3.8 Inhibiting Bacterial Biofilm Formation

In another aspect, the invention relates to the use of a polynucleotide of the invention, a vector of the invention, a cell of the invention, a transgenic organism of the invention or a peptide of the invention, for inhibiting bacterial biofilm formation ex vivo or in vitro, wherein said bacterial biofilm is produced by a QS signal-producing bacterium. Expressed in another way, this inventive aspect relates to an in vitro or ex vivo method for inhibiting bacterial biofilm formation, wherein said bacterial biofilm is produced by a QS signal-producing bacterium, which comprises contacting said polynucleotide of the invention, vector of the invention, cell of the invention, transgenic organism of the invention or peptide of the invention, with said bacterium, under conditions that allow inhibiting said bacterial biofilm formation.

In the sense used in this description, the expression "inhibiting bacterial biofilm formation" refers to preventing or hindering QS signal-producing bacteria from being able to form a biofilm. As is known, biofilm formation is a process controlled by QS phenomena, mediated by QS signals such as AHLs, APIs, AI-2 and/or AI-3, and has an important economic and clinical impact. Many of said biofilms are closely related to infectious bacterial processes, both in plants and in animals, including humans. Generally, the biofilm-forming bacteria are highly resistant to antibiotics and can adhere to foods or substances in contact with them, causing both hygiene problems and possible foodborne diseases and, finally, large economic losses. Furthermore, they are often located on the surface of the medical implants or in devices inserted in the organism. They can also be formed in areas of the body that are exposed to the air; particularly, in wounds and in the pleura. One of the most complex and most clinically relevant biological biofilms is dental plaque. The role of QS molecule AI-2 in biofilm formation based on the opportunistic pathogens *Staphylococcus aureus, S. epidermidis* and different *Streptococcus* species, including the strain involved in dental plaque formation, *S. mutans*, has been demonstrated. Furthermore, these biofilms contribute to biological surface contamination, mechanical blockage in conduits, drinkable water distribution systems, air conditioning systems, fire protection systems, etc. Finally, it is worth pointing out that they favor biofouling formation as they are the basis for the growth of other higher organisms on submerged surfaces, being a serious economic problem in the aquaculture and marine transport sectors. Therefore, this method is a promising method for controlling both biofilm formation and for controlling biofilm-producing bacteria by means of a process controlled by QS signals, particularly pathogenic bacteria (e.g., of plants and animals, including humans) that use a QS process based on different types of QS signals to form biofilms.

The features of the active components of the invention (polynucleotide, vector, cell, transgenic organism or peptide of the invention) have already been defined above and are incorporated herein by reference. One skilled in the art knows the conditions that allow contacting the bacterium forming biofilms by means of a process controlled by QS signals with the active component of the invention for inhibiting the formation of said bacterial biofilms; generally, said conditions include those in which the active component of the invention remains stable and maintains its activity. In a particular embodiment, the biofilm-forming bacterium is a QS signal-producing bacterium, such as a bacterium producing at least one AHL. Illustrative, non-limiting examples of said AHLs include unsubstituted AHLs, such as, for example, C4-HSL, C6-HSL, C8-HSL, C10-HSL, C12-HSL or C14-HSL, as well as oxo- or hydroxy-substituted AHLs, such as, for example, OC6-HSL, OC12-HSL, etc.

Therefore, the polynucleotide of the invention, the vector of the invention, the cell of the invention, the transgenic organism of the invention and the peptide of the invention, can be used to inhibit bacterial biofilm formation controlled by means of QS signals caused by QS signal-producing bacteria, and to thereby control infections caused by said bacteria.

The following examples illustrate the invention and must not be considered in a limiting sense thereof.

Example 1

Identification of Aii20J, Gene Responsible for QQ Activity in *Tenacibacullum* sp. Strain 20J 1.1 Construction of a Fosmid Genomic Library and Functional screening For the purpose of identifying and cloning the gene or genes responsible for the activity of degrading AHLs of *Tenacibaculum* sp. strain 20J (CECT 7426), a genomic library was constructed using the CopyControl™ Fosmid Library Production Kit (Epicentre, Madison, Wis.) with the pCC2FOS vector according to the manufacturer's protocol.

*Tenacibaculum* sp. strain 20J DNA was extracted by means of the Wizard Genomic DNA Purification kit (Promega, Madison, Wis.) according to the manufacturer's instructions. The DNA (2.5 µg) was randomly fragmented by means of pipetting (50-100 times) with a 200 µL pipette tip. The fragmented DNA was treated enzymatically to repair and generate phosphorylated and blunt ends. 40 kb fragments were then selected by means of pulsed-field gel electrophoresis (PFGE) and were ligated into the linearized and dephosphorylated fosmid pCC2FOS. *Escherichia coli* DH10β cells were then transformed by means of lambda phage. The bacterial cells were seeded in plates with Luria-Bertani (LB) medium in the presence of the antibiotic chloramphenicol at a concentration of 12.5 μg/ml and were incubated at 37° C. for 24 h. The *E. coli* DH10β colonies transfected with the fosmid were picked by robotic means (Genetix Q-bot) and were distributed in 96-well microtiter plates containing 150 μL of LB plus chloramphenicol and glycerol which was added for the correct freezing thereof. The genomic library consisted of 6,912 clones distributed in 72 96-well microtiter plates and was preserved in a freezer at −80° C. until use.

Functional screening of the genomic library of *Tenacibaculum* sp. strain 20J was performed to detect the gene or genes responsible for the activity of degrading AHLs of that strain. The functional screening for a short signal (N-hexanoyl-L-homoserine lactone, C6-HSL) and a long signal (N-decanoyl-L-homoserine lactone, C10-HSL) was performed simultaneously for the purpose of increasing the possibilities of identifying the enzyme or enzymes responsible for QQ activity, using a modification of the agar plate screening technique described in Romero et al., 2011. Each 96-well microtiter plate of the genomic library was copied to a new plate with 50 μL of LB liquid supplemented with chloramphenicol (12.5 μg/ml), 2 μL/ml of the autoinduction solution contained in the CopyControl™ Fosmid Library Production Kit (Epicentre, Madison, Wis.), and C6-HSL at a concentration of 12 μg/ml. The autoinduction solution induces the high copy number of the fosmid in each cell, which allows increasing expression of the genes of the insert. The plates were incubated at 37° C. to allow the possible positive clones to degrade the signal. After 24 h, 10 μL aliquots were taken from each well to new microtiter plates, which were irradiated with UV light for 1 hour to kill *E. coli* DH10P cells. Then 50 μL of a 1/5 dilution (v/v) of a 24 h culture of *C. violaceum* CV026 were added to detect C6-HSL degradation and of *C. violaceum* VIR07 to detect C10-HSL degradation, in 0.2% soft LB agar supplemented with the antibiotic kanamycin at a concentration of 25 μg/ml, and they were incubated at 30° C. for 24 h to observe violacein production. The wells of the plates are violet-colored due to production of violacein pigment, except the wells containing the gene or genes capable of degrading the AHLs, which are positive clones.

It was possible to identify a single positive clone that inhibited AHL activity, preventing violacein formation in the well (FIG. 1). This positive clone was in plate 13, coordinate E2, so it was referred to as clone 13-E2, showing inhibitory activity in the bioassay against both C6-HSL and C10-HSL.

The activity of the only positive clone identified in the functional screening (clone 13-E2, FIG. 1) of the genomic library was verified, once transferred to a culture in a Petri dish with chloramphenicol to verify clone purity, by means of performing a plate bioassay by means of wells identical to that used for identifying bacteria with QQ activity against AHLs in earlier works (Romero et al., 2011). The positive clone was inoculated in Eppendorf tubes with 500 μL of LB liquid supplemented with chloramphenicol (12.5 μg/ml) and autoinduction solution (2 μL/ml). It was incubated under stirring at 200 rpm and 37° C. After 24 hours, 20 μL of a stock solution of each AHL (C6 and C10-HSL) were added in order to render a final concentration of 2 μg/ml, and they were incubated again for 24 h at 37° C. and at 200 rpm. To detect QQ activity, 100 μL of the supernatant were taken after centrifuging the culture for 5 min at 10,000 rpm and added to wells made in LB plates covered with 5 ml of a 1/100 dilution of a 24-hour culture of the corresponding biosensor strains *C. violaceum* CV026 and *C. violaceum* VIRO7 in semi-solid LB (0.8% agar). Eppendorf tubes of non-inoculated LB or of LB inoculated with negative clones without QQ activity in genomic library screening were used as negative controls. The plates were incubated for 24 h at 30° C. for the subsequent observation of violacein production.

HPLC-MS (High-Performance Liquid Chromatography-Mass Spectrometry) was then used to verify if the positive clone from the fosmid genomic library active against AHL, clone 13-E2, presented signal degradation activity. To that end, the crude cell extract (CCE) of the clone with QQ activity of *E. coli* DH10β was obtained from a 24 h culture in 15 ml of LB supplemented with chloramphenicol and autoinduction solution. The culture was centrifuged for 5 min at 10,000 rpm to separate the biomass from the culture medium. The pellet was washed with 15 ml of phosphate-buffered saline (PBS) pH 6.5, resuspended in another 5 ml of the same buffer, sonicated by means of 30 s pulses for 5 min on ice and centrifuged at 12,000 rpm for 30 min at 4° C. The supernatant was filtered (0.22 μm) and the obtained CCE was stored at 4° C. for subsequent use.

500 μL aliquots of CCE were used for intercepting C6-HSL or C10-HSL signals which were added at a concentration of 2 μg/ml and incubated for 24 h at 22° C. and 200 rpm. An aliquot of the reaction was acidulated to verify recovery of the lactone ring. Organic extraction of the reaction mixtures was subsequently performed, for which purpose extraction was performed three times with the same volume of ethyl acetate (500 μL). The solvent was recovered and evaporated by means of nitrogen flow in a 50° C. bath and the obtained dry extract was resuspended in 400 μL of acetonitrile for subsequent analysis and quantification of the concentration of the remaining signal by HPLC-MS according to the methodology previously described (Romero et al., 2011). PBS and a CCE of *E. coli* DH10β without fosmid supplemented with the same amount of C6-HSL or C10-HSL signals and processed and extracted organically in the same manner were used as controls.

Figure 2:
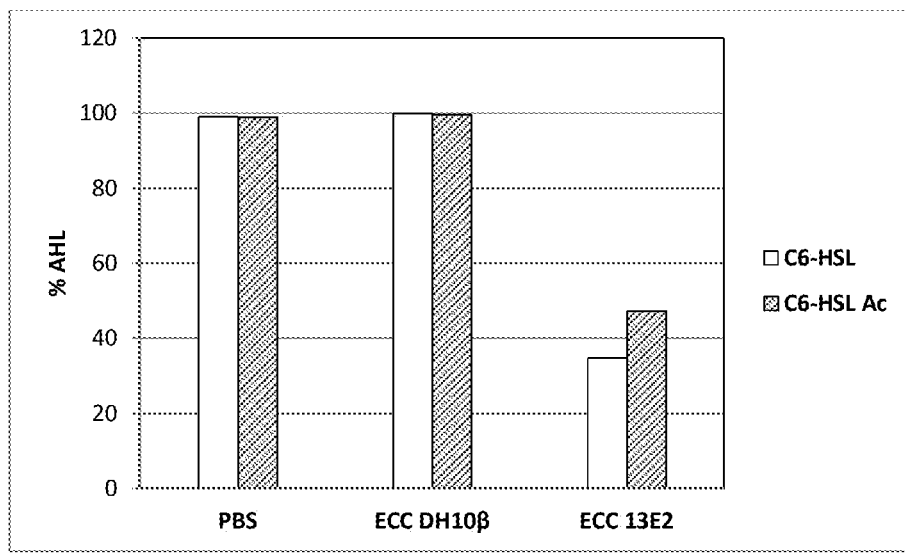
FIG. 2 shows HPLC-MS analysis of C6-HSL degradation after 24 hours by positive clone 13-E2 cell extracts (CCE 13E2). Controls: PBS and *E. coli* DH10β without fosmid (CCE DH10β). It was acidulated at pH 2 to recover the lactone ring (shaded bars).
Figure 3:
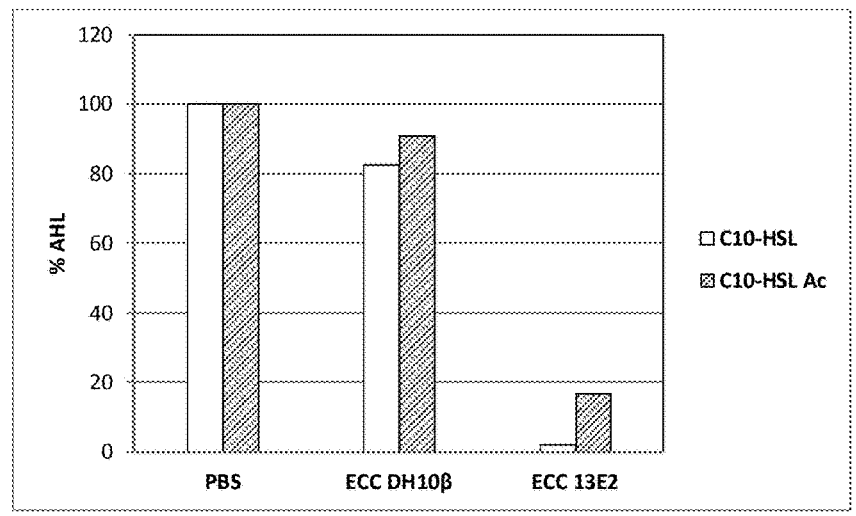
FIG. 3 shows HPLC-MS analysis of C10-HSL degradation after 24 hours by positive clone 13-E2 cell extracts (CCE 13E2). Controls: PBS and *E. coli* DH10β without fosmid (CCE DH10β). It was acidulated at pH 2 to recover the lactone ring (shaded bars).

The positive clone of 13-E2, selected from the genomic library of *Tenacibaculum* sp. strain 20J, was capable of significantly reducing the concentration of both AHLs quantified by HPLC-MS in comparison with the controls (FIGS. 2 and 3), confirming the presence of an enzyme-encoding gene capable of degrading AHL in this clone, having, like *Tenacibaculum* sp. strain 20J, greater activity against C10-HSL. In both cases, it was possible to recover part of the AHL activity after acidification of the medium, suggesting that the gene responsible for the activity of degrading AHL of clone 13-E2 could have lactonase activity.

1.2 Identification of the Sequence of Aii20J in Positive Clone 13-E2

Since the fosmid of *E. coli* positive clone 13-E2, the QQ activity of which for the two assayed AHL sizes was confirmed both in bioassay and by HPLC-MS, contained an insert of the *Tenacibaculum* sp. strain 20J genome of about 40 kb in length, a detailed genetic analysis of this insert was necessary to identify the sequence responsible for the QQ activity of the clone. To that end, two complementary strategies were followed:

1. Pyrosequencing the fosmid insert of positive clone 13-E2 to obtain the complete sequence thereof and the search for sequences homologous to the enzymes degrading AHL known up until now; and 2. Constructing a second genomic library in which the fosmid insert of positive clone 13-E2 was fragmented and subcloned into the plasmid to allow the unequivocal functional identification of the sequence responsible for QQ activity.

1.2.1 Pyrosequencing the Fosmid Insert of Active Clone 13-E2

As a first approach to the identification of the gene responsible for QQ activity, the insert of positive clone 13-E2 obtained in the genomic library screening was sequenced using the Roche GS-FLX sequencer. To that end, the fosmid (150 ng/µL) of the positive clone was extracted following the Fosmid Max™ DNA Purification Kit protocol (Epicentre, Madison, Wis.). The obtained sequences were analyzed by means of the following computer tools: NCBI's BLASTX and CD-Search (Conserved Domain Search). The sequences were aligned and were assembled with the Phrap program, obtaining a sequence of 39,828 base pairs (bp). For the identification of ORFs of the fragment, a search was conducted in the 'nr' database available in NCBI, not being able to identify any gene with significant homology with known genes with QQ activity. It was possible, however, to identify 4 ORFs with high homology (greater than 70%) with genes of species from the *Cytophaga-Flavobacterium-Bacteroides* (CFB) cluster, confirming that the clone 13-E2 insert is from *Tenacibaculum* sp. strain 20J (CECT 7426), a member of the Bacteroidetes group. In the search for all the conserved domains in the 'cdd' database, a β-lactonase domain was detected at the end of the analyzed sequence of positive clone 13-E2. That entire zone of the sequence was translated and the start codon (ATG) and stop codon (TAA) of the enzyme were identified, obtaining a sequence having 861 nucleotides (SEQ ID NO: 1) encoding a peptide having 286 amino acids (SEQ ID NO: 2), having 31% identity at the amino acid level with *Bacillus* sp. AiiA lactonase (Table 1, Dong et al. 2000). This new lactonase sequence has been referred to as aii20J (autoinducer inhibitor of 20J).

1.2.2 Construction and Analysis of a Genomic Library of the Insert of Active Clone 13-E2

Simultaneously and for the purpose of unequivocally identifying the gene responsible for QQ activity based on the activity thereof, the 40 kb insert of positive clone 13-E2 was subcloned for the functional analysis of the fragments. To that end, a new genomic library was constructed from the fosmid insert of positive clone 13-E2 purified by means of the Fosmid Max™ DNA Purification Kit (Epicentre, Madison, Wis.). The extracted DNA was randomly fragmented by means of hydrolysis (hydroshearing), fragments between 3 and 5 kb were selected by means of electrophoresis and they were enzymatically treated to generate phosphorylated and blunt ends. These fragments were ligated into the high copy number pBluescript II KS (+) plasmid and then *E. coli* DH10β was transformed by means of electroporation. The transformants were seeded in LB plate with 200 µg/ml of ampicillin, 80 µg/ml of X-Gal and 1 mM of isopropyl-β-D-thiogalactopyranoside (IPTG) at 37° C. After 24 h the white recombinant colonies were picked by robotic means (Genetix Q-bot) and seeded in 10 96-well microtiter plates with 150 µL of solid LB (1.2% agar) plus ampicillin.

Similarly to the analysis of the first genomic library, functional screening of the microtiter plates of the gene library was performed to detect clones capable of degrading AHLs. The bioindicator strain *C. violaceum* VIR07 was used for analysis of C10-HSL degradation, with a concentration of 12 µg/ml of the signal. The method was the same as in the first genomic library, but in this subcloned library the antibiotic ampicillin at a concentration of 200 µg/ml and 1 mM IPTG were used to induce expression of the insert genes.

Figure 4:
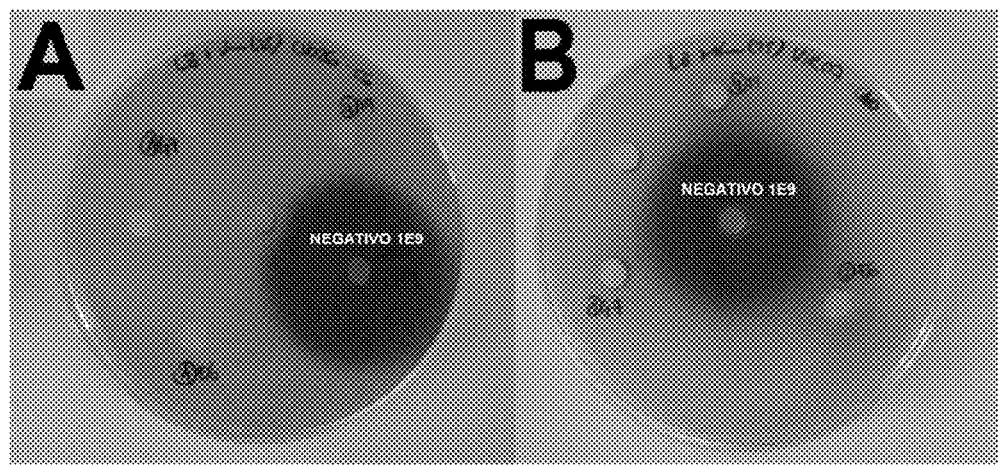
FIG. 4 shows a photograph of the bioassay in solid medium of 3 of the positive clones of the second gene library constructed from the randomly selected clone 13-E2 insert (1-E6, 1-G7 and 4-A9) and 1 negative clone (1E9) with *C. violaceum* CV026 (A) and *C. violaceum* VIR07 (B) AHL biosensors. All the assayed clones were capable of degrading C6-HSL and C10-HSL after 24 hours by hindering violacein halo formation in the biosensors. The well with violacein corresponds with a confirmed negative clone (1-E9) used as a control.

In the functional screening of this genomic library for the C10-HSL signal, about 6 or more positives showed up for each microtiter plate. Of all the positives obtained in the screening of the new subcloned genomic library, 10 were randomly chosen to perform a new inhibition bioassay in solid medium for C6-HSL and C10-HSL, as described previously, to confirm that it was indeed QQ activity. As a result, all the tested clones were positive (FIG. 4), preventing violacein halo production in the plate.

Figure 5:
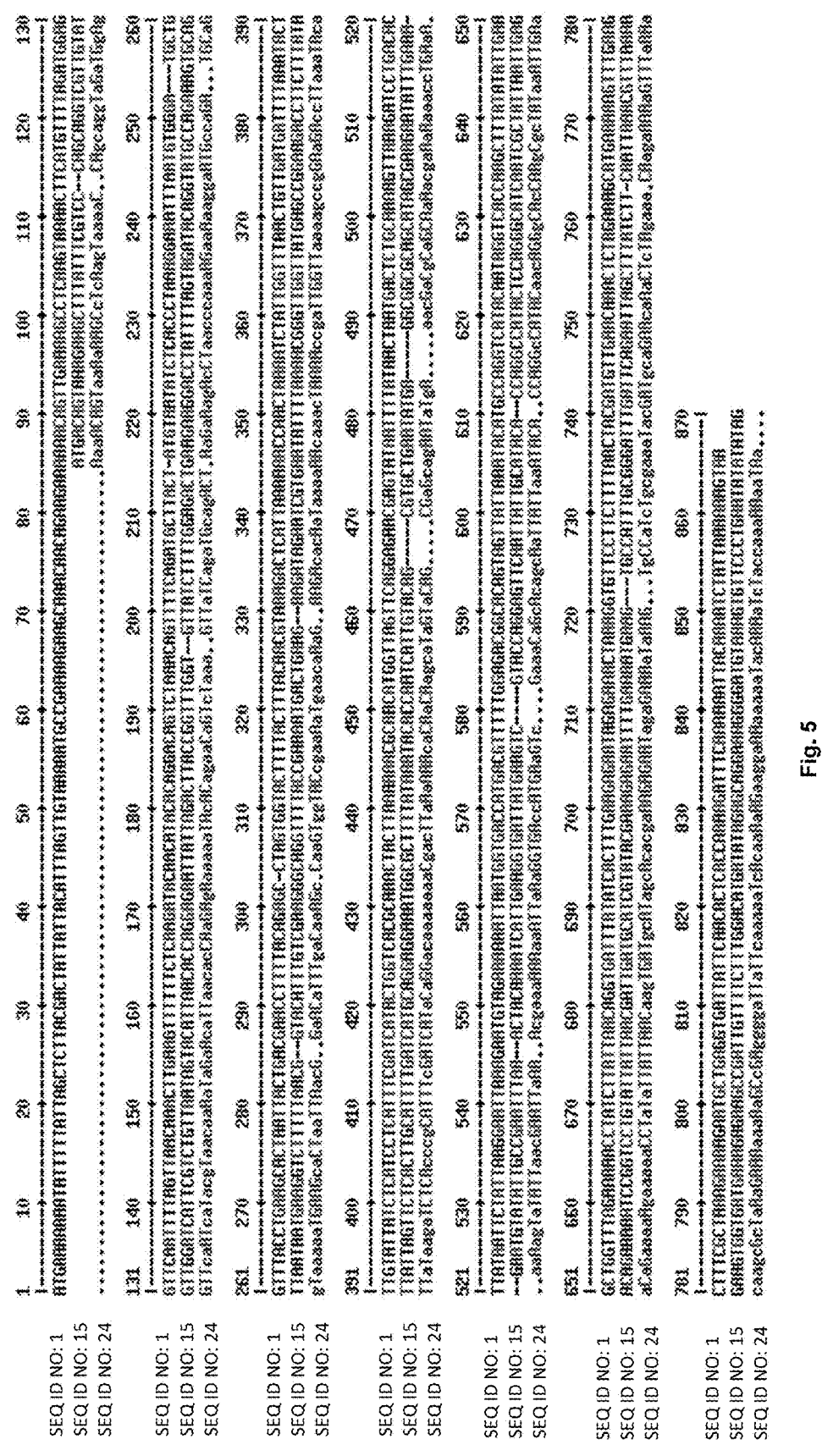
Figure 6:
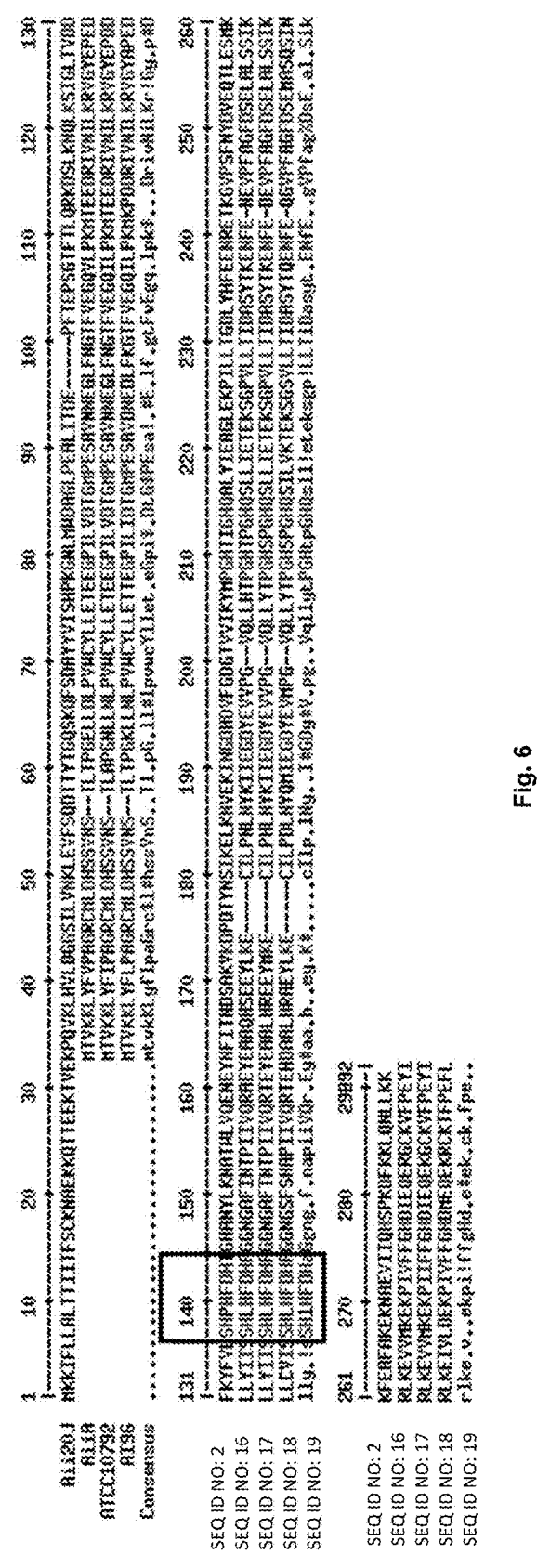

The inserts of these 10 randomly selected positive clones obtained in the analysis of the subcloned genomic library were sequenced. Inserts of between 3 and 5 kb of plasmids of 10 clones confirmed as positive after the subcloned genomic library screening were sequenced by standard techniques using the primers of pBluescript II KS (+) vector. NCBI's BLASTX and CD-Search (Conserved Domain Search) tools were used for sequence analysis and the sequences were aligned and assembled with the Phrap program. Due to the size of the inserts (3-5 Kb), it was not possible to obtain the complete sequence of any of them in a single round of sequencing, but in all cases the obtained sequences presented 100% identity with the sequence of the clone 13-E2 insert obtained by pyrosequencing and all of them contained the aii20J gene, confirming this sequence as the one responsible for QQ activity in clone 13-E2. This sequence has very low homology at the nucleotide level with the sequence of *Bacillus* aiiA, such that it cannot be detected by means of standard alignment software (FIG. 5). As regards the amino acid sequence, the conserved zinc binding domain characteristic of the metallo-β-lactamase superfamily, (HXHXDH), in addition to other histidine and aspartate residues, are found in the sequence of Aii20J for correct activity thereof (Dong et al., 2000). By aligning the consensus sequence of Aii20J with other lactonases of the genus *Bacillus* already described in the literature (FIG. 6), it was observed that, despite the low homology, they coincide in the characteristic conserved regions of this superfamily. Table 1 shows the percentages of identity of this sequence with other lactonases described in the literature. NCBI's BLAST computer tools were used to align the nucleotide and amino acid sequences and obtain the homologies.

TABLE 1

Percentages of identity of the amino acid sequence of Aii20J with other lactonases described in the literature. NCBI's BLAST computer tools were used to that end.

| Species | Homology at the amino acid level | Reference |
|---|---|---|
| *Bacillus* sp. 240B1 AiiA (SEQ ID NO: 16) | 31% | Dong et al., 2000 |
| *Bacillus* sp. AI96 AiiA (SEQ ID NO: 18) | 26% | Cao et al., 2012 |
| Uncultured *Bacillus* sp. AiiA | 30% | Carlier et al., 2003 |
| *Klebsiella pneumoniae* AhlK | 26% | Park et al., 2003 |
| *Rhodococcus erythropolys* QsdA | 18% | Riaz et al., 2008 |
| *Agrobacterium tumefaciens* AttM/AiiB | 38% | Carlier et al., 2003; Zhang et al., 2002 |

TABLE 1-continued

Percentages of identity of the amino acid sequence of Aii20J with other lactonases described in the literature. NCBI's BLAST computer tools were used to that end.

| Species | Homology at the amino acid level | Reference |
| --- | --- | --- |
| Arthrobacter sp. AhlD | 23% | Park et al., 2003 |
| Acidobacteria bacterium cosmid p2H8 QlcA | 25% | Riaz et al., 2008 |

Example 2

Figure 7:
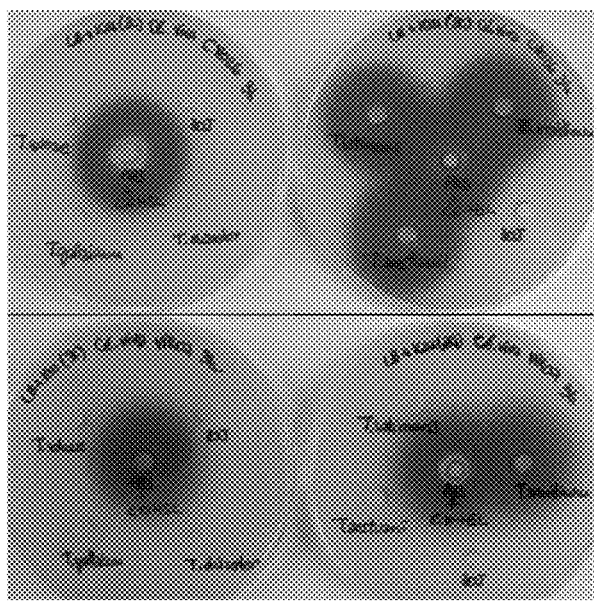
FIG. 7 shows the results of the bioassay for degrading C6-HSL (top) and C10-HSL (bottom) by living cells from different species of the genus *Tenacibaculum*. The bacteria were cultured in marine broth for 24 hours and were then resuspended in PBS pH 6.5 to which AHL at a concentration of 10 µM was added. Degradation was observed by means of the violacein production activation assay in *C. violaceum* CV026 and VIR07 biosensors producing this pigment only in the presence of AHL (Romero et al., 2011).

Sequencing Genes Homologous to the Tenacibaculum sp. Strain 20J QQ Gene in Other Strains of the Genus Tenacibaculum The presence of genes homologous to Aii20J in other species of the genus Tenacibaculum, which are shown in Table 2, was verified. Firstly, a bioassay was performed in solid medium to verify that the living cells of these strains were capable of degrading C6-HSL and C10-HSL. Only the two strains of T. maritimum did not show activity of degrading them, in contrast with previous analyses, which described that T. maritimum NCBI 2154T presented activity against C10-HSL. This difference is probably due to the fact that, in this case, the assay for activity was performed in controlled pH conditions (living cells resuspended in PBS, pH 6.5), whereas this assay was previously performed directly in the culture medium, and therefore, the degradation could be derived from high pH values derived from metabolic activity of the bacterium. Two of the tested species, T. aestuarii and T. lutimaris, presented activity only against C10-HSL (Table 2 and FIG. 7).

TABLE 2

Strains of different species of the genus Tenacibaculum and activity of living cells against C6-HSL and C10-HSL measured by means of bioassay with C. violaceum CV026 and VIR07 bioindicator strains

| Bacterial strains | Origin | C6-HSL | C10-HSL |
| --- | --- | --- | --- |
| Tenacibaculum sp. 20J | Romero, 2010. | + | + |
| T. aestuarii JCM 13491$^T$ | CECT (Valencia, Spain) | − | + |
| T. discolor DSM 18842$^T$ | CECT (Valencia, Spain) | + | + |
| T. gallaicum CECT 7122$^T$ | CECT (Valencia, Spain) | + | + |
| T. lutimaris DSM 16505$^T$ | CECT (Valencia, Spain) | − | + |
| T. maritimum CECT 4276 | CECT (Valencia, Spain) | − | − |
| T. maritimum NCBI 2154$^T$ | The National Collection of Industrial, Food and Marine Bacteria Ltd. (Aberdeen, UK) | − | − |
| T. soleae CECT 7292$^T$ | CECT (Valencia, Spain) | + | + |

Amplification was performed by means of PCR of the genes homologous to aii20J in species with QQ activity confirmed in the bioassay. The DNA of the strains was extracted from 24 h cultures with the Wizard® Genomic DNA Purification Kit (Promega) following the manufacturer's instructions. The primers (primer oligonucleotides) used in the PCR to amplify the gene sequences of the lactonases of each of the Tenacibaculum strains (Table 2) were designed from known sequences of the plasmid and from the beginning and end of aii20J gene of Tenacibaculum sp. 20J lactonase, assuming that the rest of the genus Tenacibaculum strains would have similarity at the nucleotide level with Tenacibaculum sp. 20J. For the purpose of preparing the amplified sequences for subsequent cloning and overexpression, restriction sites for enzymes NcoI, EcoRI were included in the primer sequences and keeping the sequence of the plasmid in phase so that the polyhistidine tag which the vector allows adding is correctly expressed. The sequences of these primers, referred to as Lact20Jf and Lact20JR, are shown in SEQ ID NO: 9 and SEQ ID NO: 10, respectively.

Figure 8:
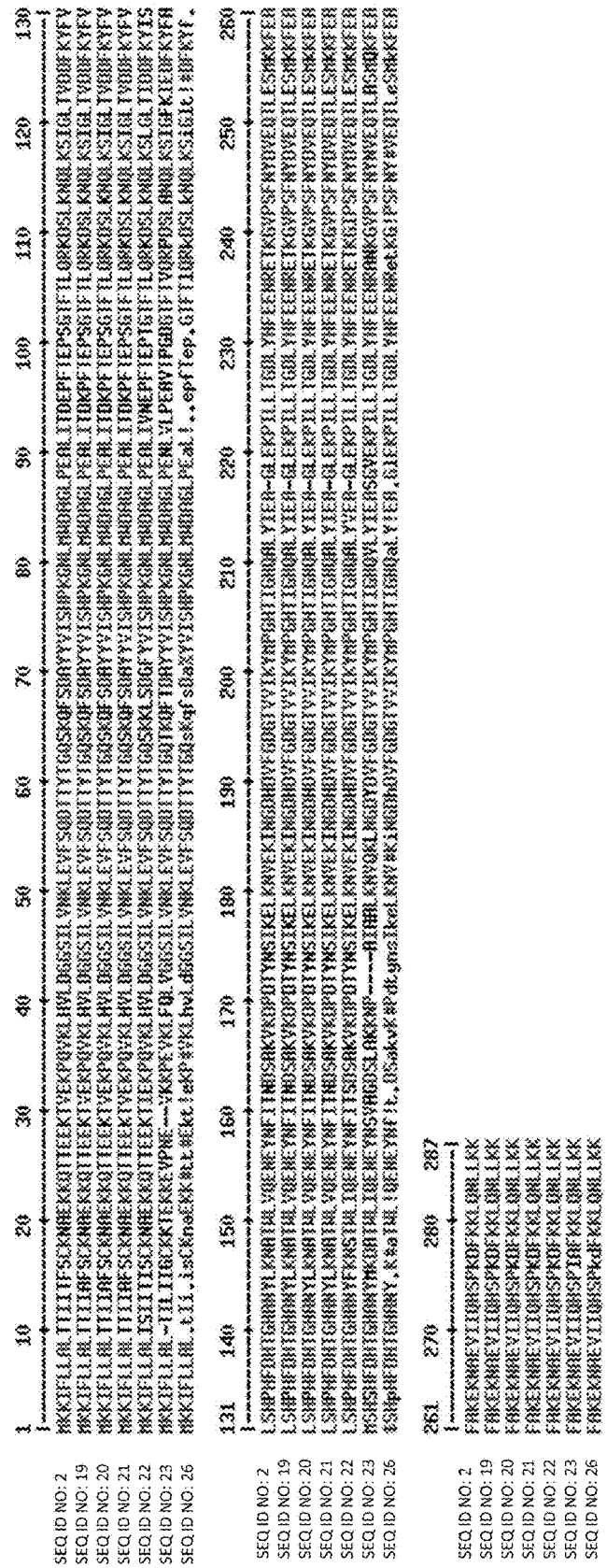
FIG. 8 shows alignment of *Tenacibaculum* sp. 20J (Aii20J) (SEQ ID NO: 2), *T. discolor* (AiiTD) (SEQ ID NO: 19), *T. gallaicum* (AiiTG) (SEQ ID NO: 22), *T. lutimaris* (AiiTL) (SEQ ID NO: 20), *T. aestuarii* (AiiTA) (SEQ ID NO: 21) and *T. soleae* (AiiTS) (SEQ ID NO: 23) lactonases obtained by means of amplification with primers designed for Aii20J ends. To align the sequences of the different lactonases and of their respective nucleotide sequences NCBI's BLAST computer tools were used.

All the primers designed in the laboratory were supplied by Sigma. PCR reactions were performed with the Mastercycler gradient thermal cycler (Eppendorf) in the following conditions: 30 denaturation cycles at 94° C. for 45 s, hybridization at 55° C. for 45 s, extension at 72° C. for 45 s, preceded by 5 minutes of denaturation at 94° C. and followed by 10 min of extension at 72° C. In the case of T. soleae, however, these reaction conditions did not work at first so PCR was performed again with a temperature gradient with the following conditions: 30 denaturation cycles at 94° C. for 15 s, hybridization at 45° C., 50° C. and 55° C. for 30 s, extension at 72° C., 1 min, preceded by 5 minutes of denaturation at 94° C. and followed by 10 min of extension at 72° C. The fragments thus obtained were purified from the gel and were sequenced by standard techniques, obtaining in all cases a sequence with high homology with the sequence of aii20J both at the nucleotide level and at the amino acid sequence level (FIG. 8, Table 3). The sequence that showed a lower degree of homology was the sequence of T. soleae, with a percentage of identity equal to 76% (Table 3). The genes homologous to aii20J of these strains, presumably responsible for the activity of degrading AHLs, were called aiiTD (of Tenacibaculum discolor), aiiTG (of T. gallaicum), aiiTL (of T. lutimaris), aiiTA (of T. aestuarii) and aiiTS (of T. soleae), producing proteins AiiTD (SEQ ID NO: 19), AiiTG (SEQ ID NO: 22), AiiTL (SEQ ID NO: 20), AiiTA (SEQ ID NO: 21) and AiiTS (SEQ ID NO: 23), respectively. The nucleotide sequences of these genes are shown in SEQ ID NO: 4 (aiiTD), SEQ ID NO: 5 (aiiTG), SEQ ID NO: 6 (aiiTS), SEQ ID NO: 7 (aiiTA) and SEQ ID NO: 8 (aiiTL). The sequences shown include the start codon (ATG) and stop codon (TAA).

TABLE 3

Percentages of identity of the nucleotide sequence of aii20J gene (SEQ ID NO: 1) and of amino acids of Aii20J protein (SEQ ID NO: 2) with the sequences obtained for other species of the genus Tenacibaculum. The percentages of identity were calculated using NCBI's BLAST computer tools.

| | Identity at the nucleotide level | Identity at the amino acid level |
| --- | --- | --- |
| T. discolor | 99% | 99% |
| T. gallaicum | 90% | 93% |
| T. soleae | 76% | 76% |
| T. aestuarii | 99% | 99% |
| T. lutimaris | 99% | 99% |

Figure 9:
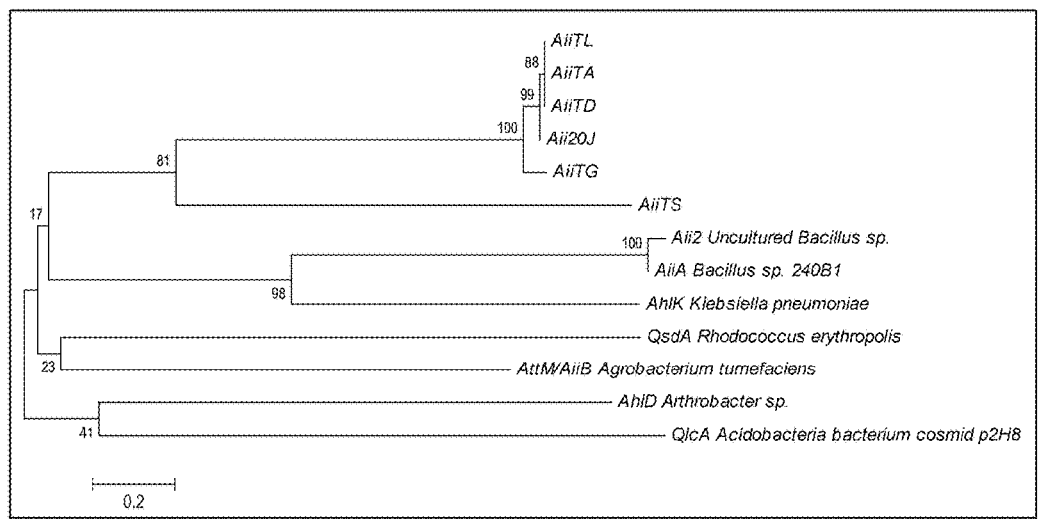
FIG. 9 shows the phylogenetic tree by means of the neighbor-joining method of the amino acid sequences of *Tenacibaculum* sp. 20J Aii20J, *T. discolor* AiiTD, *T. gallaicum* AiiTG, *T. soleae* AiiTS, *T. lutimaris* AiiTL, *T. aestuarii* AiiTA, *B. subtilis* AiiA (accession number AAY51611.1), *B. cereus* AiiA (AAY22194.1), *B. thurigiensis* AiiA (AA043435.1), uncultured *Bacillus* sp. AiiA (CAD44268.1), *Bacillus* sp. AI96 AiiA AI96 (ADK91097.1), *A. tumefaciens* AttM/AiiB (AAL13075.1), *K. pneumoniae* AhlK (AA047340.1) and *Arthrobacter* sp. AhlD (AAP57766.1). Scale bar: 0.2 amino acid substitutions per site.

A phylogenetic tree of Aii20J group lactonases and the most important representatives of the lactonase family of AHLs described in the literature (FIG. 9) was constructed using the MEGA 5.1 software, which was obtained by means of the neighbor-joining method (Saitou and Nei, 1987) and the bootstrap values were calculated by means of MEGA 5.1 software (Tamura et al., 2008). It is clearly seen in the tree that lactonases of the genus *Tenacibaculum* form a branch that is clearly differentiated from the rest of the described lactonases.

Example 3

Overexpression, Purification and Characterization of Aii20J Enzyme Activity 3.1 Cloning and Overexpression As described in the preceding section, the sequence of aii20J was amplified by means of PCR with specific primers that allowed inserting the restriction targets compatible with expression plasmid pET28c(+) (Novagen). This vector was chosen because it has the possibility of performing directional cloning and adds a fusion protein, in this case a polyhistidine tag (6 consecutive histidine residues) at the N-terminus, making protein purification easier.

The result of PCR amplification was run in 1% agarose gel electrophoresis and the corresponding DNA bands were extracted by means of the Gel Extraction Kit (Omega) following the manufacturer's protocol. Plasmid pET28c(+) was extracted in parallel from the strain where it was cultured in a routine manner (*E. coli* XL1blue) by means of miniprep with the Quiagen QIAprep® Spin Miniprep Kit following the manufacturer's protocol. Double digestion of both the obtained DNA fragments and the plasmid was then performed to obtain compatible sticky ends. The digestions were carried out with FastDigest enzymes NcoI, EcoRI, and SalI (Fermentas, Thermo Scientific) according to the conditions recommended by the manufacturer. After the digestions, the already excised PCR products were inserted into the linearized plasmid by means of enzymatic ligation using the T4 DNA ligase of Thermo Scientific for 15 min at 22° C. as indicated in the product instructions. To observe whether the ligation occurred as was expected and the plasmid had been correctly digested, control of the ligation with the plasmid was performed without the DNA insert.

Once the plasmid with the DNA insert was obtained, competent *E. coli* XL1blue cells for cloning the sequences of interest were transformed by means of electroporation using the ECM® 399 Electroporation System, BTX™ at 1,000 V, 4 ms. The electroporated cells were plated at 100 µL in LB plates supplemented with the antibiotic kanamycin (30 µg/ml) and incubated for 24 h at 37° C. Control of ligation of the plasmid without the insert was also electroporated as an electroporation control, therefore if the plasmid was well digested colonies would not grow in the plates. The obtained recombinant colonies were transferred to new plates and were frozen in parallel in Cryoinstant Mixed (VWR®) freezing vials at −80° C. for storage.

Figure 10:
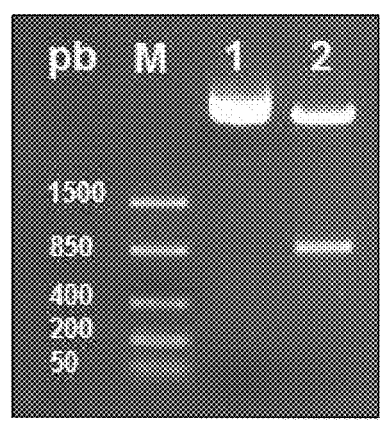
FIG. 10 shows nucleic acid electrophoresis in 1% agarose gel. Lane M: molecular weight marker (bp). 1: miniprep of an XL1blue culture transformed with pET28c(+) with the Aii20J insert. 2: double digestion of this miniprep with EcoRI and NcoI, the Aii20J gene insert (861 bp) appears in the corresponding size.

1% agarose gel electrophoresis of a miniprep extracted with the Qiagen kit from a flask with 15 ml fresh LB culture of *E. coli* XL1blue transformed with pET28c(+) with the insert and of the double digestion of the plasmid with the corresponding enzymes was performed to verify that the recombinant colonies grown in the plates after electroporation contained the plasmid with the insert (FIG. 10).

Control PCR of the recombinant colonies was also performed with primers complementary to the internal homologous domains of lactonases; the sequences of said primers are shown in SEQ ID NO: 11 and SEQ ID NO: 12, respectively.

Figure 11:
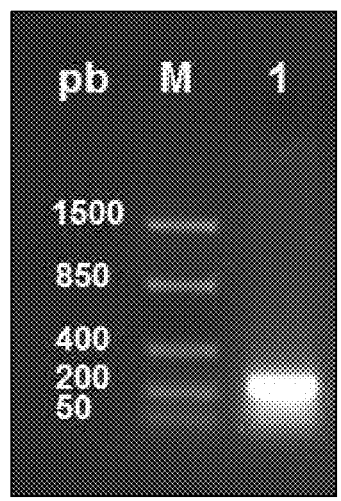
FIG. 11 shows nucleic acid electrophoresis in 1% agarose gel. M: Molecular weight marker (bp). 1: PCR of one of the recombinant colonies obtained by electroporation in BL21 (DE3) with primers TEN1F and TEN1R, the fragment appears between the internal homologous domains (237 bp) in the corresponding size.

The fragment obtained by PCR confirmed the identity of the inserted sequence (FIG. 11). The PCR conditions applied were: 30 denaturation cycles at 94° C. for 45 s, hybridization at 58° C. for 45 s, extension at 72° C., 45 s, preceded by 5 minutes of denaturation at 94° C. and followed by 10 min of extension at 72° C. This verification was observed by means of electrophoresis of the PCR product in a 1% agarose gel. The chosen recombinant colonies obtained were transferred to new LB plates with kanamycin (30 µg/ml) to culture them in a routine manner at 37° C. in the laboratory and in parallel were frozen in Cryoinstant Mixed (VWR®) freezing vials at −80° C. for storage.

With the DNA insert introduced in the plasmid and transformed into *E. coli* XL1blue cells, the plasmid DNA extractions with the insert of interest were sequenced by conventional techniques using sequencing primers specific for the vector (SEQ ID NO: 13 and SEQ ID NO: 14).

Extractions were performed by means of minipreps of 24 h cultures in 15 ml of LB medium supplemented with kanamycin (30 µg/ml) at 37° C., 170 rpm. The obtained sequences were analyzed with the Editseq and SeqMan Pro programs of Lasergene and MEGA 5.1 Beta3 (Tamura et al., 2008) to suitably assemble the sequences. The ExPASy Protein translate computer tool was used to translate the sequences by choosing the suitable open reading frame (ORF). The final sequence of the aii20J gene modified for overexpression and purification thereof is shown in SEQ ID NO: 3.

Once the sequence of the plasmid with the insert was obtained and it was verified that the sequence was in phase for correct production of the pET28c(+)plasmid polyhistidine tag, the gene of interest was cloned into the *E. coli* BL21(DE3) overexpression strain. To transform the *E. coli* BL21(DE3) cells with plasmid pET28c(+) with the DNA insert, on the one hand miniprep was performed with the Quiagen kit, of a 24 h culture of 15 ml of *E. coli* XL1blue with pET28c(+) and the insert in fresh LB medium supplemented with kanamycin (30 µg/ml) at 37° C., 170 rpm. On the other hand, the competent cells of a 24 hour BL21(DE3) culture in LB medium were made. To that end 1.5 ml of the culture were centrifuged at 14,000 rpm for 2 min, the cells were washed twice with 1 ml of 1 mM 3-(N-morpholino) propane sulfonic acid (MOPS)-10% Glycerol pH 7.3, were resuspended with the make-up volume in MOPS-Glycerol, were poured into a VWR® 90 µL sterile electroporation cuvette with a 1 mm gap size previously cooled on ice and 5 µL of the plasmid with the insert were added. The cells were electroporated in the ECM® 399 Electroporation System, BTX™ at 1,000 V, 4 ms. Then 1 ml of fresh LB medium was added to the cuvette and was left to incubate for 1 hour at 37° C., after which plates were plated with 100 µL LB supplemented with the antibiotic kanamycin (30 µg/ml) and they were incubated for 24 h at 37° C. Electroporation of the plasmid without the insert was performed as a control to verify that the plasmid was well digested, observing in this case that colonies did not grow in the plates.

Finally a bioassay for activity was performed in plates with *Chromobacterium violaceum* biosensors to make certain that the construction of the insert in the transformed plasmid in the overexpression strain presented QQ activity. To that end, some of the obtained recombinant colonies were randomly seeded in new LB plates supplemented with kanamycin (30 µg/ml). With these colonies and with a negative *E. coli* BL21(DE3) control with the plasmid, cultures were made in 15 ml of liquid LB supplemented with the antibiotic for 24 h at 37° C. and 200 rpm. After 24 hours, bioassays were performed with *C. violaceum* CV026 biosensor strains to verify C6-HSL degradation as previously described. PBS pH 6.7 with the same concentration of added AHL was also used as a negative control. The obtained recombinant colonies with activity were transferred to new LB plates with kanamycin (30 µg/ml) to culture them in a routine manner at 37° C. in the laboratory and in parallel were frozen in Cryoinstant Mixed (VWR®) freezing vials at −80° C. for storage.

Figure 12:
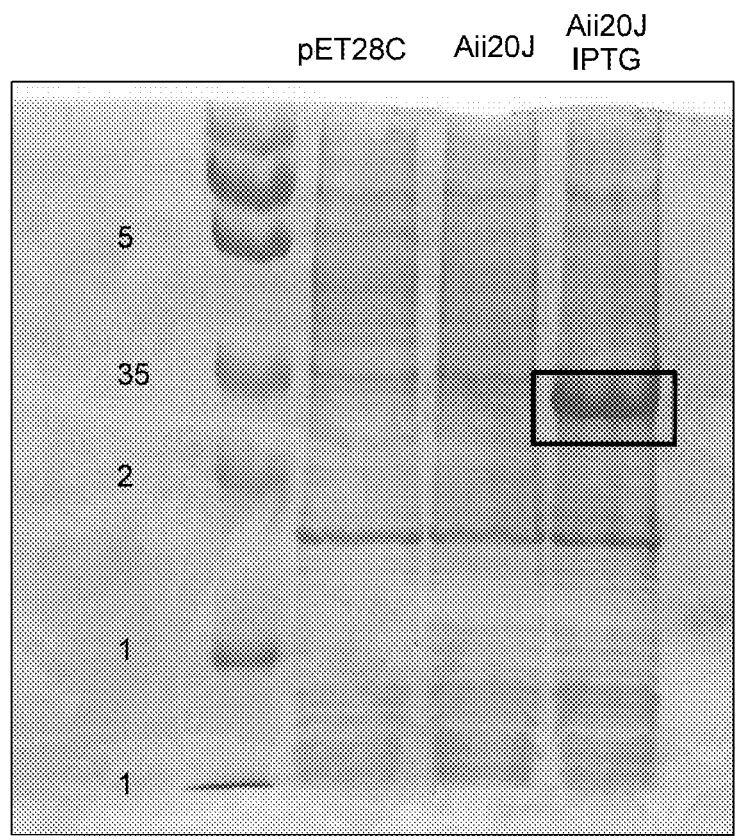
FIG. 12 shows denaturing polyacrylamide gel electrophoresis (SDS-PAGE) with Coomassie Blue staining of the cell extract of 24 h cultures of *E. coli* BL21(DE3) pET28c+, *E. coli* BL21(DE3) pET28c+ Aii20J and *E. coli* BL21(DE3) pET28c+ Aii20J induced with IPTG. Molecular marker (in kDa) is seen in the lane on the left.

Denaturing polyacrylamide gel electrophoresis (SDS-PAGE) was performed to verify that the protein band was present in the overexpression strain (FIG. 12). To that end, 50 ml LB cultures were prepared supplemented with kanamycin (30 µg/ml) at 170 rpm, 37° C. of an *E. coli* BL21(DE3) colony with plasmid pET28c(+) and the Aii20J insert, of an *E. coli* BL21(DE3) colony with the plasmid without the insert as a control and of a colony of the same *E. coli* BL21(DE3) with the plasmid and the insert to which the inducer IPTG was added at a 1 mM concentration when an optical density of the culture at 600 nm ($OD_{600}$) of between 0.4-1 (0.6 being the recommended density) was reached to induce protein overexpression, and leaving it to incubate for 3 more hours in the same conditions. The cultures were centrifuged at 9,000 rpm, 10 min, the obtained pellets were resuspended with a vortex in 3 ml of PBS pH 6.7. The cells were then ruptured by means of sonication with a Branson Sonifier 250 with constant pulses of 30-40% at medium power for half an hour and on ice so as not to overheat the samples in the process. Finally, they were filtered with sterile Minisart® 1.20 µm filters (Sartorius Stedim Biotech). After electrophoresis, the gel was stained with Coomassie Blue and the image was obtained with the Bio Rad Gel Doc™ XR+ system.

3.2 Purification of Aii20J

Figure 13:
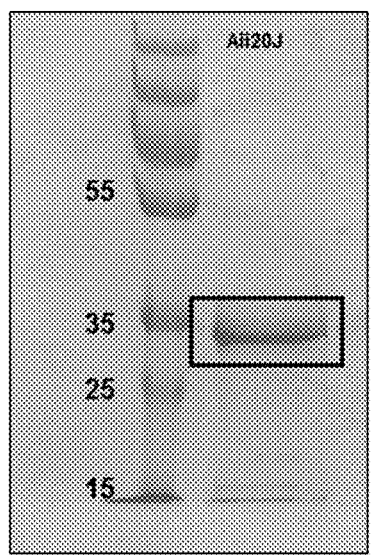
FIG. 13 shows denaturing polyacrylamide gel electrophoresis (SDS-PAGE) with Coomassie Blue staining of the Aii20J protein purified from the extract of a 24 h culture of *E. coli* BL21DE3 pET28c+ Aii20J. A histidine affinity column was used for protein purification (His GraviTrap™ affinity columns, GE Healthcare). The obtained protein band (~34.9 kDa) in the lane of the gel belongs to the fraction collected from purification. Molecular marker (in kDa) is seen in the lane on the left.

A 50 ml LB culture supplemented with kanamycin (30 µg/ml) of an *E. coli* BL21(DE3) colony with plasmid pET28c(+) and the insert corresponding to the lactonase gene of the determined *Tenacibaculum* sp. strain to be purified was prepared, and incubated at 170 rpm, 37° C. until reaching an optical density at 600 nm ($OD_{600}$) of the culture of between 0.4-1 (0.6 being the most highly recommended density). IPTG at a 1 mM concentration was added to induce protein overexpression and it was left to incubate for 3 more hours in the same conditions. The culture was centrifuged at 9,000 rpm, 10 min, the pellet was resuspended with a vortex in 20 ml of PBS pH 6.7. Then the cells were ruptured by means of sonication with the Branson Sonifier 250 with constant pulses of 30-40% at medium power for half an hour and on ice so as not to overheat the sample in the process. Cells were centrifuged for 10 min at 9,000 rpm to form a pellet. Two washing operations were performed by resuspending the pellet by means of vortexing in 10 ml of PBS pH 6.7 with 1% Triton, under continuous sonication at medium power for 1 min. Then the pellet was resuspended in 5 ml of binding buffer from the purification column, the lysate was adjusted to pH 7.4 and was left to stand for 1 hour on ice. It was then purified through the GE Healthcare His GraviTrap™ affinity column with elution buffer according to the instructions indicated by the manufacturer. The binding buffer and the elution buffer were prepared by means of the GE Healthcare His Buffer Kit with 6 M urea. The eluate obtained from the column that contained the protein was dialyzed to remove excess urea. To this end, Sigma Seamless Tubing membranes introduced in previously distilled water were used, and the urea molarity was reduced by half with PBS pH 6.7 every hour to prevent the protein from precipitating and to eliminate it almost completely. To verify that the purified enzyme was correctly obtained, SDS-PAGE was performed on the purified and dialyzed protein (FIG. 13). The gel was stained with Coomassie Blue and the image was obtained with the Bio Rad Gel Doc™ XR+ system. The result of the dialysis was distributed in Eppendorf® tubes and it was preserved at 4° C. in the refrigerator. For long-term preservation thereof, it was frozen in 100 µL aliquots at −80° C., avoiding freezing/thawing cycles to ensure that the enzyme did not lose activity. The protein concentration obtained in each purification was quantified with a Quawell UV-Vis Spectrophotometer Q500.

3.3 Characterization of the Activity of Aii20J

Figure 14:
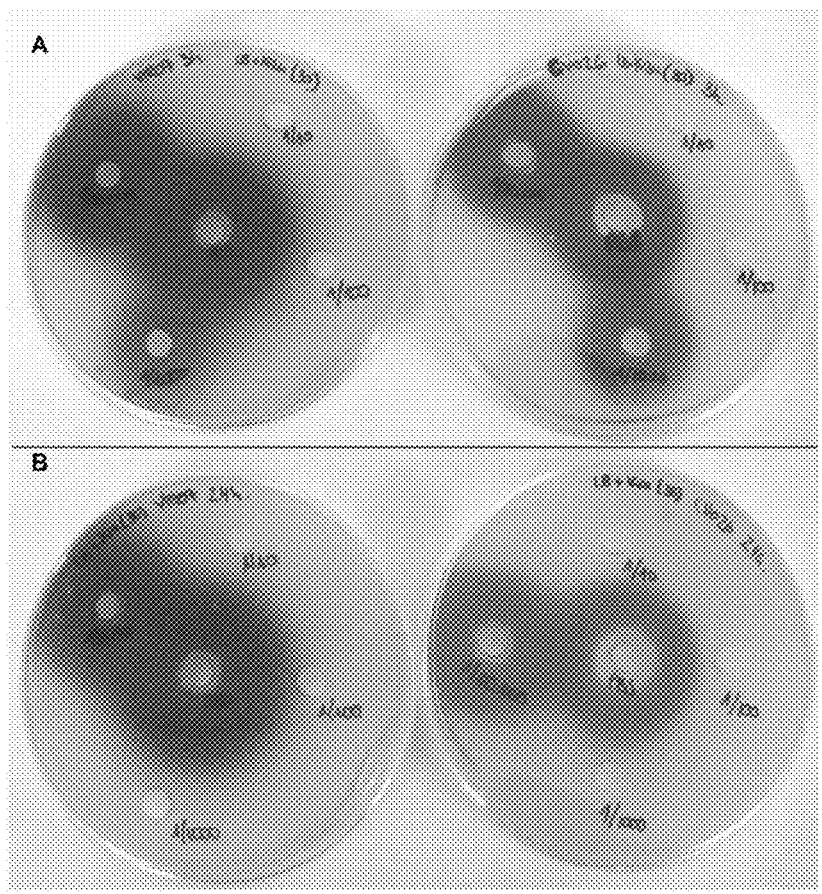
FIG. 14 shows the bioassay to determine the Minimum Active Concentration (MAC) of Aii20J versus C6-HSL (CV026) and C10-HSL (VIR07). Different dilutions of a 0.2 mg/ml AiiA solution were incubated with AHLs at a concentration of 10 µM for 3 hours (upper panel) and 24 hours (lower panel). MAC was considered to be the concentration of the highest dilution that achieved complete elimination of the signal (absence of violacein halo) in the stipulated time.

Activity of purified enzyme Aii20J obtained by means of the techniques described in section 3.2 was characterized. To that end, the Minimum Active Concentration (MAC), defined as the minimum amount of enzyme needed to completely remove 10 µM concentration of AHL in a given time period, was established. To that end, serial dilutions (1:10, 1:100, 1:1.000 and 1:10,000) in PBS pH 6.7 of an enzyme solution having a concentration of 0.2 mg/ml were made. C6-HSL and C10-HSL were added to these solutions to obtain a final concentration of 10 µM, being incubated for 3 and 24 hours at 22° C. under stirring, 200 rpm. Once incubation ended, the presence of C6-HSL and C10-HSL was evaluated by means of a plate bioassay with the *C. violaceum* CV026 and *C. violaceum* VIR07 bioindicator strains, establishing that the MACs of Aii20J for both C6-HSL and C10-HSL are 2 µg/ml for incubation times of 3 hours and ten times less, 0.2 µg/ml, for incubation times of 24 hours (FIG. 14). On this basis, a concentration of 20 µg/ml was used in all the characterization assays, corresponding to 10 times the 3 hour MAC on C6-HSL and C10-HSL.

3.3.1 Kinetics of C6-HSL and C10-HSL Degradation

HPLC-MS was used to evaluate the degradation kinetics of 2 AHLs (C6-HSL and C10-HSL) of the purified enzyme Aii20J. To that end, it was incubated at a concentration of 20 µg/ml in PBS pH 6.7 with C6-HSL and with C10-HSL at a final concentration of 50 µM at 22° C., 200 rpm. At different incubation times (0, 10, 20, 30, 60 and 90 min), 200 µL aliquots were taken in triplicate from all the tubes to perform organic extraction of the reaction mixtures, extracting three times with the same volume of ethyl acetate (200 µL). The solvent was recovered and evaporated by means of nitrogen flow in a bath at 50° C., and the obtained dry extract was resuspended in 400 µL of acetonitrile for subsequent analysis and quantification of the concentration of the remaining signal by HPLC-MS. The same kinetics were performed in the same manner with purified AiiA for the two signals at a final concentration of 40 µg/ml to compare it with the activity of Aii20J, extracting at incubation times 0, 30 and 90. The controls were performed with PBS supplemented with the same amount of C6-HSL or C10-HSL signal and were processed and organically extracted in the same manner.

Analysis was carried out with HPLC 1100 series (Agilent USA) equipped with a C8 precolumn (2.1×12.5 mm, 5 µm particle size) and a ZORBAX Eclipse XDB-C18 2.1×150 mm column (with 5 µm particle size), kept at 45° C. The mobile phase consisted of 0.1% formic acid in water (A) and 0.1% formic acid in acetonitrile (B) with a flow rate of 0.22 ml/min. Elution conditions: 0 min 35% of B, linear gradient up to 60% of B for 10 min, linear gradient of 60 to 95% of B for 5 min, 95% of B for 5 min and one minute to return to the initial conditions which were maintained for 9 min. 20

μL aliquots of each sample in acetonitrile were diluted with 0.1% formic acid before injection into the column. The mass spectrometer (MS) used was a triple quadrupole API 4000 (Applied Biosystem, CA, USA) equipped with a Turbo Ion source used in positive-ion electrospray and multiple reaction monitoring (MRM) mode. The MRM signals were used to obtain relative quantification information by comparison with a calibration curve constructed by molecular ion abundance obtained from standard synthetic AHLs (Milton et al., 2001).

Figure 15:
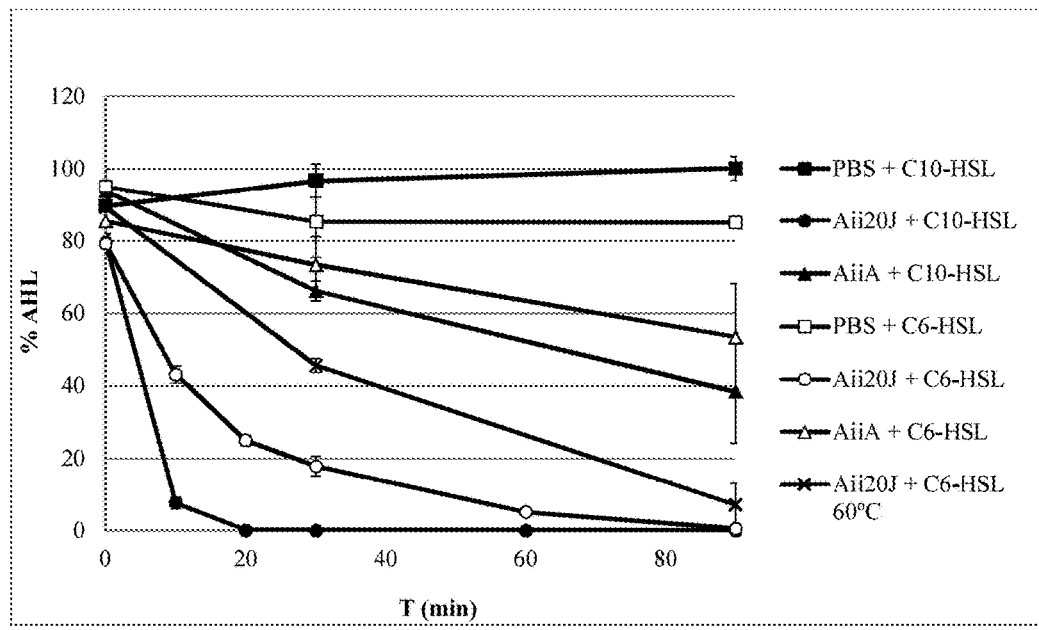
FIG. 15 shows the kinetics of 50 µM C6-HSL and C10-HSL degradation by means of purified *Tenacibaculum* sp. 20J Aii20J (20 µg/ml) or by means of purified *Bacillus* sp. AiiA (40 µg/ml) and thermal stability of Aii20J at 60° C. with C6-HSL (50 µM) determined by means of HPLC-MS analysis. The controls were established with signals in PBS. The data represents the mean of 3 independent reactions, showing the mean and standard deviation.

The obtained results are shown in FIG. 15, where it can be seen that, inter alia, Aii20J completely degrades C10-HSL in 20 minutes, whereas it takes more than 80 minutes to completely degrade C6-HSL. However, in the time considered, neither complete C6-HSL degradation nor complete C10-HSL degradation due to the action of AiiA is observed.

3.3.2 Specificity of Aii20J

Figure 16:
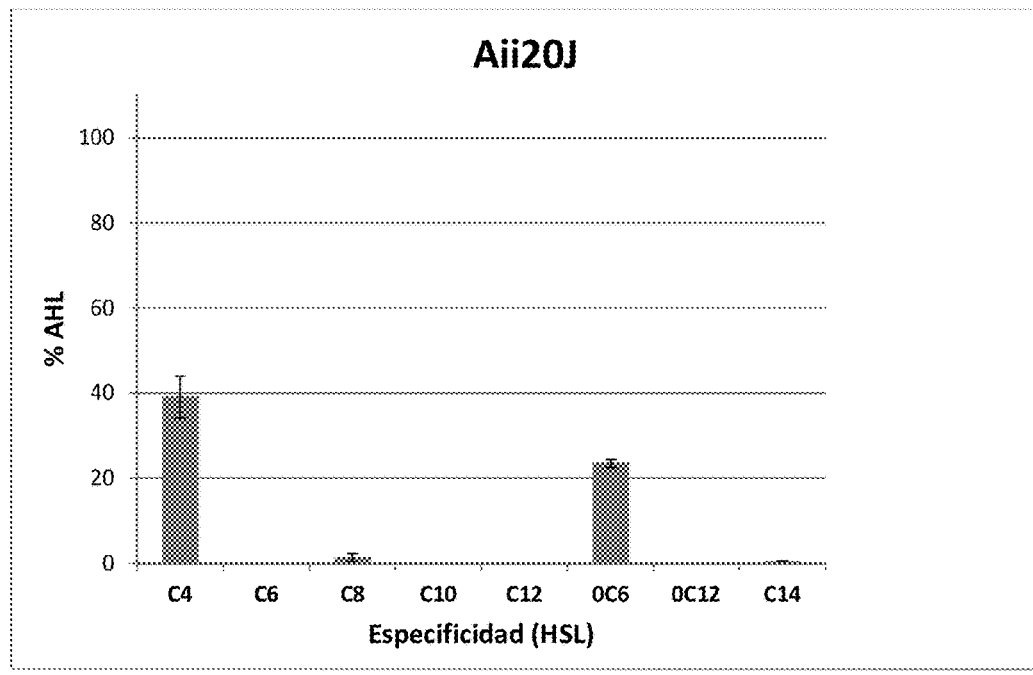
FIG. 16 shows degradation of different AHLs by a 20 µg/ml Aii20J solution in the period of 1 hour at a temperature of 22° C. The percentage of non-degraded AHL, measured by HPLC-MS, is depicted.

Assays identical to those described in section 3.3.1 for unsubstituted AHLs C4-HSL, C6-HSL, C8-HSL, C10-HSL, C12-HSL, C14-HSL and for the oxo- or hydroxy-substituted AHLs OC6-HSL and OC12-HSL were performed with a 10 μM concentration of AHL and a 20 μg/ml concentration of enzyme. The initial and final concentrations were measured in triplicate in extracts done in PBS pH 6.7 and quantified by means of HPLC-MS (Romero et al., 2011). Aii20J has the smallest degree of affinity against C4-HSL, followed by oxo-AHL OC6-HSL. The rest of the AHLs tested are completely degraded in 1 hour by a 20 μg/ml concentration of the enzyme (FIG. 16). This broad spectrum of activity makes Aii20J one of the most active QQ enzymes described, because in other cases the range of AHLs that can be removed is lower. In the case of AiiA$_{AI96}$ the greatest activity is against C6, C7, C8 and C10-HSL, but no activity against C12-HSL was observed (Cao et al., 2012).

3.3.3 Resistance to pH

Figure 17:
FIG. 17 shows a photograph of the pH-resistance bioassay in solid medium of Aii20J purified at a final concentration of 20 µg/ml at 22° C. with different buffers (pH values of 3-9) for the two C6-HSL (left plate) and C10-HSL (right plate) signals. The AHLs were incubated for 3 hours with the enzyme previously treated at the indicated pH.

For the purpose of measuring the effect of the pH of the medium on the stability of Aii20J and to therefore establish the viability of the inclusion thereof in feeds or medicaments that must be ingested orally, stability of the enzyme after being exposed to different solutions having a controlled pH in the range 3-9 was verified. A 20 μg/ml Aii20J solution was incubated in different sterile buffers with different pH for 30 min at 22° C. Then the pH was adjusted with 1M HCl or 1M NaOH until reaching pH 6.7 (standard conditions for measuring the activity) and the AHL (C6-HSL and C10-HSL with a final 10 μM concentration) was added, leaving it to incubate for 3 h at 22° C. The presence of AHLs was shown by means of a bioassay with the *C. violaceum* indicator strains, CV026 and VIR07 (FIG. 17). The wells in the center correspond with the negative PBS controls, pH 6.7 with the corresponding AHL. The buffers used were McIlvaine buffer (for pH 3, 4 and 5), PBS buffer (pH 6 and 7) and 0.05 M Tris-HCl (pH 8 and 9). These results clearly show the existence of a stability range of Aii20J that is much greater than that described for AiiA$_{AI96}$, which significantly loses activity when exposed to solutions having a pH less than 6 (Cao et al., 2012).

3.3.4 Resistance to the Action of Proteinase K and Chymotrypsin

Figure 18:
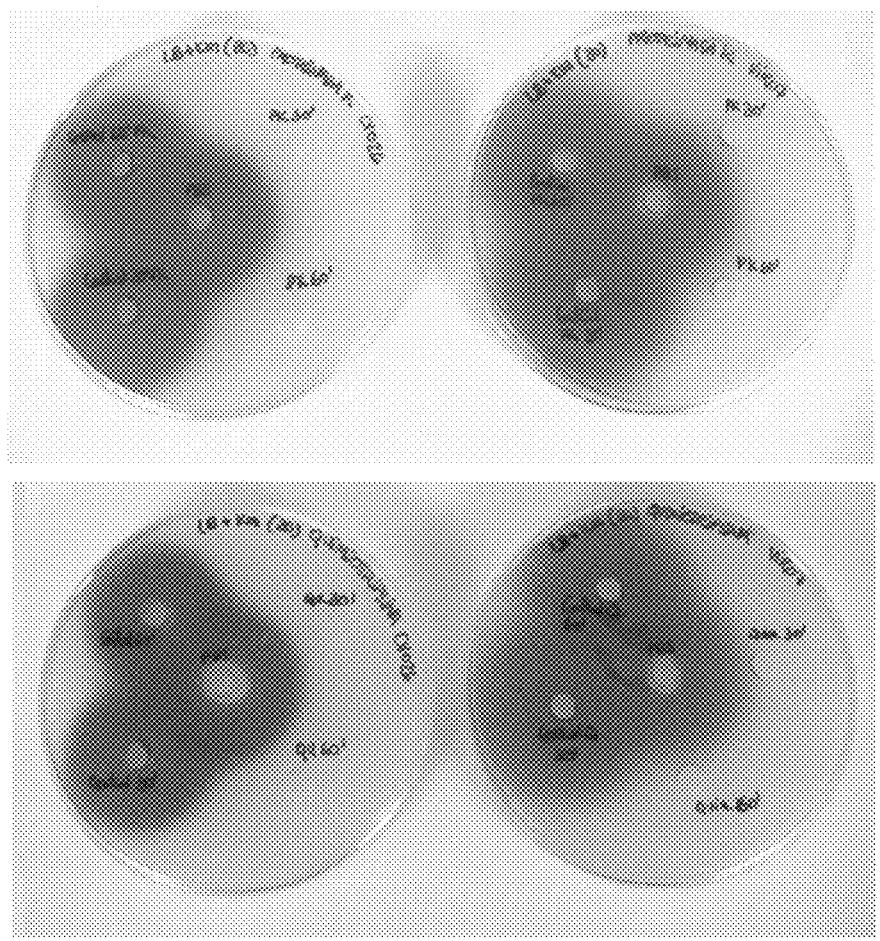
FIG. 18 shows the effect of chymotrypsin (lower panel) and proteinase K (upper panel) on the enzyme activity of Aii20J. Aii20J (20 µg/ml) was incubated with solutions of both enzymes (1:10 proteinase K/Aii20J and 1:60 chymotrypsin/Aii20J) for 30 or 60 minutes and C6-HSL or C10-HSL was then added to evaluate the activity of the enzyme. The central wells correspond with the negative control of PBS plus the corresponding AHL, and the negative controls of proteinase K and chymotrypsin treated in the same conditions as the samples but without enzyme Aii20J appear with a violacein halo.

With the same objective as the evaluation of resistance to pH, the resistance of Aii20J to the action of proteinase K and chymotrypsin was tested (FIG. 18). Aii20J was individually incubated at a 20 μg/ml concentration for 30 min and 1 h at 30° C. in PBS pH 6.7 with proteinase K at a protease-protein ratio of 1:10 (w/w) added from a 50 μg/ml stock solution in distilled H$_2$O and α-chymotrypsin at a protease-protein ratio of 1:60 from a 25 μg/ml stock solution in 100 mM Tris-HCl, pH 7.4. After the incubation times, C6-HSL and C10-HSL were added at a final 10 μM concentration and were further incubated for 24 h at 22° C. and 200 rpm. Resistance of the activity of Aii20J to proteolysis was determined by means of an inhibition bioassay with the *C. violaceum* CV026 and VIR07 biosensors. Negative proteinase K and chymotrypsin controls in PBS pH 6.7 without the enzyme and with the same added concentration of AHLs, and a negative PBS control with the AHLs at the same concentrations were made.

3.3.5 Resistance to Temperature

Figure 19:
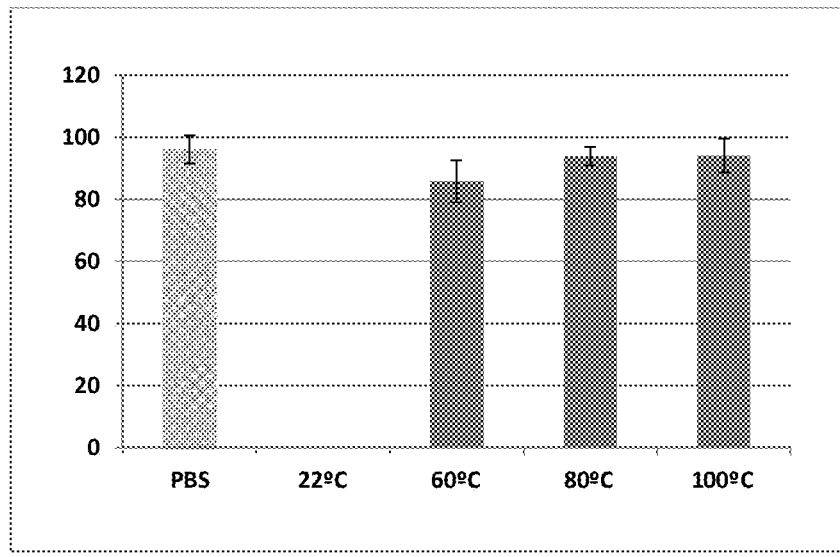
FIG. 19 shows HPLC-MS analysis of the C6-HSL degradation capacity by means of purified Aii20J with prior treatment with different temperatures (22, 60, 80 and 90° C.) for 10 minutes. The protein concentration was 20 µg/ml. The control (bar with dots) was done in PBS.

The thermal stability of Aii20J was evaluated by subjecting a solution of the enzyme having a 20 μg/ml concentration in triplicate at different temperatures for 10 minutes, measuring the activity of the enzyme thus treated on C6-HSL (10 μM) for 1 h, 22° C., 200 rpm, which was quantified by means of HPLC-MS techniques. The results demonstrate limited thermal stability of Aii20J because it loses its catalytic activity above 60° C. (FIG. 19). This result strongly conflicts with the thermal stability of enzyme activity in crude cell extracts, in which the activity resists treatments of up to 100° C. for 10 minutes (the results are not shown). Furthermore, the thermal stability of Aii20J was also verified by HPLC-MS by subjecting a 20 μg/ml Aii20J solution to 60° C. for 10 minutes, after which it was incubated with a 50 μM concentration of C6-HSL at 22° C. At different incubation times (0, 30 and 90 minutes), aliquots were extracted in triplicate to quantify their residual activity by means of HPLC-MS analysis in the same manner as in section 3.3.1 (FIG. 15). PBS supplemented with the same amount of C6-HSL signal, processed and organically extracted in the same manner, was used as a control. Over 90 minutes, Aii20J almost completely degraded the entire signal compared with the control, although the enzyme treated at 60° C. presented somewhat slower kinetics than the untreated enzyme, as seen in FIG. 15. Compared with the limited thermal stability results (FIG. 19), Aii20J does not lose the capacity to degrade AHLs at 60° C. (FIG. 15).

Figure 20:
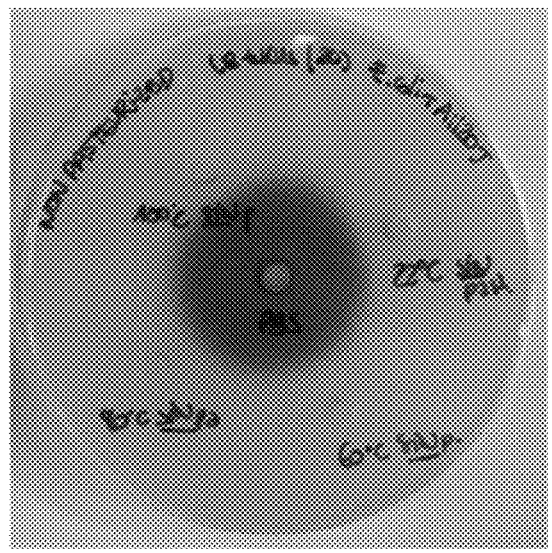
FIG. 20 shows a photograph of the bioassay in solid medium of *E. coli* BL21DE3 CCE with plasmid pET28c(+) and Aii20J for C6-HSL. The activity of 20J in the extract resisted treatment with all the temperatures degrading the C6-HSL signal after 3 hours by hindering violacein halo formation in the biosensor. The central wells correspond with the negative controls of PBS with the same AHL concentration (10 µM).

To verify whether the difference in thermal resistance between the purified enzyme and the *Tenacibaculum* sp. strain 20J cell extract may be due to presence of a second heat resistant enzyme in the strain, the thermal resistance of the activity was tested in *E. coli* BL21DE3 cell extracts with plasmid pET28c(+). The diluted crude cell extract at a concentration 10 times greater than the minimum active concentration (46.8 μg of protein from the extract/ml at both 3 h and 24 h) was incubated in Eppendorf® tubes with PBS pH 6.7 at 22° C., 60° C., 80° C. and 100° C. for 10 min. Then they were left to cool at room temperature, the C6-HSL signal molecule was added at a final 10 μM concentration and were left under stirring at 200 rpm for 3 h at 22° C., after which the violacein inhibition bioassay was performed. PBS with the same amount of C6-HSL signal was used as a control. The results clearly show that the *E. coli* extract in which Aii20J is expressed has the same thermal resistance profile as the original 20J strain (FIG. 20), which indicates that the low thermal resistance of purified Aii20J could be due to the lack of a co-factor which increases its sensitivity and which is present in the cell extracts.

3.3.6 Interaction of Aii20J with Antibiotics from the β-Lactam Family

Figure 21:
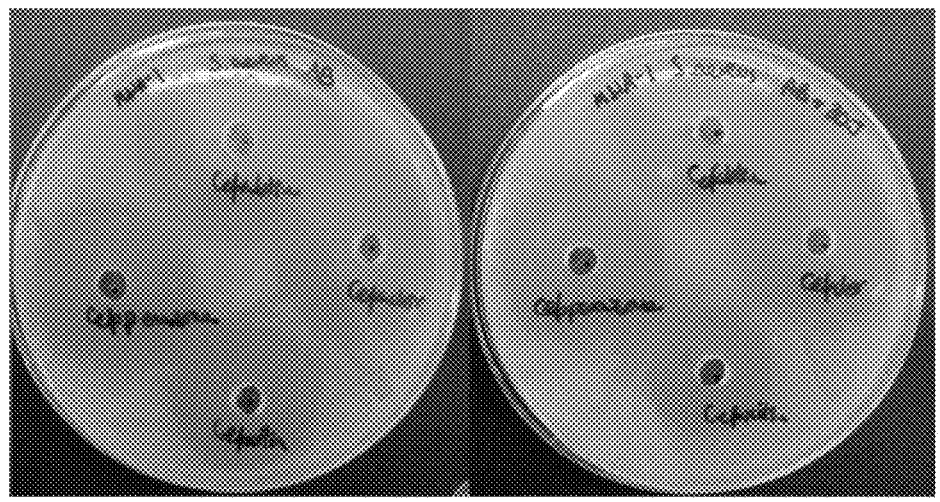
FIG. 21 shows the absence of Aii20J interference with the action of some β-lactam antibiotics. The figure shows an antibiogram of wells having different antibiotics from the cephalosporin group against *Staphylococcus aureus*. The plate on the left shows the untreated antibiotics. The plate on the right shows the antibiotics treated with Aii20J (20 µg/ml for hours). The diameter of the inhibition halos was not affected by treatment with the enzyme for any of the tested β-lactamase antibiotics and inhibitors.

Due to the homology of Aii20J and the rest of the AHL lactonases with the β-lactamases responsible for the resistance of a number of bacteria to these antibiotics (Bebrone, 2007), the possible activity of Aii20J out of a total of 11 β-lactam antibiotics belonging to 5 families of the group (penicillin g, methicillin, amoxicillin, ampicillin, cefalotin, cefaclor, cefoxitin, ceftriaxone, cefoperazone, imipenem and meropenem) and two β-lactamase inhibitors (sulbactam and clavulanic acid) was verified. The antibiotics were incubated for 24 hours with a 20 µg/ml Aii20J solution, verifying the activity thereof compared to the same antibiotic solution that was not enzymatically treated by means of an antibiogram in a well with the bacterium Staphylococcus aureus ATCC 25923. Halos having the same diameter were obtained in the plates corresponding to the antibiotic alone and to the antibiotic treated with Aii20J, which indicates that there is no interaction between Aii20J and the action of these β-lactam antibiotics, or with the tested β-lactamase inhibitors either (FIG. 21).

Example 4

Acid Resistance in E. coli K-12 MG1655 and E. coli EHEC EDL 933

For the purpose of observing whether the Aii20J lactonase could reverse the protective effect of AHLs in E. coli cultures when they are exposed to low pHs, an acid resistance assay was carried out. The E. coli strains were cultured in LB medium for 48 h at 30° C. and under stirring (170 rpm). After that time, the cultures were inoculated in preheated LB medium with 0.4% glucose to repress the acid resistance system (AR-1), with the different conditions and under continuous stirring at the same temperature: E. coli, E. coli plus OC6-HSL at a final 5 µM concentration, E. coli plus Aii20J at 20 µg/ml and E. coli plus OC6-HSL and Aii20J at the same concentrations. After 14-15 hours of incubation, a 1:1000 dilution of each culture in acid medium (MEM) pH 2.0, supplemented with 0.4% glucose and preheated 1.6 mM glutamate was made. At 0, 1.5 and 3 hours (30° C., 170 rpm), 100 µL of each reaction were poured in LB plates. The plates were incubated for 24 hours at 30° C. to determine the survival of E. coli by means of CFU (colony forming units) count. The MEM medium was prepared from a 50× solution with 670 ml of distilled water, 10 g of $MgSO_4.7H_2O$, 100 g of citric acid.$H_2O$, 500 g of $K_2HPO_4$ and 175 g of $NaNH_4HPO_4.4H_2O$. The final approximate volume was 1 L, which was used to make a 1× dilution in distilled water and was adjusted to pH 2.0 before autoclaving. The glucose (0.4%) and glutamate (1.6 mM) were independently added in sterilized form.

Figure 22:
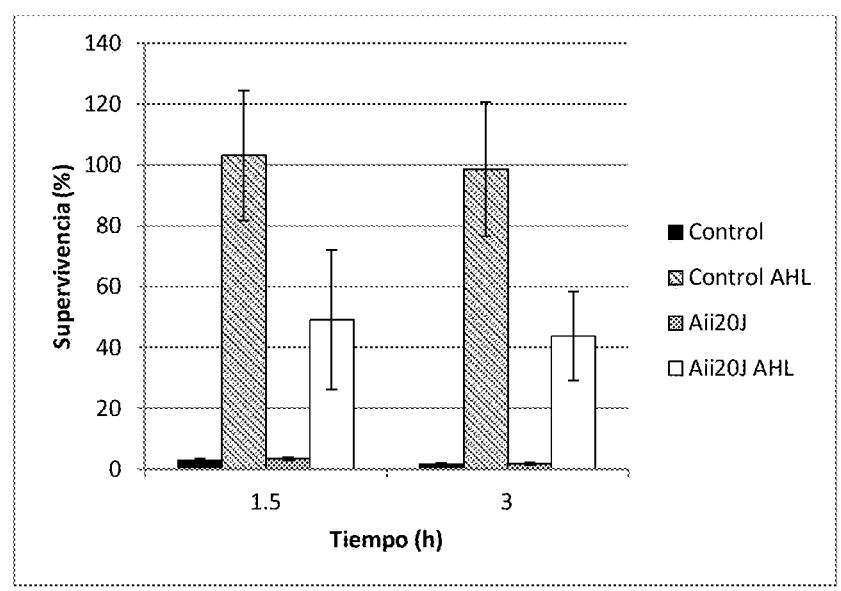
FIG. 22 shows *E. coli* K12 MG1655 acid resistance. The cells were cultured in LB glucose (0.4%) with different conditions: *E. coli* K-12 (Control), *E. coli* with 5 µM OC6-HSL (AHL control), *E. coli* with Aii20J at 20 µg/ml (Aii20J) and *E. coli* with OC6-HSL and Aii20J (AHL Aii20J) at 30° C., and they were then subcultured in MEM at pH 2.0 with glucose (0.4%) and glutamate (1.6 mM) at the same temperature. *E. coli* survival was determined by means of quantifying CFU/ml at 0, 1.5 and 3 hours and was expressed as the percentage (%) of viable cells with respect to 0 hours. Each condition was assayed in triplicate and the error bars represent the standard deviation.

The obtained results are shown in FIG. 22.

Discussion

In E. coli, resistance to an acid environment is controlled by means of the presence of AHL-type QS signals. E. coli does not produce those signals, but it can feel the signals produced by other bacteria in the rumen or in the intestine of animals due to the presence of a specific sensor called SdiA. It has been demonstrated that inactivation of the SdiA sensor reduces spreading of E. coli O157:H7 in fecal matter in weaned calves, probably by reducing colonization capacity (Sharma & Bearson, 2013). FIG. 22 shows the effect of the addition of the enzyme Aii20J on acid resistance in E. coli strain K-12 MG1655. In this experiment, the effect of the addition of external AHLs and the action of Aii20J lactonase on the viability of E. coli cells exposed to pH 2.0 has been verified. The results have demonstrated that the presence of external AHLs confers to E. coli complete acid resistance compared with the control cultures. The addition of Aii20J to control cultures has no significant effect on the resistance of E. coli to an acid environment, whereas the addition of Aii20J to cultures to which AHLs were added resulted in a significant reduction (around 50%) in cell viability compared with cultures that were resistant to acid due to the presence of AHLs.

Acid resistance is an important characteristic of the virulence of gastrointestinal pathogens, such as E. coli, and the sdiA gene plays a key role in regulating the acid glutamate-dependent resistance system as well as in the control of QS-dependent virulence factor production in E. coli K-12 and EHEC. The results herein provided confirm the potential use of Aii20J in the control of the expression of important human pathogens such as E. coli.

The invention claimed is:

1. A peptide with Quorum Sensing (QS) inhibitory activity encoded by the nucleotide sequence shown in SEQ ID NO: 1, or a variant thereof having a degree of identity of at least 76% with respect to said SEQ ID NO: 1, wherein the peptide forms part of a fusion protein that comprises a peptide useful for isolating and/or purifying proteins.

2. The peptide according to claim 1, wherein the peptide comprises the amino acid sequence shown in SEQ ID NO: 2, or a variant thereof having a degree of identity of at least 76% with respect to said SEQ ID NO: 2 and maintaining Quorum Sensing (QS) inhibitory activity.

3. The peptide according to claim 2, the amino acid sequence of which consists of SEQ ID NO: 2.

4. A composition comprising the peptide according to claim 1.

5. A food product comprising the composition according to claim 4 and a vehicle suitable for food.

6. A method for the preparation of a food product comprising adding the peptide according to claim 1 to a vehicle suitable for food.

7. A pharmaceutical composition comprising the composition according to claim 4 and a pharmaceutically acceptable vehicle.

8. A method for the prevention and/or treatment of a bacterial infection in a subject comprising the administration to said subject of the peptide according to claim 1.

9. The method according to claim 8, wherein a bacterium causing the bacterial infection is a quorum sensing (QS) signal-producing bacterium.

10. The method according to claim 8, wherein a bacterium causing the bacterial infection is a biofilm-forming bacterium.

11. The method according to claim 9, wherein said QS signals produced by the bacterium causing the bacterial infection comprise an N-acyl-homoserine lactone (AHL), wherein said AHL is (i) an unsubstituted AHL, wherein said unsubstituted AHL is selected from the group consisting of C4-HSL, C6-HSL, C8-HSL, C10-HSL, C12-HSL, C14-HSL and combinations thereof; (ii) an oxo- or hydroxy-substituted AHL, wherein said oxo- or hydroxy-substituted AHL is selected from the group consisting of OC6-HSL, OC12-HSL and combinations thereof; or (iii) combinations of (i) and (ii).

12. An agricultural composition comprising the composition according to claim 4 and an agriculturally acceptable vehicle.

13. A method for controlling a bacterial disease in a plant, which comprises
putting said plant in contact with the peptide according to claim 1, wherein said bacterial disease is caused by a quorum sensing (QS) signal-producing bacterium, under conditions that allow controlling said bacterial disease
wherein said bacterial disease is caused by a quorum sensing (QS) signal-producing bacterium, under conditions that allow controlling said bacterial disease.

14. A method for causing a quorum quenching (QQ) process in response to a quorum sensing (QS) process, wherein said QS process is caused by a QS signal-producing bacterium, which comprises putting said bacterium in contact with the peptide according to claim 1, under conditions that allow causing said QQ process.

15. A method for inhibiting a quorum sensing (QS) process, wherein said QS process is caused by a QS signal-producing bacterium, which comprises putting said bacterium in contact with the peptide according to claim 1, under conditions that allow inhibiting said QS process.

16. An in vitro method for breaking down a quorum sensing (QS) signal, which comprises putting the peptide according to claim 1, in contact with said QS signal, under conditions that allow breaking down said QS signal.

17. An in vitro method for modulating the signaling activity of an N-acyl-homoserine lactone (AHL), which comprises putting the peptide according to claim 1, in contact with said AHL, under conditions that allow modulating the signaling activity of said AHL.

18. An in vitro or ex vivo method for inhibiting bacterial biofilm formation, wherein said bacterial biofilm is produced by a quorum sensing (QS) signal-producing bacterium, which comprises putting the peptide according to claim 1, in contact with said QS signal-producing bacterium, under conditions that allow inhibiting said bacterial biofilm formation.

19. A method for the preparation of the peptide according to claim 1, comprising culturing a cell under conditions that allow the production of the peptide, and optionally recovering the peptide from the culture medium, wherein the cell comprises a polynucleotide comprising the nucleotide sequence shown in SEQ ID NO: 1, or a variant thereof having a degree of identity of at least 76% with respect to said SEQ ID NO: 1 and encoding a peptide with Quorum Sensing (QS) inhibitory activity, provided that said cell is not a bacterium of the genus *Tenacibaculum*.

20. The peptide according to claim 1, wherein the peptide useful for isolating and/or purifying proteins is selected from the group consisting of an arginine tag (Arg-tag), a histidine tag (His-tag), FLAG-tag, Strep-tag, and an epitope susceptible to being recognized by an antibody.

21. The peptide according to claim 20, wherein the peptide useful for isolating and/or purifying proteins is a polyhistidine tag.

\* \* \* \* \*